United States Patent
Bentley et al.

(10) Patent No.: US 9,446,139 B2
(45) Date of Patent: Sep. 20, 2016

(54) POLYMER-BASED COMPOSITIONS AND CONJUGATES OF HIV ENTRY INHIBITORS

(75) Inventors: Michael D. Bentley, Huntsville, AL (US); Xuan Zhao, Huntsville, AL (US); Harold Zappe, Harvest, AL (US)

(73) Assignee: Nektar Therapeutics, San Francisco, CA (US)

( * ) Notice: Subject to any disclaimer, the term of this patent is extended or adjusted under 35 U.S.C. 154(b) by 1860 days.

(21) Appl. No.: 11/082,229

(22) Filed: Mar. 15, 2005

(65) Prior Publication Data

US 2005/0226843 A1    Oct. 13, 2005

Related U.S. Application Data

(60) Provisional application No. 60/553,146, filed on Mar. 15, 2004.

(51) Int. Cl.
*A61K 47/48*    (2006.01)

(52) U.S. Cl.
CPC ................... *A61K 47/48215* (2013.01)

(58) Field of Classification Search
CPC .................................. A61K 47/48215
See application file for complete search history.

(56) References Cited

U.S. PATENT DOCUMENTS

| | | | |
|---|---|---|---|
| 5,739,208 A | 4/1998 | Harris | |
| 5,932,462 A | 8/1999 | Harris et al. | |
| 6,413,507 B1 | 7/2002 | Bentley et al. | |
| 6,451,313 B1 | 9/2002 | Maddon et al. | |
| 6,541,015 B2* | 4/2003 | Bentley et al. | 424/400 |
| 6,541,020 B1 | 4/2003 | Ding et al. | |
| 6,602,498 B2 | 8/2003 | Shen | |
| 6,767,993 B2 | 7/2004 | Bray et al. | |
| 7,199,223 B2* | 4/2007 | Bossard et al. | 530/383 |
| 2001/0011115 A1 | 8/2001 | Harris et al. | |
| 2003/0139571 A1 | 7/2003 | Dragic et al. | |
| 2004/0049018 A1 | 3/2004 | Bailon et al. | |
| 2004/0171542 A1 | 9/2004 | Bailon et al. | |
| 2004/0228869 A1 | 11/2004 | Olson et al. | |
| 2005/0143484 A1 | 6/2005 | Fang et al. | |

FOREIGN PATENT DOCUMENTS

| | | | | |
|---|---|---|---|---|
| WO | 01/03723 | | 1/2001 | |
| WO | 01/003723 | * | 1/2001 | |
| WO | WO 01/03723 | * | 1/2001 | ............ A61K 38/02 |
| WO | 01/62827 | | 8/2001 | |
| WO | 2004/012773 | | 2/2004 | |
| WO | 2004/013164 | * | 2/2004 | ............ C07K 14/16 |
| WO | 2004/013165 | | 2/2004 | |
| WO | WO 2004/013164 | * | 2/2004 | ............ C07K 14/16 |
| WO | 2004/022630 | | 3/2004 | |
| WO | 2004/029073 | | 4/2004 | |
| WO | 2004/060966 | | 7/2004 | |
| WO | 2004/060967 | | 7/2004 | |
| WO | 2004/060977 | | 7/2004 | |
| WO | 2004/063250 | | 7/2004 | |
| WO | WO 2004/063250 | * | 7/2004 | ............ C08G 75/00 |
| WO | 2005/000360 | | 1/2005 | |
| WO | 2005/089796 | | 9/2005 | |

OTHER PUBLICATIONS

Shearwater catalog 1997, pp. 1-17, submitted by Applicants on IDS.*
Chinese Office Action in Chinese Patent Application No. 200580008210.4 Date of Issuing Aug. 28, 2009.
PCT International Search Report in PCT Patent Application No. PCT/US2005/008632 Date of Mailing May 31, 2007.
PCT Written Opinion in PCT Patent Application No. PCT/US2005/008632 Date of Mailing May 31, 2007.
PCT International Preliminary Report on Patentability in PCT Patent Application No. PCT/US2005/008632 Date of Issuance Jun. 19, 2007.
Enzon Pharmaceuticals, Macromolecular Engineering Technologies, pp. 1-14, (2004).
Nektart™—Transforming Therapeutics, Nektar Molecule Engineering: Polyethylene Glycol and Derivatives for Advanced PEGylation, pp. 1-20, (Catalog—2003).
Nektart™—Transforming Therapeutics, Nektar Molecule Engineering: Polyethylene Glycol and Derivatives for Advanced PEGylation, pp. 1-24, (Catalog—2004).
NOF Corporation, PEG Derivatives Phospholipid and Drug Delivery Materials for Pharmaceuticals, pp. 1-46, (Catalogue 2003—$1^{st}$).
NOF Corporation, PEG Derivatives Phospholipid and Drug Delivery Materials for Pharmaceuticals, pp. 1-50, (Catalogue 2003—$2^{nd}$).
Polypure, Products; PEG amines; PEG acids and amino acids; PEG thiols and disulfides; Biotins, (Apr. 2004).
Polypure, Products; PEG amines; PEG acids and amino acids; PEG thiols and disulfides; Biotins, (Apr. 2005).
Quanta Biodesign, Labeling, Derivatization and Crosslinking Reagents for Biological and Related Materials with dPEG™, pp. 1-38, (Mar. 12, 2004).
Quanta Biodesign, Labeling, Modification and Crosslinking Reagents incorporating our unique monodispersed dPEG™ Technology, pp. 1-31, (Nov. 5, 2004).
Quanta Biodesign, Ltd., Leading innovator, producer and provider of monodisperse discrete PEG™(dPEG™) derivatives, pp. 1-51, (Product Catalog) (Updated: Jul. 18, 2005).
Quanta Biosesign, Ltd., Leading innovator, producer and provider of monodisperse discrete PEG™ (dPEG™) derivatives, pp. 1-51, (Product Catalog) (Updated: Nov. 17, 2005).
Shearwater Polymers, Inc., pp. 2-49, (Catalog—Mar. 1995).
Shearwater Polymers, Inc., Polyethylene Glycol Derivatives, pp. 1-53, (Catalog—Jul. 1997).

(Continued)

*Primary Examiner* — Suzanne Ziska
(74) *Attorney, Agent, or Firm* — Mark A. Wilson; Susan T. Evans

(57) ABSTRACT

Provided herein are water-soluble polymer conjugates and polymer-based compositions of HIV entry inhibitors. Also provided are methods for synthesizing and administering such conjugates and compositions.

22 Claims, 3 Drawing Sheets

(56) References Cited

OTHER PUBLICATIONS

Figure 1:
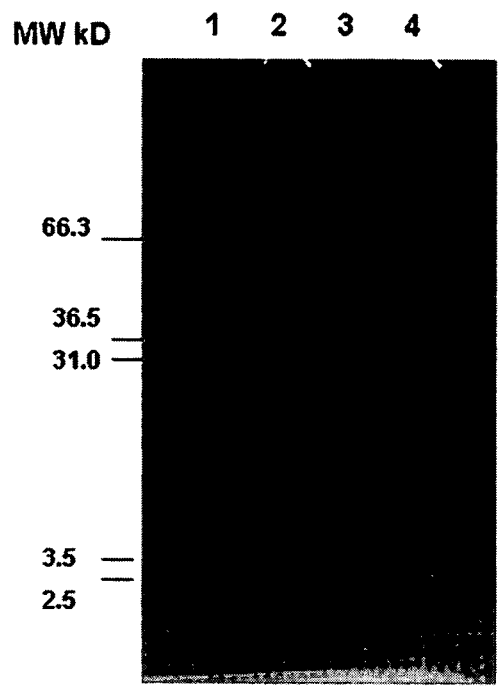

Shearwater Polymers, Inc., Polyethylene Glycol and Derivatives, pp. 1-50, (Catalog—2000).
Shearwater Corporation, Polyethylene Glycol and Derivatives for Biomedical Applications, pp. 1-17, (Catalog—2001).
Olson et al., "Differential Inhibition of Human Immunodeficiency Virus Type I Fusion, gp120 Binding, and CC-Chemokine Activity by Monoclonal Antibodies to CCR5," Journal of Virology, May 1999, vol. 73, No. 5, pp. 4145-4155.
Trkola et al., "Potent, Broad-Spectrum Inhibition of Human Immunodeficiency Virus Type 1 by the CCR5 Monoclonal Antibody PRO 140," Journal of Virology, Jan. 2001, vol. 75, No. 2, pp. 579-588.
Franti et al., "The CCR5 Co-Receptor Inhibitor PRO 140 Effectively Controls Established HIV-1 Infection in Vivo," 2002 9$^{th}$ Conference on Retroviruses and Opportunistic Infections, Abstract, 1 page.
Huff, Bob, "Notes on HIV Drugs in Development," GMHC Treatment Issues, vol. 17, No. ½, Jan./Feb. 2003, 4 pages.
McNicholl et al., "Summary of Pooled Efficacy and Safety Analyses of Enfuvirtide Treatment for 24 Weeks in TORO 1 and TORO 2 Phase III Trials in Highly Antiretroviral Treatment-experienced Patients," Mar. 7, 2003, AETC National Resource Center, http://www.aids-ed.org/aidsetc?page=croi0-10-05 5 pages.
Hoffman-La Roche Inc., "Study Results Demonstrate Safety and Antiviral Activity of T-1249," Jul. 3, 2002, Roche Pharmaceuticals in the U.S., http://www.rocheuse.com/newsroom/current/2002/pr2002070301.html, 3 pages.
Nektar Advanced PEGlyation Catalog 2004, Nektar Therapeutics, San Carlos, California, 27 pages.
Huet et al., "Long-lasting enfuvirtide carrier pentasaccharide conjugates with potent anti-human immunodeficiency virus type 1 activity", Antimicrobial Agents and Chemotherapy, vol. 54 No. 1, pp. 134-142 (2010).

\* cited by examiner

POLYMER-BASED COMPOSITIONS AND CONJUGATES OF HIV ENTRY INHIBITORS

CROSS REFERENCE TO RELATED APPLICATIONS

This application claims the benefit of priority to Provisional Application Ser. No. 60/553,146, filed Mar. 15, 2004 which is incorporated herein by reference in its entirety.

FIELD OF THE INVENTION

The present invention relates generally to the sustained delivery of HIV entry inhibitors (EI). More particularly, the invention relates to water-soluble polymer conjugates and polymer-based compositions of HIV entry inhibitors. In addition, the invention encompasses methods for synthesizing such conjugates and compositions, as well as methods for inhibiting HIV infection by administering the compositions described herein.

BACKGROUND OF THE INVENTION

AIDS (acquired immunodeficiency syndrome), first reported in the United States in 1981, is a worldwide epidemic. AIDS is caused by the human immunodeficiency virus (HIV), which acts to progressively destroy the body's ability to fight infections and certain kinds of cancers by killing or damaging cells of the body's immune system. By some estimates, nearly one million people in the United States may be presently infected with HIV.

When AIDS first surfaced in the United States, there were no medicines to combat HIV; however, over the past 11 years, drugs have been developed to fight both HIV infection and its associated infections and cancers. These drugs can be categorized into different classes based upon their mode of action. Three classes of anti-HIV drugs, although acting at different times during the viral life cycle, interrupt viral replication after the virus has infected a T-cell. These classes of anti-HIV medications include nucleoside reverse transcriptase inhibitors (NRTIs), protease inhibitors (PIs), and non-nucleoside reverse transcriptase inhibitors (NNRTIs). Drugs falling into these various classes include AZT, zalcitabine, dideoxyinosine, stavudine, and lamivudine (nucleoside reverse transcriptase inhibitors); delvaridine, nevirapine, and efravirenz (non-nucleoside reverse transcriptase inhibitors), and ritonavir, saquinivir, and indinavir (protease inhibitors). However, there is another class of antiretroviral agents, the entry inhibitors, that work differently than the previously described conventional classes of anti-HIV drugs. Rather than working against HIV post T-cell infection, an entry inhibitor actually prevents HIV from infecting a T-cell in the first place. More specifically, entry inhibitors work by attaching themselves to proteins on the surface of T-cells or proteins on the surface of HIV. In order for HIV to bind to T-cells, the proteins on HIV's outer coat must bind to the proteins on the surface of T-cells. Entry inhibitors prevent the occurrence of such binding. Some entry inhibitors target the gp120 or gp41 proteins on HIV's surface, while other entry inhibitors target the CD4 protein or the CCR5 or CXCR4 receptors on a T-cell's surface. Entry inhibitors include T-20 (also referred to as enfuvirtide), PRO-542, SCH-C, SCH-D, and T-1249. To date only one entry inhibitor, T-20, has been approved by the FDA. T-20 inhibits the fusion of HIV-1 with CD4+ cells.

Entry inhibitors (including fusion inhibitors) are a promising new type of anti-HIV drug. Entry inhibitors like T-20 are particularly attractive to HIV-positive individuals whom have not responded using the traditional anti-HIV drugs, e.g., PIs, NRTIs and NNRTIs, either alone or in combination therapy. T-20 is a 36 amino acid synthetic peptide having an acetylated N-terminus and the C-terminus modified as the carboxamide. T-20 (FUZEON™) received marketing approval from the FDA in March 2003. Unfortunately, despite high expections, sales of the drug have been hampered by its steep prices and more importantly, its difficulty of administration. T-20 is injected under the skin two times a day. Such frequent patient dosing can be very unattractive to patients—many of whom ultimately fail to maintain the necessary dosing regime, due to the high frequency of dosing, mode of administration, and general fatigue associated with preparing and administering the drug. Indeed, 98% of FUZEON™ patients reported at least one instance of painful or troublesome local injection site reactions (ISR). ISR symptoms include pain/discomfort, induration, erythema, and nodules/cysts. Reported hypersensitivity reactions include rash, fever, nausea and vomiting, chills, rigors, and hypotension. It has become increasingly clear that drugs such as T-20 are not easy drugs for patients to take. The pain associated with ISR is considered mild to moderate, and the mean duration of each ISR is around 7 days. Moreover, resistance to T-20 can develop fairly quickly if full doses are not taken on a consistent basis. (*GMHC Treatment Issues*, Vol. 17, No. 1/2, January/February 2003). Thus, there is a need in the art for improved anti-HIV agents, and in particular, improved entry inhibitors, having longer circulating half-lives in the bloodstream whilst maintaining a measurable, and more preferably a significant, degree of activity, thereby allowing less frequent patient dosing and thus a reduced occurrence of local injection site reactions. This invention meets these needs.

SUMMARY OF THE INVENTION

Accordingly, in one aspect, the invention provides sustained delivery compositions of anti-retroviral HIV agents, and in particular, peptidyl-based entry inhibitors such as T-20 and T-1249, among others. The conjugates and compositions of the invention possess sustained release properties, e.g., longer circulating half-lives in the bloodstream than their unmodified EI counterparts, thereby solving some of the administration-related problems related to unmodified EIs such as T-20.

The conjugates and compositions described herein advantageously reduce immunogenicity. Equally important, the present conjugates and compositions require a decreased frequency of dosing compared to traditional EI compositions absent water-soluble polymer, either in conjugated or non-conjugated form. Thus, the conjugates and compositions provided herein advantageously decrease the number of painful injections and associated local injection site reactions typically endured by HIV-1 infected subjects taking the corresponding entry-inhibitor drugs absent a water-soluble polymer, either covalently attached thereto or associated therewith, by virtue of their sustained release properties which act to provide extended and therapeutic levels of an EI in the bloodstream, preferably a polypeptide based EI.

In one aspect, the invention is directed to a conjugate of a water soluble polymer and an entry inhibitor compound.

Exemplary conjugates in accordance with this aspect of the invention are provided in the Tables herein.

In a preferred embodiment, the conjugates and compositions of the invention are degradable, that is to say, comprise at least one degradable linkage, preferably a hydrolyzable linkage.

For example, a hydrolyzable linkage contained in a conjugate or composition of the invention may contain a hydrolyzable moiety such as a carboxylate ester, a phosphate ester, a carbamate, an anhydride, an acetal, a ketal, an acyloxyalkyl ether, an imine, an orthoester, a thioester, a thiolester, or a carbonate.

In one preferred embodiment, the hydrolyzable moiety is a hydrolyzable carbamate, ester or a carbonate.

In yet a further embodiment, a conjugate of the invention possesses the following structure:

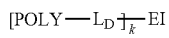
                                               I where POLY is a water-soluble polymer, LD is a degradable linkage, EI is an entry inhibitor, and k corresponds to the number of reactive sites on the EI to which an independent polymer segment (POLY-$L_D$) is covalently attached. Each of the polymer segments (i.e., individual components of the polymer segment) is independently selected, although preferably, each of the polymer segments covalently attached to the EI is the same. Typically, k ranges from about 1 to about 8, that is to say, is selected from the group consisting of 1, 2, 3, 4, 5, 6, 7 and 8. Preferably, k is 1, 2, 3, or 4, or even more preferably, is 1.

In a preferred embodiment of this and other aspects of the invention, the water soluble polymer is a polyethylene glycol.

The water soluble polymer, e.g., polyethylene glycol, typically has a molecular weight falling within one of the following ranges: from about 500 Daltons to about 100,000 Daltons, from about 2,000 Daltons to about 85,000 Daltons, from about 5,000 Daltons to about 60,000 Daltons, from about 10,000 Daltons to about 50,000 Daltons, or from about 15,000 Daltons to about 40,000 Daltons, and may possess any of a number of architectures (e.g., linear, branched, forked, and the like).

Entry inhibitors for use in the conjugates and compositions of the invention include, for example, T-20, T-1249, PRO 542 (also known as CD4-IgG2), PRO-140, PRO-367, SCH-417690, TXN-355, UK-427, UK-857, GSK-873, GSK-140, PA9, PA10, PA11, and PA12. In a particular embodiment, the entry inhibitor is T-20, T-1249, PRO 542, or PRO-140.

In a further embodiment, the EI reactive site to which a polymer segment such as that shown above in structure I is attached is independently selected from the group consisting of the N-terminal, the C-terminal, an amino group, a hydroxyl group, and a thiol.

Generally, the $L_D$ possesses a length such as from about 1 to about 20 atoms, from about 2 to about 15 atoms, or from about 3 to about 10 atoms. That is to say, typically, $L_D$ has an overall atom length selected from the group consisting of 1, 2, 3, 4, 5, 6, 7, 8, 9, 10, 11, 12, 13, 14, 15, 16, 17, 18, 19, and 20.

Yet another particular embodiment of the invention encompasses a conjugate comprising one of the following generalized structures:

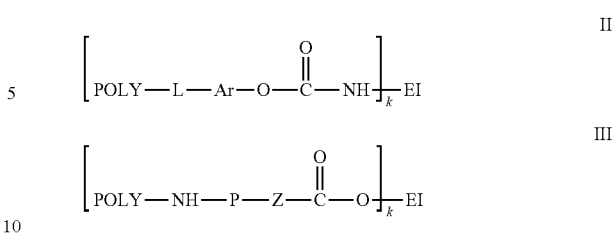

where L is either —O— or —NH—C(O), Ar is an aromatic group, such as an ortho, meta, or para-substituted phenyl, —NH— in structure II is an amino residue from EI, P is a spacer, Z is —O—, —NH— or —CH$_2$— and O in structure III is a hydroxyl residue from EI.

In a more particular embodiment, in structure III, P, when taken together with —NH—P—Z—C(O), is the residue of a naturally or non-naturally occurring amino acid.

Also forming part of this aspect of the present invention is a conjugate corresponding to structure III, wherein "POLY-NH—" corresponds to polymers 1-1 to 1-40 in Table 1, absent the EI portion.

In yet an additional embodiment, a conjugate in accordance with the invention is characterized by the structure:

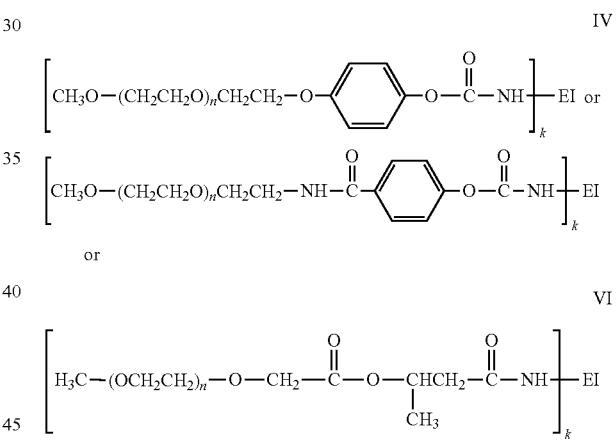

where n ranges from 2 to about 3400.

Also forming part of the invention are conjugates of multi-armed water soluble polymers.

In one particular embodiment of this aspect of the invention, the multi-armed polymer comprises a central core from which extends three or more polymer arms which are typically homopolymeric or co-polymeric.

In yet another embodiment of a multi-armed polymer conjugate in accordance with the invention, each polymer arm comprises a copolymer comprising an inner polypeptide segment covalently attached to a central core and an outer hydrophilic polymer segment covalently attached to the polypeptide segment.

Exemplary conjugates in accordance with this aspect of the invention will generally comprise the following structure:

$$R \text{—}(\text{POLY-}L_D\text{-EI})_y \qquad\qquad \text{VII}$$

wherein R is a core molecule, POLY is a water-soluble polymer, $L_D$ is a degradable linkage, EI is an entry inhibitor, and y ranges from about 3 to 15.

Alternatively, the conjugate may comprise the structure:

ent. The compositions encompass all types of formulations and in particular those that are suited for injection, such as powders that can be reconstituted, as well as liquids (e.g., suspensions and solutions).

VIII 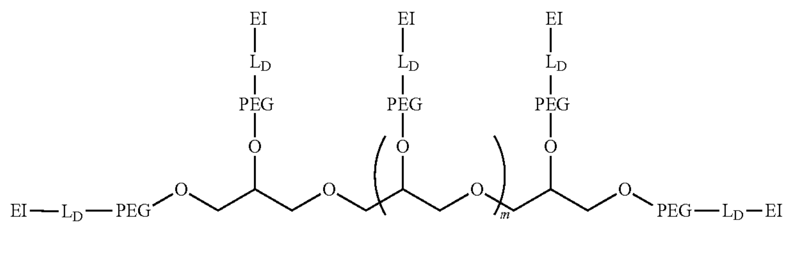 where m is selected from 3, 4, 5, 6, 7, and 8.

In yet a further and more specific embodiment, a conjugate of this type may correspond to the structure:

IX 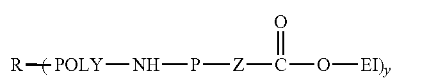 where P is a spacer, Z is —O—, —NH—, or $—CH_2—$, and O is a hydroxyl residue from EI. In a preferred embodiment, P, when taken together with —NH—P—Z—C(O)— is a residue of a naturally or non-naturally occurring amino acid.

In yet another aspect, the invention encompasses a composition comprising a plurality of mono-polymer EI conjugates, meaning EI conjugates each having one polymer reagent covalently attached to the EI, but at different reactive sites or positions thereupon.

In another aspect of the invention, an EI is admixed with a hydrogel, more preferably, a hydrolytically degradable hydrogel, i.e., one that degrades under physiological conditions. Such hydrogels may be cross-linked or non-cross-linked. In a preferred embodiment, the hydrogel is a non-reverse gelation hydrogel comprising an entry enhibitor, and as one of the gel components, a poly(alkylene oxide). In a particular embodiment, the entry inhibitor is in the form of a water-soluble polymer conjugate. Alternatively, the entry inhibitor is optionally covalently attached to one or more gel components.

Also forming part of the invention is a method for making a polymer conjugate. The method comprises the step of contacting, under conjugation conditions, an entry inhibitor with a water soluble polymeric reagent to form a polymer entry inhibitor conjugate. Preferably such conjugate comprises a degradable linkage.

In yet a further aspect, provided is a method for preparing a non-reverse gelation hydrogel comprising an entry inhibitor. Such method includes the step of contacting suitable hydrogel precursor reagents with one another and with the entry inhibitor under conditions effective to promote gelling of the precursor reagents, to thereby form a non-reverse gelation hydrogel having the entry inhibitor entrapped therein. The entry inhibitor is either in conjugated or unconjugated form, and the hydrogel precursor reagents do not exhibit reverse gelation properties.

In still another embodiment of the invention, compositions are provided comprising a conjugate of the invention in combination with a pharmaceutically acceptable excipi- In an additional embodiment of the invention, a method of inhibiting HIV infection is provided. In the method, an EI-conjugate or pharmaceutical composition comprising a therapeutically effective amount of such conjugate is administered to a subject or cells infected with HIV-1. Typically, the step of administering an EI conjugate or composition is effected by injection (e.g., intramuscular injection, intravenous injection, subcutaneous injection, and so forth).

Additional objects, advantages and novel features of the invention will be set forth in the description that follows, and in part, will become apparent to those skilled in the art upon reading the following, or may be learned by practice of the invention.

BRIEF DESCRIPTION OF THE FIGURES

FIG. 1. is an SDS-PAGE gel of exemplary conjugate samples from Example 1 (lane 4) and Example 2 (4:1 molar ratio) (lane 3). Lane 2 corresponds to free peptide, T-1249, as a reference. Lane 1 corresponds to MARK 12 standards.

FIG. 2. is an SDS-PAGE gel of exemplary conjugate samples from Example 2 (DMSO solvent system) and Example 3 (mixed aqueous DMSO solvent system). Lane 1 corresponds to MARK 12 standards. Lane 2 corresponds to free peptide, T1249; Lane 3 corresponds to a 1:1 molar ratio DMSO reaction (Example 2); Lane 4 corresponds to a 1:2 molar ratio DMSO reaction (Example 2); Lane 5 corresponds to an aqueous/DMSO mixed reaction (1:1) using a 4:1 molar ratio (Example 3).

FIG. 3. illustrates an HPLC chromatogram for the conjugate mixture from Example 3, 1:1 molar ratio. The sample injected was a 1:1 molar ratio in an aqueous/DMSO reaction and showed a pepide and product distribution similar to that seen in lane 3 of FIG. 2.

FIG. 4 corresponds to an SDS-PAGE gel of purified mono-PEG T1249, as described in Example 5A. Lane 1 is the standard, lane 2 is T1249 only, and lanes 3 and 4 represent different loaded amounts of the final purified preparation; and FIG. 5 is a plot demonstrating hydrolysis in vitro of a mono-PEGylated conjugate prepared using a model peptide covalently attached to an exemplary degradable mPEG reagent, mPEG-succinimidyl phenyl-carbonate, 20 kDa (Example 5.D).

DETAILED DESCRIPTION OF THE INVENTION

Definitions

Before describing the present invention in detail, it is to be understood that this invention is not limited to the particular polymers, hydrogels, synthetic techniques, entry inhibitors, and the like, as such may vary, as will be apparent from the accompanying description and figures.

It must be noted that, as used in this specification and the intended claims, the singular forms "a," "an," and "the" include plural referents unless the context clearly dictates otherwise. Thus, for example, reference to "a polymer" includes a single polymer as well as two or more of the same or different polymers, reference to a "an optional excipient" refers to a single optional excipient as well as two or more of the same or different optional excipients, and the like.

In describing and claiming the present invention, the following terminology will be used in accordance with the definitions described below.

"PEG," "polyethylene glycol" and "poly(ethylene glycol)" as used herein, are interchangeable and meant to encompass any water-soluble poly(ethylene oxide). Typically, PEGs for use in accordance with the invention comprise the following structure "—$(OCH_2CH_2)_n$—" where (n) ranges from 2 to about 4000. As used herein, the term "PEG" may also refer to the particular structures "—$CH_2CH_2$—O$(CH_2CH_2O)_n$—$CH_2CH_2$—" or "—$(OCH_2CH_2)_nO$—," depending upon whether or not the terminal oxygens have been displaced. Throughout the specification and claims, it should be remembered that the term "PEG" includes structures having various terminal or "end capping" groups and so forth. The term "PEG" refers to a polymer that contains a majority, that is to say, greater than 50%, of —$OCH_2CH_2$— repeating subunits. With respect to specific forms, the PEG can take any number of a variety of molecular weights, as well as structures or geometries, such as "branched," "linear," "forked," "multifunctional," and the like, to be described in greater detail below.

The terms "end-capped" and "terminally capped" are used interchangeably herein to refer to a terminal or endpoint of a polymer having an end-capping moiety. Typically, although not necessarily, the end-capping moiety comprises a hydroxy or $C_{1-20}$ alkoxy group or benzyloxy group, more preferably a $C_{1-10}$ alkoxy group, and still more preferably a $C_{1-5}$ alkoxy group. Thus, examples of end-capping moieties include alkoxy (e.g., methoxy, ethoxy and benzyloxy), as well as aryl, heteroaryl, cyclo, heterocyclo, and the like. It must be remembered that the end-capping moiety may include one or more atoms of the terminal monomer in the polymer [e.g., the end-capping moiety "methoxy" in $CH_3(OCH_2CH_2)_n$—]. In addition, saturated, unsaturated, substituted and unsubstituted forms of each of the foregoing are envisioned. Moreover, the end-capping group can also be a silane. The end-capping group can also advantageously comprise a detectable label. When the polymer has an end-capping group comprising a detectable label, the amount or location of the polymer and/or the moiety (e.g., active agent) to which the polymer is coupled can be determined by using a suitable detector. Such labels include, without limitation, fluorescers, chemiluminescers, moieties used in enzyme labeling, calorimetric (e.g., dyes) labels, metal ions, radioactive moieties, and the like. Suitable detectors include photometers, films, spectrometers, and the like. The end-capping group can also advantageously comprise a phospholipid. When the polymer has an end-capping group comprising a phospholipid, unique properties are imparted to the polymer and the resulting conjugate. Exemplary phospholipids include, without limitation, those selected from the class of phospholipids called phosphatidylcholines. Specific phospholipids include, without limitation, those selected from the group consisting of dilauroylphosphatidylcholine, dioleylphosphatidylcholine, dipalmitoylphosphatidylcholine, disteroylphosphatidylcholine, behenoylphosphatidylcholine, arachidoylphosphatidylcholine, and lecithin.

"Non-naturally occurring" with respect to a polymer as described herein, means a polymer that in its entirety is not found in nature. A non-naturally occurring polymer of the invention may, however, contain one or more monomers or segments of monomers that are naturally occurring, so long as the overall polymer structure is not found in nature.

The term "water soluble" as in a "water-soluble polymer" polymer is any polymer that is soluble in water at room temperature. Typically, a water-soluble polymer will transmit at least about 75%, more preferably at least about 95%, of light transmitted by the same solution after filtering. On a weight basis, a water-soluble polymer will preferably be at least about 35% (by weight) soluble in water, more preferably at least about 50% (by weight) soluble in water, still more preferably about 70% (by weight) soluble in water, and still more preferably about 85% (by weight) soluble in water. It is most preferred, however, that the water-soluble polymer is about 95% (by weight) soluble in water or completely soluble in water.

Molecular weight, in the context of a water-soluble polymer of the invention, such as PEG, can be expressed as either a number average molecular weight or a weight average molecular weight. Unless otherwise indicated, all references to molecular weight herein refer to the weight average molecular weight. Both molecular weight determinations, number average and weight average, can be measured using gel permeation chromatography or other liquid chromatography techniques. Other methods for measuring molecular weight values can also be used, such as the use of end-group analysis or the measurement of colligative properties (e.g., freezing-pint depression, boiling-point elevation, or osmotic pressure) to determine number average molecular weight or the use of light scattering techniques, ultracentrifugation or viscometry to determine weight average molecular weight. The polymers of the invention are typically polydisperse (i.e., number average molecular weight and weight average molecular weight of the polymers are not equal), possessing low polydispersity values of preferably less than about 1.2, more preferably less than about 1.15, still more preferably less than about 1.10, yet still more preferably less than about 1.05, and most preferably less than about 1.03.

By overall atom length, e.g., in the context of a linker of the invention, is meant the number of atoms in a single chain, not counting substituents. For instance, —$CH_2$— counts as one atom with respect to overall linker length, —$CH_2CH_2O$— counts as 3 atoms in length, and a non-linear group such as a phenyl ring counts as 4 atoms in length.

The term "active" or "activated" when used in conjunction with a particular functional group, refers to a reactive functional group that reacts readily with an electrophile or a nucleophile on another molecule. This is in contrast to those groups that require strong catalysts or highly impractical reaction conditions in order to react (i.e., a "non-reactive" or "inert" group).

As used herein, the term "functional group" or any synonym thereof is meant to encompass protected forms thereof as well as unprotected forms.

The terms "linkage" or "linker" are used herein to refer to an atom or a collection of atoms optionally used to link interconnecting moieties such as a terminus of a polymer segment and an entry inhibitor (e.g., T-20 or T-1249). A linker may be hydrolytically stable or may include a physiologically hydrolyzable or enzymatically degradable linkage.

"Alkyl" refers to a hydrocarbon chain, typically ranging from about 1 to 15 atoms in length. Such hydrocarbon chains are preferably but not necessarily saturated and may be branched or straight chain, although typically straight chain is preferred. Exemplary alkyl groups include methyl, ethyl, propyl, butyl, pentyl, 1-methylbutyl, 1-ethylpropyl, 3-methylpentyl, and the like. As used herein, "alkyl" includes cycloalkyl as well as cycloalkylene-containing alkyl.

"Lower alkyl" refers to an alkyl group containing from 1 to 6 carbon atoms, and may be straight chain or branched, as exemplified by methyl, ethyl, n-butyl, i-butyl, and t-butyl.

"Cycloalkyl" refers to a saturated or unsaturated cyclic hydrocarbon chain, including bridged, fused, or spiro cyclic compounds, preferably made up of 3 to about 12 carbon atoms, more preferably 3 to about 8 carbon atoms. "Cycloalkylene" refers to a cycloalkyl group that is inserted into an alkyl chain by bonding of the chain at any two carbons in the cyclic ring system.

"Alkoxy" refers to an —O—R group, wherein R is alkyl or substituted alkyl, preferably $C_{1-6}$ alkyl (e.g., methoxy, ethoxy, propyloxy, and so forth).

The term "substituted" as in, for example, "substituted alkyl," refers to a moiety (e.g., an alkyl group) substituted with one or more noninterfering substituents, such as, but not limited to: alkyl, $C_{3-8}$ cycloalkyl, e.g., cyclopropyl, cyclobutyl, and the like; halo, e.g., fluoro, chloro, bromo, and iodo; cyano; alkoxy, lower phenyl; substituted phenyl; and the like. "Substituted aryl" is aryl having one or more noninterfering groups as a substituent. For substitutions on a phenyl ring, the substituents may be in any orientation (i.e., ortho, meta, or para).

"Noninterfering substituents" are those groups that, when present in a molecule, are typically nonreactive with other functional groups contained within the molecule.

"Aryl" means one or more aromatic rings, each of 5 or 6 core carbon atoms. Aryl includes multiple aryl rings that may be fused, as in naphthyl or unfused, as in biphenyl. Aryl rings may also be fused or unfused with one or more cyclic hydrocarbon, heteroaryl, or heterocyclic rings. As used herein, "aryl" includes heteroaryl.

"Heteroaryl" is an aryl group containing from one to four heteroatoms, preferably sulfur, oxygen, or nitrogen, or a combination thereof. Heteroaryl rings may also be fused with one or more cyclic hydrocarbon, heterocyclic, aryl, or heteroaryl rings.

"Heterocycle" or "heterocyclic" means one or more rings of 5-12 atoms, preferably 5-7 atoms, with or without unsaturation or aromatic character and having at least one ring atom that is not a carbon. Preferred heteroatoms include sulfur, oxygen, and nitrogen.

"Substituted heteroaryl" is heteroaryl having one or more noninterfering groups as substituents.

"Substituted heterocycle" is a heterocycle having one or more side chains formed from noninterfering substituents.

"Electrophile" and "electrophilic group" refer to an ion or atom or collection of atoms, that may be ionic, having an electrophilic center, i.e., a center that is electron seeking, capable of reacting with a nucleophile.

"Nucleophile" and "nucelophilic group" refers to an ion or atom or collection of atoms that may be ionic having a nucleophilic center, i.e., a center that is seeking an electrophilic center or with an electrophile.

A "physiologically cleavable" or "hydrolyzable" or "degradable" bond is a bond that reacts with water (i.e., is hydrolyzed) under physiological conditions. The tendency of a bond to hydrolyze in water will depend not only on the general type of linkage connecting two central atoms but also on the substituents attached to these central atoms. Appropriate hydrolytically unstable or weak linkages include but are not limited to carboxylate ester, phosphate ester, anhydrides, acetals, ketals, acyloxyalkyl ether, imines, orthoesters, peptides and oligonucleotides. In certain embodiments of the invention, preferred are bonds that have a hydrolysis half-life at pH 8, 25° C. of less than about 30 minutes, although such preference is not intended to be limiting in any sense.

An "enzymatically degradable linkage" means a linkage that is subject to degradation by one or more enzymes.

A "hydrolytically stable" linkage or bond refers to a chemical bond, typically a covalent bond, that is substantially stable in water, that is to say, does not undergo hydrolysis under physiological conditions to any appreciable extent over an extended period of time. Examples of hydrolytically stable linkages include, but are not limited to, the following: carbon-carbon bonds (e.g., in aliphatic chains), ethers, amides, urethanes, and the like. Generally, a hydrolytically stable linkage is one that exhibits a rate of hydrolysis of less than about 1-2% per day under physiological conditions. Hydrolysis rates of representative chemical bonds can be found in most standard chemistry textbooks.

"Pharmaceutically acceptable excipient or carrier" refers to an excipient that may optionally be included in the compositions of the invention and that causes no significant adverse toxicological effects to the patient. "Pharmacologically effective amount," "physiologically effective amount," and "therapeutically effective amount" are used interchangeably herein to mean the amount of an entry inhibitor conjugate or composition (e.g., a hydrogel) that is needed to provide a desired level of the conjugate (or corresponding unconjugated entry inhibitor) in the bloodstream or in the target tissue. The precise amount will depend upon numerous factors, e.g., the particular entry inhibitor, the components and physical characteristics of the therapeutic composition, intended patient population, individual patient considerations, and the like, and can readily be determined by one skilled in the art, based upon the information provided herein.

"Branched", in reference to the geometry or overall structure of a polymer, refers to a polymer having 2 or more polymer "arms" extending from a branch point. A branched polymer may possess 2 polymer arms, 3 polymer arms, 4 polymer arms, 6 polymer arms, 8 polymer arms or more. A subset of branched polymers are multi-armed polymers, that is to say, polymers having 3 or more arms extending from a central core.

A "branch point" refers to a bifurcation point comprising one or more atoms at which a polymer or linking group splits or branches from a linear structure into one or more additional polymer arms.

The term "reactive" or "activated" refers to a functional group that reacts readily or at a practical rate under conventional conditions of organic synthesis. This is in contrast to those groups that either do not react or require strong catalysts or impractical reaction conditions in order to react (i.e., a "nonreactive" or "inert" group).

A functional group in "protected form" refers to a functional group bearing a protecting group. As used herein, the term "functional group" or any synonym thereof is meant to encompass protected forms thereof. Representative protecting groups are described in, Greene, T., Wuts, P. G., "Protective Groups in Organic Synthesis", 3rd Ed., John Wiley & Sons, Inc., 1999.

"Multi-functional" means a polymer having 3 or more functional groups contained therein, where the functional groups may be the same or different. Multi-functional polymeric reagents of the invention will typically contain from about 3-100 functional groups, or from 3-50 functional groups, or from 3-25 functional groups, or from 3-15 functional groups, or from 3 to 10 functional groups, or will contain 3, 4, 5, 6, 7, 8, 9 or 10 functional groups within the polymer backbone.

"Entry inhibitors" are a particular class of antiretroviral drugs that target step(s) in the life cycle of HIV that occur prior to viral infection of a target cell. Specifically, they are compounds designed to disrupt HIV-1 replicative functions, most prominently, HIV-1 cell fusion and entry. Entry inhibitors include fusion inhibitors, attachment inhibitors, and co-receptor inhibitors. All entry inhibitors work by blocking the ability of HIV to successfully enter and thereby infect a target cell. Typically, although not necessarily, the subject entry inhibitor is a peptide or a modified peptide, such as a hybrid fusion protein, or other chimeric peptide, having at least one electrophilic group or nucleophilic group suitable for reaction with a polymeric reagent. The term "Entry Inhibitor" or "EI" encompasses both the entry inhibitor prior to as well as following conjugation.

A "hydrogel" is a material that absorbs a solvent (e.g. water), undergoes rapid swelling without discernible dissolution, and maintains three-dimensional networks capable of reversible deformation. Hydrogels may be uncrosslinked or crosslinked. Covalently (chemically) crosslinked networks of hydrophilic polymers, such as PEG, can form hydrogels (or aquagels) in the hydrated state. Uncrosslinked hydrogels are typically block copolymers having hydrophilic and hydrophobic regions. These uncrosslinked materials can form hydrogels when placed in an aqueous environment, due to physical crosslinking forces resulting from ionic attractions, hydrogen bonding, Van der Waals forces, etc. They are able to absorb water but do not dissolve due to the presence of hydrophobic and hydrophilic regions.

"Substantially" or "essentially" means nearly totally or completely, for instance, 95% or greater of some given quantity.

The term "patient," refers to a living organism suffering from or prone to a condition that can be prevented or treated by administration of an active agent of the invention (e.g., conjugate), and includes both humans and animals.

"Optional" or "optionally" means that the subsequently described circumstance may or may not occur, so that the description includes instances where the circumstance occurs and instances where it does not.

Amino acid residues in peptides are abbreviated with either single letter abbreviations or the corresponding amino acid abbreviations as follows:

| F | Phe | Phenylalanine |
| L | Leu | Leucine is Leu |
| I | Ile | Isoleucine |
| M | Met | Methionine |
| V | Val | Valine |
| S | Ser | Serine |
| P | Pro | Proline |
| T | Thr | Threonine |
| A | Ala | Alanine |
| Y | Tyr | Tyrosine |
| H | His | Histidine |

-continued

| Q | Gln | Glutamine |
| N | Asn | Asparagine |
| K | Lys | Lysine |
| D | Asp | Aspartic Acid |
| E | Glu | Glutamic Acid |
| C | Cys | Cysteine |
| W | Trp | Tryptophan |
| R | Arg | Arginine |
| G | Gly | Glycine |

Overview

Sustained Release Polymer Compositions of Entry Inhibitors

As stated previously, the present invention provides compositions and methods for sustained delivery of HIV entry inhibitor compounds such as T-20, T-1249, and others. Described herein are exemplary polymers, conjugates and compositions for prolonging the half-life of short-acting entry inhibitor compounds, particularly those that are peptide-based, whilst also maintaining at least a measurable, and more preferably, a significant degree of their retroviral activity upon administration. In certain instances, preferred are polymer conjugates having one or more hydrolyzable linkages designed to release the polymer portion of the conjugate in-vivo, or degradable hydrogel-based compositions, to be described in greater detail herein. In particular for drugs such as entry inhibitors, conjugates possessing one or more degradable linkages possess the advantage of having both a prolonged circulating half-life, and exhibiting bioactivity in vivo due to the degradable nature of the polymer attachment, since the polymer is released from the entry inhibitor upon hydrolysis. Thus, in such embodiments, the impact of the size and position of polymer attachment on the ability of the EI to prevent HIV from entering T-cells is not of particular concern, since the polymer portion of the molecule falls off in the body to release the entry inhibitor.

Entry Inhibitors

Entry Inhibitors

The conjugates and compositions of the invention comprise at least one anti-HIV drug that is preferably an entry inhibitor. Entry inhibitors are designated generically in the structures herein as "EI". Entry inhibitors preferred for use in the invention are those that are peptide-based, that is to say, comprising three or more contiguous amino acid residues. Such EIs include T-20, T-1249, PRO 542 (also known as CD4-IgG2), PRO-140, PRO-367, SCH-417690, TXN-355, UK-427, UK-857, GSK-873, and GSK-140.

Turning to the first entry inhibitor discussed above, T-20 is a linear 36 amino acid synthetic peptide having an acetylated N-terminus and a carboxamide group at its C-terminus. The molecular weight of T-20 is 4492. T-20 is composed of naturally occurring L-amino acid residues.

T-20 interferes with the entry of HIV-1 into cells by inhibiting fusion of viral and cellular membranes. T-20 binds to the first heptad repeat (HR1) in the gp41 subunit of the viral envelope glycoprotein, thereby preventing the conformational changes required for membrane fusion. HR1 becomes accessible to T-20 only after gp120 binds CD4. Co-receptor binding is believed to induce the final conformational changes that lead to membrane fusion. T-20 appears to bind to a structural intermediate in the fusion process, and seems to possess a very narrow kinetic window in which to intercalate itself into the merging cells. Due to its mechanism of action, preferred in one embodiment of the invention is a low molecular weight polymer for covalent attachment to a fusion inhibitor such as T-20, or in an alternative embodiment, a polymer having one or more hydrolyzable linkages, such that binding by T-20 to the first helical region of gp41 (HR1) is not impeded, since the polymer falls off upon hydrolysis in vivo.

For use in the present invention, the T-20 polypeptide sequence may be blocked and/or derivatized at one or both of its amino or carboxy termini, as described in U.S. Pat. No. 5,464,933, or may possess a blocking group at one or more of the lysine positions, e.g., to assist in site-selective polymer attachment, depending upon the chemistry employed to attach the polymer to the EI. The sequence of T-20 contains lysines at positions Lys18 and Lys28, each or both of which, in certain embodiments of the invention, are preferred for covalent attachment of a water-soluble polymer.

In particular, the tyrosine amino terminus may be blocked or derivatized with an aryl group and the phenylalanine carboxy terminis may be blocked or derivatized with an amino group.

Additional T-20-like sequences contemplated for use in the present invention comprise amino acids 638 to 673 of the HIV-$_{LAI}$ gp41 protein, and fragments, analogs, and homologs thereof, as described in U.S. Pat. No. 5,464,933, the contents of which are expressly incorporated herein by reference. Particularly preferred peptide sequences correspond to SEQ ID NOs: 1, 3, 4, 5, 6, and 7 as described in U.S. Pat. No. 5,464,933. Preferred water-soluble polymer attachment sites include the amino group of lysine(s), the N-terminal, the C-terminal, hydroxyl groups present on tyrosine, threonine, or serine.

```
YTNTIYTLLEESQNQQEKNEQELLELDKWASLWNWF    SEQ ID NO:2

YTGIIYNLLEESQNQQEKNEQELLELDKWANLWNWF    SEQ ID NO:3

YTSLIYSLLEKSQIQQEKNEQELLELDKWASLWNWF    SEQ ID NO:4

LEANISKSLEQAQIQQEKNMYELQKLNSWDIFGNWF    SEQ ID NO:5

LEANISQSLEQAQIQQEKNMYELQKLNSWDVFTNWL,   SEQ ID NO:6
```

T-1249 represents another entry inhibitor for use in the conjugates of the present invention. Similar to T-20, T-1249 is also derived from various retroviral envelope (gp41) protein sequences, but possesses pharmacokinetic properties that are somewhat improved over those of T-20. T-1249 is a hybrid polypeptide that contains a core polypeptide sequence linked to an enhancer petpide sequence. T-1249 possesses 39 amino acids and binds to a slightly different region of HIV gp41 than T-20. The amino acid sequence of T-1249 is shown in FIG. 13B of U.S. Pat. No. 6,656,906. T1249 exhibits in vitro activity against HIV-1, HIV-2, and SIV isolates.

```
                                        SEQ ID NO:7
WQEWEQKITALLEQAQIQQEKNEYELQKLDKWASLWEWF.
```

In the polypeptide sequence of T-1249, the N-terminus amino acid is tryptophan and the C terminus amino acid is phenylalanine. As described in Table 1 of U.S. Pat. No. 6,348,568, (SEQ. ID NO. 1071), the T-1249 sequence may be blocked and/or derivatized at one or both of its amino and carboxy termini. For example, the tryptophane terminus may be blocked or derivatized with an acyl group and the phenylalanine carboxy terminus may be blocked with an amino group, thereby resulting in formation of an amide functionality. The sequence of T-1249 contains lysines at the following four positions, which, depending upon the type of polymer reagent employed, may be suitable for covalent attachment of a water-soluble polymer (Lys7, Lys21, Lys28 and Lys31).

Additional exemplary entry inhibitor sequences (similar to those of T-1249) for use in the present invention are described in U.S. Pat. No. 6,656,906, the contents of which are expressly incorporated herein by reference. Particularly preferred sequences are those shown in FIGS. 13 A-C in U.S. Pat. No. 6,656,906. Methods useful for determining the antiviral activity of any of the above hybrid gp-41 derived polypeptide sequences, or the activity of a corresponding polymer conjugate or composition thereof, are also described in U.S. Pat. No. 6,656,906.

Another preferred peptide-based entry inhibitor is PRO-542, a hybrid fusion protein that combines the HIV-binding region of the CD4 receptor with a human antibody molecule. PRO 542 neutralizes HIV by binding to gp120, thereby preventing viral attachment to host cells. More particularly, PRO 542 is a CD4-IgG2 chimeric heterotetramer having a sequence of amino acids as described in U.S. Pat. No. 6,187,748, the contents of which are expressly incorporated herein by reference. Even more specifically, PRO 542 is made up of the N-terminal domains of human CD4 fused to the light and heavy chain constant regions of IgG2. PRO 542 is considered an attachment inhibitor, and acts very early in the viral entry process. Assays such as a syncytium inhibition assay and methods for determining the antiviral properties of such hybrid fusion proteins are described in U.S. Pat. No. 6,187,748, and can be employed by one skilled in the art to similarly determine the antiviral activity of the corresponding polymer conjugates or compositions. Preferred embodiments of the invention are those in which a water soluble polymer such as PEG is covalently attached to PRO 542, or any one of the other entry inhibitors described herein, via a degradable covalent linkage, to be described in greater detail below.

Additional non-limiting examples of peptide-based entry inhibitors for use in the present invention include CCR5 peptides, both sulfonated and non-sulfonated forms thereof, e.g., PRO 140, and PRO 367. Sulfated CCR5 peptides are described in U.S. Patent Application Publication No. 2003/0139571.

PRO 140 (previously referred to as PA14) is a mouse immunoglobulin G1 humanized monoclonal antibody which is classified as a CCR5 coreceptor inhibitor. PRO 140, and anti-CCR5 monoclonal antibody, binds to a complex epitope spanning multiple extracellular domains on CCR5. It potently inhibits CCR5-mediated HIV-1 entry on target cells, namely CD4+ T cells and macrophages, at concentrations that do not prevent CC-chemokine signaling (Trkola, A., et al., *Journal of Virology*, January 2001, Vol. 75, No. 2, 579-588). Preparation, isolation, and purification of PRO 140 is typically carried out as described in Olson, W. C., et al., 1999, *J. Virol.* 73:4145-4155. The monoclonal antibody, PRO 140, also corresponds to ATCC Accession No. HB-12610, as described in Olsen, et al, U.S. Patent Application Publication No. 2004/0228869.

Additional monoclonal antibodies suitable for use in the present invention include antibodies designated as PA8 (ATCC Accession No. HB-12605), PA9 (ATCC Accession No. HB-12606), PA10 (ATCC Accession No. HB-12607), PA1 (ATCC Accession No. HB-12608), and PA12 (ATCC Accession No. HB-12609) as described in Olsen, et al., U.S. Patent Application Publication No. 2004/0228869. These antibodies comprise complementarity determining regions (CDRs) that bind to an epitope of chemokine receptor 5 (CCR5). CCR5 is a chemokine receptor which binds members of the C—C group of chemokines, and whose amino acid sequence comprises that provided in Genbank Accession Number 1705896. The subject epitope comprises consecutive amino acid residues present in i) an N-terminus of CCR5, ii) one of three extracellular loop regions of CCR5, or iii) a combination of (i) and (ii).

Biologically active fragments, deletion variants, substitution variants or addition variants of any of the foregoing that maintain at least some degree of antiretroviral activity can also serve as an EI in accordance with the invention. EIs of the invention can be made recombinantly or using synthetic methods well known in the art.

The EIs of the invention can advantageously be modified, if necessary, to include one or more amino acid residues such as, for example, lysine, cysteine and/or arginine, in order to provide facile attachment of the polymer to an atom within the side chain of the amino acid. Techniques for adding amino acid residues are well known to those of ordinary skill in the art. Reference is made to J. March, Advanced Organic Chemistry: Reactions Mechanisms and Structure, $4^{th}$ Edition.

Preferred sites on a peptidyl EI for covalent attachment of a water soluble polymer include the N- or C-termini, the amino group of lysine, hydroxyl groups present on tyrosine, threonine, or serine, and the sulhydryl group of cysteine.

Preparing an EI

Any of the above entry inhibitors can be prepared using one or more of the following synthetic approaches well known in the art for the synthesis and preparation of polypeptides in general. For example, an EI may be synthesized using conventional stepwise solution or solid phase synthesis, fragment condensation, F-MOC or T-BOC chemistry, e.g., as described in *Chemical Approaches to the Synthesis of Peptides and Proteins*, William et al., Eds., 1997, CRC Press, Boca Raton Fla., and in references cited therein; in *Solid Phase Peptide Synthesis: A Practical Approach*, Atherson & Sheppard, Eds., 1989, IRL Press, Oxford, England, and in Sheppard, R. C. et al., *J. Chem. Soc. Chem. Comm*., pp. 165-166 (1985)), using, for example, an Advanced Chemtech model 200 available from Advanced Chemtech., Louisville, Ky., a Millipore 9050+ available from Millipore, Bedford Mass., or other available instrumentation.

Alternatively, the EI compounds of the invention may be recombinantly engineered by incorporating cDNA coding sequences into functional viral or circular plasmid DNA vectors. The vectors or plasmids are then used to transfect or transform selected microorganisms. The transformed or transfected microorganisms are cultured under conditions that are conducive to express vector-borne DNA sequences, followed by isolation of the desired peptides from the growth medium. See, for example U.S. Pat. No. 5,955,422. Vectors that may be used include those derived from recombinant bacteriophage DNA, plasmid DNA or cosmid DNA. For example, plasmid vectors such as pcDNA3, pBR322, pUC 19/18, pUC 118, 119 and M13 mp series of vectors may be used. Bacteriophage vectors include λgt10, λgt11, λgt18-23, λZAP/R and the EMBL series of bacteriophage vectors. Cosmid vectors that may be utilized include, but are not limited to, pJB8, pCV 103, pCV 107, pCV 108, pTM, pMCS, and pNNI.

Recombinant viral vectors may also be used including those derived from herpes virus, retroviruses, vaccinia viruses, adenoviruses, or baculovirus.

The EI compounds of the invention may also be prepared using standard recombinant DNA technology techniques that are well known in the art, such as those described in Sambrook, et al., *Molecular Cloning: A Laboratory Manual, 2nd edition*, (Cold Spring Harbor Press, Cold Spring Harbor, N.Y.) or in Ausubel et al., *Current Protocols in Molecular Biology*, both of which are herein incorporated by reference. Illustrative methods for preparing T-1249 and T-20 are described in U.S. Pat. No. 6,767,993, U.S. Pat. No. 6,015,881 (T-20), U.S. Pat. No. 6,258,782 (T-1249), and in U.S. Pat. No. 6,348,568 (T-1249).

After cleavage and deprotection, a polypeptide EI may be purified, for example, by ion exchange chromatography, gel electrophoresis, affinity chromatography, size exclusion chromatography, precipitation, and the like. Alternatively, normal or reverse-phase HPLC may be employed to purify/separate full length polypeptides from smaller fragments.

Amino acid sequences of an entry inhibitor can be confirmed and identified using standard amino acid analysis, as well as manual or automated Edman degradation and determination of each amino acid, using for example, automated amino acid sequencers such as those manufactured by Applied Biosystems. Suitable automated sequencers include the Applied Biosystems 476A Protein Sequencer or the Procise 494 Protein Seuqencer. Both instruments use standard gas phase or pulsed liquid Edman degradation chemistry. HPLC analysis or mass spectrometry may also be used to confirm the identity of a given EI.

Humanized monoclonal antibodies such as PRO 140, PA 8, 9, 10, 11 or 12 are prepared as described in Olsen, W. C., et al., *J. of Virol., May* 1999, p. 4145-4155, Vol. 73, No. 5, and in U.S. Patent Application Publication No. 2004/0228869. Briefly, monoclonal antibodies such as these may be prepared from murine L1.2-CCR5$^{+}$ cells (Wu, L., et al., *Nature,* 384:179-183, 1996) using standard hybridoma techniques, coupled with techniques for making humanized antibodies. Illustrative publications describing how to produce humanized antibodies include U.S. Pat. No. 4,816,567, U.S. Pat. No. 5,225,539, U.S. Pat. No. 5,585,089, U.S. Pat. No. 5,693,761, and WO 90/07861.

PRO-542, a CD4-IgG2 chimeric heterotetramer, can be prepared using the techniques and expression vectors described in U.S. Pat. No. 6,451,313.

Additional entry inhibitors such as sulfated CCR4 peptides are prepared as described in U.S. Patent Application Publication No. 2003/0139571.

Polymers

As previously discussed, one aspect of the invention is directed to a conjugate of an EI, such as T-20 or T-1249 or the like (as described above) attached to a water-soluble polymer, often designated herein simply as POLY. With respect to the water-soluble polymer, the water-soluble polymer is nonpeptidic, nontoxic, non-naturally occurring and biocompatible. A substance is generally considered biocompatible if the beneficial effects associated with use of the substance alone or with another substance (e.g., active agent such an entry inhibitor) in connection with living tissues (e.g., administration to a patient) outweighs any deleterious effects as evaluated by a clinician, e.g., a physician. With respect to non-immunogenicity, a substance is considered nonimmunogenic if the intended use of the substance in vivo does not produce an undesired immune response (e.g., the formation of antibodies) or, if an immune response is produced, that such a response is not deemed clinically significant or important as evaluated by a clinician. It is particularly preferred that the water-soluble polymer of the invention is both biocompatible and nonimmunogenic.

Examples of such polymers include, but are not limited to, poly(alkylene glycols) such as polyethylene glycol (PEG), poly(propylene glycol) ("PPG"), copolymers of ethylene glycol and propylene glycol and the like, poly(oxyethylated polyol), poly(olefinic alcohol), poly(vinylpyrrolidone), poly(hydroxyalkylmethacrylamide), poly(hydroxyalkylmethacrylate), poly(saccharides), poly(o-hydroxy acid), poly(vinyl alcohol), polyphosphazene, polyoxazoline, poly(N-acryloylmorpholine), and combinations of any of the foregoing. A polymer of the invention may be a homopolymer, alternating copolymer, random copolymer, block copolymer, alternating tripolymer, random tripolymer, or a block tripolymer made up of monomers of any of the preceding polymers. Preferably, the polymer is a copolymer, or, more preferably, is a homopolymer, e.g., of polyethylene glycol. Although much of the discussion herein is focused upon PEG as an illustrative water-soluble polymer, the discussion and structures presented herein are meant to encompass any of the water-soluble polymers described above. More specifically, for exemplary structures and figures demonstrating "PEG" as the water-soluble polymer, the term "PEG" is also meant to be substituted with any of the alternative water-soluble polymers described herein, such that the structures and figures provided herein explicitly extend to such alternative water-soluble polymers.

The polymer per se, prior to conjugation to an EI, is typically characterized as having from 2 to about 300 termini, more preferably from about 2 to about 25 termini, even more preferably having 2, 3, 4, 5, 6, 7, 8, 9, or 10 termini.

The polymer is not limited to a particular structure and can be linear (e.g., end-capped PEG or linear bifunctional PEG), branched or multi-armed. Typically, PEG and other water-soluble polymers, prior to conjugation with an EI, are activated with a suitable activating group appropriate for coupling to a desired site on the EI. Representative polymeric reagents and methods for conjugating these polymers to an active moiety are known in the art and further described in Zalipsky, S., et al., "*Use of Functionalized Poly(Ethylene Glycols) for Modification of Polypeptides*" in Polyethylene Glycol Chemistry: Biotechnical and Biomedical Applications, J. M. Harris, Plenus Press, New York (1992), in Zalipsky (1995) *Advanced Drug Reviews* 16:157-182, in Roberts, M. et al., "*Chemistry for Peptide and Protein PEGylation*", Advanced Drug Delivery Reviews 54 (2002): 459-476, and in "*Nektar Advanced PEGylation: Polyethylene Glycol and Derivatives for Advanced PEGylation*", Catalog 2004.

Typically, the weight average molecular weight of the non-peptidic water soluble polymer in the conjugate is from about 100 Daltons to about 150,000 Daltons. Exemplary ranges, however, include weight-average molecular weights in the range of about 500 Daltons to about 100,000 Daltons, in the range of about 2,000 Daltons to about 90,000 Daltons, in the range of about 5,000 Daltons to about 85,000 Daltons, in the range of about 10,000 Daltons to about 50,000 Daltons, or in the range of about 15,000 Daltons to about 40,000 Daltons.

Higher molecular weight polymers, e.g., having a molecular weight greater of about 20,000 daltons or more, or 30,000 daltons or more, or even 40,000 daltons or more, or even 50,000 daltons or more, are preferred in the present instance when covalently attached to an EI by means of a hydrolyzable linkage. In one embodiment, use of a high molecular weight and/or branched degradable polymer is preferred, since due to spacial constraints on the polypeptidyl EI, it may be possible to covalently attach only one or two molecules of high molecular weight polymer to the EI. In this way, formation of a hydrolyzable, mono-polymer conjugate (i.e., having only one polymer molecule covalently attached to the EI) or di-polymer conjugate, is favored. This can advantageously lead to a higher yields, along with a cleaner conjugate synthesis and subsequent separation, purification, and characterization, due to the lack of formation of multiple conjugate species, although different PEG-mers (conjugates wherein the active agent has 1-, 2-, 3-, or more polymer chains covalently attached thereto) are separable as described in greater detail below. Moreover, when considering the action of the conjugate in-vivo, hydrolysis of a mono-polymer conjugate may be particularly advantageous, since only a single hydrolysis reaction is involved, i.e., a hydrolysis effective to release the EI and the polymer, in contrast to the degradable, covalent attachment of a polymer to multiple reactive sites upon the EI, or, alternatively, multiple EI drugs covalently attached to a multi-armed polyer, where release of the polymer or of the drug is complicated by the kinetics involved in multiple hydrolysis steps and intermediate species. Although the use of a degradable, larger molecular weight polymer may, in certain instances, offer certain advantages over alternative conjugate structures or architectures, that is not to say that alternative embodiments, such as the use of smaller polymers, either singly or multiply attached to an EI, or other additional embodiments as described herein, are without their own associated advantages, to be described in greater detail below.

Exemplary weight average molecular weights for the water-soluble polymer segment include about 100 Daltons, about 200 Daltons, about 300 Daltons, about 400 Daltons, about 500 Daltons, about 600 Daltons, about 700 Daltons, about 750 Daltons, about 800 Daltons, about 900 Daltons, about 1,000 Daltons, about 2,000 Daltons, about 2,200 Daltons, about 2,500 Daltons, about 3,000 Daltons, about 4,000 Daltons, about 4,400 Daltons, about 5,000 Daltons, about 6,000 Daltons, about 7,000 Daltons, about 7,500 Daltons, about 8,000 Daltons, about 9,000 Daltons, about 10,000 Daltons, about 11,000 Daltons, about 12,000 Daltons, about 13,000 Daltons, about 14,000 Daltons, about 15,000 Daltons, about 20,000 Daltons, about 22,500 Daltons, about 25,000 Daltons, about 30,000 Daltons, about 35,000 Daltons, about 40,000 Daltons, about 45,000 Daltons, about 50,000 Daltons, about 55,000 Daltons, about 60,000 Daltons, about 65,000 Daltons, about 70,000 Daltons, and about 75,000 Daltons. Branched or other multi-arm versions of the water-soluble polymer (e.g., a branched 40,000 Dalton water-soluble polymer having two 20,000 Dalton polymer 'arms') having a total molecular weight of any of the foregoing can also be used.

In instances in which the polymer is PEG, the PEG will typically comprise a number of $(OCH_2CH_2)$ monomers. As used throughout the description, the number of repeat units is identified by the subscript "n" in "$(OCH_2CH_2)_n$." Thus, the value of (n) typically falls within one or more of the following ranges: from 2 to about 3400, from about 100 to about 2,300, from about 100 to about 2,270, from about 136 to about 2,050, from about 225 to about 1,930, from about 450 to about 1,930, from about 1,200 to about 1,930, from about 568 to about 2727, from about 660 to about 2730, from about 795 to about 2730, from about 909 to about 2730, and from about 1,200 to about 1,900. For any given polymer in which the molecular weight is known, it is possible to determine the number of repeat units (i.e., "n") by dividing the total molecular weight of the polymer by the molecular weight of the repeat unit.

One particularly preferred polymer for use in the invention is an end-capped polymer, that is, a polymer having at least one terminus capped with a relatively inert group, such as a lower $C_{1-6}$ alkoxy group or a benzyloxy group, although a hydroxyl group can also be used. When the polymer is PEG, for example, it is preferred in many instances to use a methoxy-PEG (commonly referred to as mPEG), which is a form of PEG, typically linear, wherein one terminus of the polymer is a methoxy ($-OCH_3$) group, while the other terminus is a hydroxyl or other functional group that can be optionally chemically modified.

The structure of an mPEG is given below.
$CH_3O-(CH_2CH_2O)_n-CH_2CH_2-$, where the value of (n) is as described above.

Alternatively, rather than being end-capped, a polymer reactant (and corresponding product) may possess a dumbbell-like or bifunctional linear structure, such that the resulting conjugate is one in which the EIs are interconnected by a central linear POLY, e.g., PEG. More specifically, in one embodiment, such a conjugate is represented by the structure EI-PEG-EI, where the EIs may be the same or different. That is to say, each independent EI is selected from the group consisting of: T-20, T-1249, PRO 542, PRO-140, PA 8, PA 9, PA 10, PA 11, PA 12, PRO-367, SCH-417690, TXN-355, UK-427, UK-857, GSK-873, and GSK-140. Preferably, a conjugate of the invention is one where the polymer, POLY, is covalently attached to an EI selected from the group consisting of T-20, T-1249, PRO-542 and PRO-140. In situations in which combination therapy is advantageous, for example, when combination therapy is useful in preventing HIV-resistance, or when a synergistic effect exists, conjugates comprising two different EI drugs covalently attached to a polymer represent a preferred embodiment. For example, T-20, in combination with PRO 542 and PRO 140, acts synergistically to block infection of healthy cells (4th Annual Fortis Bank Biotechnology Conference, London, May 4, 2004). Thus, exemplary embodiments in accordance with this aspect of the invention include a dumbbell polymer structure having T-20 and PRO-542 attached to opposite termini, or T-20 and PRO-140 attached at opposite termini, or PRO-542 and PRO 140 attached at opposite termini, with the third EI simply being co-administered therewith. In yet another embodiment, a three-arm polymer architecture is employed, with one of the three EI drugs each covalently attached to each of the polymer arms. In yet a further embodiment, a conjugate in accordance with the invention possesses a dumbbell structure with T-20 at one polymer terminus and T-1249 at the other terminus. In yet another embodiment, the linear bifunctional conjugate possesses the structure EI-POLY-A, where A in its broadest sense represents a functional group suitable for attachment to another moiety. Preferably, A is a retroviral agent, and most preferably, is an anti-HIV agent that works in a synergistic fashion with EI.

A polymer for use in the invention may possess 2 arms, 3 arms, 4 arms, 5 arms, 6 arms, 7 arms, 8 arms or more. Multi-armed polymers can be used to form conjugates, or alternatively, can be used to form hydrogels, and may possess anywhere from 2 to 300 or so reactive termini.

In one embodiment of the invention, preferred are branched polymer segments having 2 or 3 polymer arms. An illustrative branched POLY, as described in U.S. Pat. No. 5,932,462, corresponds to the structure:

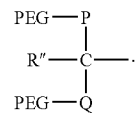

In this representation, R" is a nonreactive moiety, such as H, methyl or a PEG, and P and Q are nonreactive linkages. In the above particular branched configuration, the branched polymer segment possesses a single reactive site extending from the "C" branch point for positioning of the EI, optionally via a linker, which may optionally include a degradable linkage.

In an illustrative embodiment, the branched PEG polymer segment is methoxy poly(ethylene glycol) disubstituted lysine with a single attachment site for covalent attachment to an EI. Depending upon the site of attachment on the EI, the reactive ester group of the disubstituted lysine may be further modified or activated to form a functional group suitable for reaction with a target group on the EI drug.

Branched PEGs having the above-described generalized structure for use in the present invention will typically have fewer than 4 PEG arms, and more preferably, will have 2 or 3 PEG arms. Such branched PEGs offer the advantage of having a single reactive site, coupled with a larger, more dense polymer cloud than their linear PEG counterparts. One particular type of branched PEG EI conjugate corresponds to the structure: $(MeO-PEG-)_iG-$, where i equals 2 or 3, and G is a lysine or other suitable amino acid residue, with a site suitable for attachment to an EI.

Additional branched PEGs for use in the present invention include those described in International Patent Application Publication No. WO 2005/000360. For instance, an additional branched polymer for preparing an EI conjugate possesses the structure below,

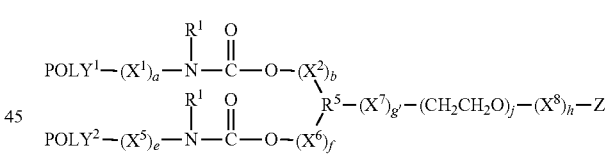

where $POLY^1$ is a water-soluble polymer; $POLY^2$ is a water-soluble polymer; (a) is 0, 1, 2 or 3; (b)iso, 1, 2 or 3; (e)iso, 1, 2 or 3; (f) is 0, 1, 2 or 3; (g)iso, 1, 2 or 3; (h) is 0, 1, 2 or 3; (j) is 0 to 20; each $R^1$ is independently H or an organic radical selected from the group consisting of alkyl, substituted alkyl, alkenyl, substituted alkenyl, alkynyl, substituted alkynyl, aryl and substituted aryl; $X^1$, when present, is a first spacer moiety; $X^2$, when present, is a second spacer moiety; $X^5$, when present, is a fifth spacer moiety; $X^6$, when present, is a sixth spacer moiety; $X^7$, when present, is a seventh spacer moiety; $X^8$, when present, is an eighth spacer moiety; $R^5$ is a branching moiety; and Z is a reactive group for coupling to an EI, optionally via an intervening spacer. Preferably, $POLY^1$ and $POLY^2$ in the preceding branched polymer structure are identical, i.e., are of the same polymer type (structure) and molecular weight.

A representative branched polymer falling into the above classification, suitable for use in the present invention is:

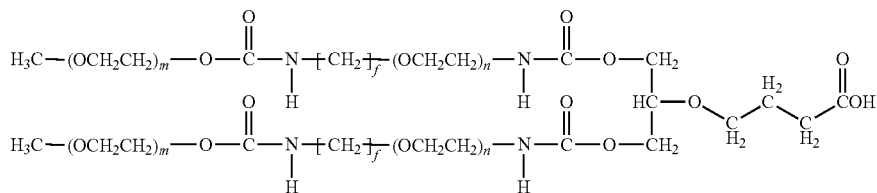

10 where (m) is 2 to 4000, and (f) is 0 to 6 and (n) is 0 to 20.

Branched polymers useful in preparing a conjugate or hydrogel of the invention additionally include those represented more generally by the formula $R(POLY)_y$, where R is a central or core molecule from which extends 2 or more POLY arms such as PEG. The variable y represents the number of POLY arms, where each of the polymer arms can independently be end-capped or alternatively, possess a reactive functional group at its terminus. A more explicit structure in accordance with this embodiment of the invention possesses the structure, $R(POLY-Z)_y$, where each Z is independently an end-capping group, or a reactive group, e.g., suitable for reaction with a cross-linker or with an EI. In yet a further embodiment when Z is a reactive group, upon reaction with, e.g., either a cross-linker or an EI, the resulting linkage can be hydrolytically stable, or alternatively, may be degradable, i.e., hydrolyzable. Typically, at least one polymer arm possesses a terminal functional group suitable for reaction with an EI. Branched PEGs such as those represented generally by the formula, $R(PEG)_y$, above possess 2 polymer arms to about 300 polymer arms (i.e., y ranges from 2 to about 300). Preferably, such branched PEGs possess from 2 to about 25 polymer arms, more preferably from 2 to about 20 polymer arms, and even more preferably from 2 to about 15 polymer, or from 3 to about 15 polymer arms or fewer. Most preferred are multi-armed polymers having 3, 4, 5, 6, 7 or 8 arms.

Preferred core molecules in branched PEGs as described above are polyols, which are then further functionalized. Such polyols include aliphatic polyols having from 1 to 10 carbon atoms and from 1 to 10 hydroxyl groups, including ethylene glycol, alkane diols, alkyl glycols, alkylidene alkyl diols, alkyl cycloalkane diols, 1,5-decalindiol, 4,8-bis(hydroxymethyl)tricyclodecane, cycloalkylidene diols, dihydroxyalkanes, trihydroxyalkanes, and the like. Cycloaliphatic polyols may also be employed, including straight chained or closed-ring sugars and sugar alcohols, such as mannitol, sorbitol, inositol, xylitol, quebrachitol, threitol, arabitol, erythritol, adonitol, ducitol, facose, ribose, arabinose, xylose, lyxose, rhamnose, galactose, glucose, fructose, sorbose, mannose, pyranose, altrose, talose, tagitose, pyranosides, sucrose, lactose, maltose, and the like. Additional aliphatic polyols include derivatives of glyceraldehyde, glucose, ribose, mannose, galactose, and related stereoisomers. Other core polyols that may be used include crown ether, cyclodextrins, dextrins and other carbohydrates such as starches and amylose. Preferred polyols include glycerol, pentaerythritol, sorbitol, and trimethylolpropane.

A representative multi-arm structure corresponding to a multi-armed polymer conjugate of the invention is shown below, where y preferably ranges from about 3 to about 8, R is as defined above, and L is a linker that covalently attaches each polymer arm to the EI, optionally via a hydrolyzable linkage. As will be described in more detail in the linker section below, although any of a number of linkages can be used to covalently attach a polymer or polymer arm to an EI, in certain instances, the linkage is preferably degradable, designated herein as $L_D$, that is to say, contains at least one bond or moiety that hydrolyzes under physiological conditions, e.g., an ester, hydrolyzable carbamate, carbonate, or other such group.

$$R-(-POLY-L-EI)_y$$

Additional multi-arm polymers useful for forming a multi-arm EI-conjugate or hydrogel of the invention include multi-arm PEGs available from Nektar (Huntsville, Ala.). Preferred multi-armed activated polymers for use in the method of the invention correspond to the following structure, where E represents a reactive group suitable for coupling to an EI. In one embodiment, E is preferably an —OH (for reaction with an EI carboxy group or equivalent), a carboxylic acid or equivalent, or a carbonic acid (for reaction with EI —OH groups), or an amino group (for reaction with a C-terminal).

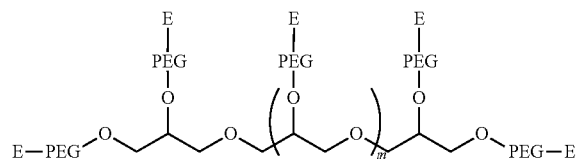

PEG is $-(CH_2CH_2O)_nCH_2CH_2-$, and m is selected from the group consisting of 3, 4, 5, 6, 7, and 8. Of course, the corresponding EI polymer conjugate product possesses the structure shown above with the exception that the reactive group, E, is replaced by "-L-EI", where L represents a linkage formed by reaction of E and a reactive group present on the EI. As discussed previously, in certain embodiments, preferred linkages are ester, carboxyl and hydrolyzable, carbamate, such that the polymer-portion of the conjugate is hydrolyzed in vivo to release the EI and the polymer. In such instances, the linker L is designated as $L_D$.

Alternatively, the polymer conjugate may possess an overall forked structure. An example of a forked PEG corresponds to the following generalized structure, where the first structure represents an activated forked PEG and the second structure represents a forked EI polymer conjugate:

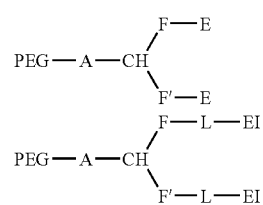

where PEG is any of the forms of PEG described herein, E is a reactive group suitable for covalent coupling with an EI, A is a linking group, preferably a hydrolytically stable linkage such as oxygen, sulfur, or —C(O)—NH—, F and F' are hydrolytically stable spacer groups that are optionally present, and L is as defined above. In a preferred embodiment, the linker L contains at least one hydrolyzable functional group. In the conjugate structure to the right, the EIs can be the same or different. As in the previous embodiment, although not shown explicitly, also contemplated is a forked structure where one of the EIs is replaced by another retroviral or anti-HIV agent. Exemplary linkers and spacer groups corresponding to A, F and F' are described in U.S. Pat. No. 6,362,254, and are useful in forming polymer conjugates in accordance with the present invention. F and F' are spacer groups that may be the same of different. In one particular embodiment of the above, PEG is mPEG, A corresponds to —C(O)—NH—, and F and F' are both methylene or —CH$_2$—. This type of polymer segment is useful for reaction with two active agents, where the two active agents are positioned at a precise or predetermined distance apart, depending upon the selection of F and F'.

In any of the representative structures provided herein, one or more degradable linkages may additionally be contained in the polymer segment, POLY, to allow generation in vivo of a conjugate having a smaller PEG chain than in the initially administered conjugate. Appropriate physiologically cleavable linkages include but are not limited to ester, carbonate ester, carbamate, sulfate, phosphate, acyloxyalkyl ether, acetal, and ketal. Such linkages when contained in a given polymer segment will preferably be stable upon storage and upon initial administration.

More particularly, as described generally above, two or more polymer segments connected by a hydrolyzable linkage may be represented by the following structure: PEG1-W-PEG2 (where PEG1 and PEG2 can be the same or different) and W represents a weak, hydrolyzable linkage. These polymer structures contain PEG segments that are removable (i.e., cleavable) in-vivo, as described in detail in U.S. Patent Application Publication No. U.S. 2002/0082345.

The PEG polymer used to prepare a conjugate of the invention may comprise a pendant PEG molecule having reactive groups, such as carboxyl, covalently attached along the length of the PEG rather than at the end of the PEG chain(s). The pendant reactive groups can be attached to the PEG directly or through a spacer moiety, such as an alkylene group.

Additional representative PEGs having either linear or branched structures for use in preparing the conjugates of the invention may be purchased from Nektar Therapeutics (formerly Shearwater Corporation, Huntsville, Ala.). Illustrative structures are described in Nektar's 2004 catalogue, the contents of which is expressly incorporated herein by reference.

Hydrolytically degradable linkages, useful not only as a degradable linkage within a polymer backbone, but preferably in the case of the instant invention, for covalently attaching a polymer to an EI, include: carbonate; imine resulting, for example, from reaction of an amine and an aldehyde (see, e.g., Ouchi et al. (1997) *Polymer Preprints* 38(1):582-3); phosphate ester, formed, for example, by reacting an alcohol with a phosphate group; hydrazone, e.g., formed by reaction of a hydrazide and an aldehyde; acetal, e.g., formed by reaction of an aldehyde and an alcohol; orthoester, formed, for example, by reaction between a formate and an alcohol; and certain urethane linkages.

Additional PEG reagents for use in the invention include hydrolyzable PEGs and linkers such as those described in International Patent Application Publication No. WO 04/089280. In utilizing this approach, one or more of the free functional groups within an EI as described herein, e.g., amino, hydroxyl, mercapto, phosphate and/or carboxy group, is derivatized with a group sensitive to mild basic conditions, e.g., 9-fluorenylmethoxycarbonyl (Fmoc) or 2-sulfo-9-fluorenylmethoxycarbonyl (FMS), that is covalently attached to a polymer segment such as a PEG moiety. In the resulting conjugate, the EI and the polymer are each covalently attached to different positions of the scaffold Fmoc or FMS structure, and are releasable under physiological conditions.

Such optional features of the polymer conjugate, i.e., the introduction of one or more degradable linkages into the polymer chain, may provide for additional control over the final desired pharmacological properties of the conjugate upon administration. For example, a large and relatively inactive conjugate (i.e., having one or more high molecular weight PEG chains attached thereto, for example, one or more PEG chains having a molecular weight greater than about 10,000, wherein the conjugate possesses essentially no or insignificant bioactivity) may be administered, which is hydrolyzed to generate a bioactive EI conjugate possessing a portion of the original PEG chain. Alternatively, if a degradable linkage is used to covalently attach the EI to the polymer, hydrolysis results in the original EI absent the polymer segment, or alternatively, a modified EI drug possessing a short tag portion left over from hydrolysis of the polymer segment, where the modified EI still retains its HIV-entry inhibitor property. In this way, the properties of the conjugate can be more effectively tailored to balance the pharmacological properties of the conjugate upon administration.

Those of ordinary skill in the art will recognize that the foregoing discussion concerning substantially water-soluble polymer segments is by no means exhaustive and is merely illustrative, and that all polymeric materials having the qualities described above are contemplated. As used herein, the term "polymeric reagent" generally refers to an entire molecule, which can comprise a water-soluble polymer segment and a functional group.

The Linkage and Exemplary EI Conjugates

As described above, a conjugate of the invention comprises a water-soluble polymer, POLY, covalently attached to an EI. Typically, for any given conjugate, there will be one to about four water-soluble polymers covalently attached to the EI, where the polymer may possess any of the forms described herein. In a preferred embodiment, the EI possesses 1 or 2 polymers covalently attached thereto.

The particular linkage covalently attaching the EI to the polymer depends on a number of factors. Such factors include, for example, the particular linkage chemistry employed, the particular EI, the available functional groups for covalent attachment within the EI, the potential presence of additional reactive functional groups within the EI that may optionally require protecting groups, and the like.

The conjugates of the invention can be, although are not necessarily, prodrugs, meaning that the linkage between the polymer and the EI is hydrolytically degradable to allow release of the EI moiety. Such linkages can be readily prepared by appropriate modification of either the peptidyl EI (e.g., the carboxyl group C terminus of the protein or a side chain hydroxyl group of an amino acid such as serine or threonine contained within the protein) and/or the polymeric reagent, using coupling methods commonly employed in the art combined with the teachings of the present application. Most preferred, however, are hydrolyzable linkages that are formed by reaction of a suitably activated polymer with a non-modified functional group contained within the EI, optionally via an intervening linker.

Alternatively, a hydrolytically stable linkage, such as an amide, urethane (also known as carbamate), amine, thioether (also known as sulfide), or urea (also known as carbamide) linkage can also be employed as the linkage for coupling the EI. One preferred hydrolytically stable linkage is an amide.

The conjugates (as opposed to an unconjugated EI) may or may not possess a measurable degree of retroviral activity, depending upon whether the polymer is covalently attached via a degradable or a hydrolytically stable linker. That is to say, a polymer conjugate in accordance with the invention will possesses anywhere from about 0.1% to about 100% or more of the anti-HIV activity of the unmodified parent EI. Preferably, conjugates possessing little or no activity contain a hydrolyzable linkage connecting the polymer to the EI, so that regardless of the lack of activity in the conjugate, the active EI (or a derivative thereof) is released upon aqueous-induced cleavage of the hydrolyzable linkage.

For conjugates possessing a hydrolytically stable linkage that couples the EI to the polymer, the conjugate will typically possess a measurable degree of antiviral activity. For instance, such polymer conjugates are typically characterized as having an activity of at least about 2%, 5%, 10%, 15%, 25%, 30%, 40%, 50%, 60%, 80%, 85%, 90%, 95% 97%, 100%, or more relative to that of the unmodified parent EI, when measured in a suitable model, such as those well known in the art. Preferably, conjugates having a hydrolytically stable linkage (e.g., an amide linkage) will possess at least some degree of the bioactivity of the unmodified parent EI.

Exemplary polymer conjugates in accordance with the invention will now be described.

There are a number of examples of suitable water-soluble polymeric reagents useful for forming covalent linkages with reactive amino groups contained within the EI. Particular examples, along with the corresponding conjugate, are provided in Table 1, below. In the table, the variable (n) represents the number of repeating monomeric units and "—NH-EI" represents the EI following conjugation to the water-soluble polymer, where the "NH—" represents an amino group on the EI. While each polymeric portion presented in Table 1 terminates in a "CH$_3$" group, other groups (such as H, ethyl and benzyl) can be substituted therefor. Moreover, although the tables herein generally show a single polymer reagent attached to an EI drug, this is for illustrative purposes only. It is to be understood that a given polymer reagent may be covalently attached to multiple sites upon the EI, depending upon the reactive groups employed, synthetic strategy, size of the polymer, etc. For the sake of simplicity, the illustrative structures in the tables below show one polymer reagent covalently attached to one site on the EI, although such structures are meant to additionally encompass the subject polymer reagent covalently attached to more than one site.

Additionally, any of the polymer conjugates in Table 1, if not degradable as shown, can be modified to form a conjugate comprising a degradable linkage as follows. For instance, a bifunctional spacer, preferably one that can be releasably attached to an EI, e.g., an amino acid, is covalently attached to a reactive site on the EI. Preferably, the bifunctional spacer possesses at one end an amino group, such that reaction with the exemplary polymer reagents in Table 1 is readily promoted. At the other end of the bifunctional spacer is, for example, a carboxyl group effective to form a hydrolyzable ester upon reaction with one or more hydroxyl groups present on the EI compound, such that upon hydrolysis, the polymer and spacer are cleaved, resulting in release of the parent EI drug.

TABLE 1

AMINE-SELECTIVE POLYMER REAGENTS AND THEIR RESPECTIVE EI CONJUGATES

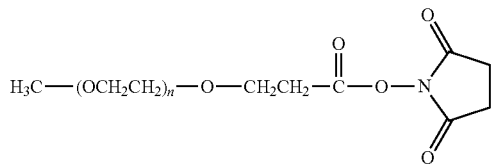

mPEG-Succinimidyl Derivative

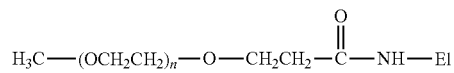

Amide Linkage,
Structure 1-1

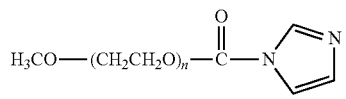

mPEG-Oxycarbonylimidazole Derivative

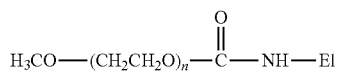

Carbamate Linkage,
Structure 1-2

TABLE 1-continued

AMINE-SELECTIVE POLYMER REAGENTS AND THEIR RESPECTIVE El CONJUGATES

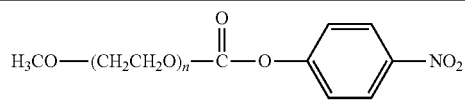

mPEG Nitrophenyl Derivative

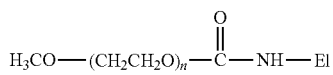

Carbamate Linkage,
Structure 1-3

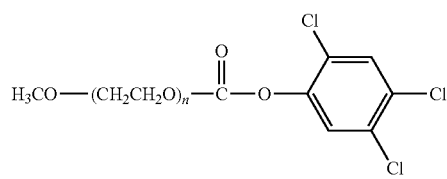

mPEG-Trichlorophenyl Carbonates

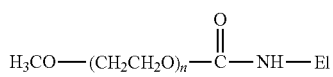

Carbamate Linkage
Structure 1-4

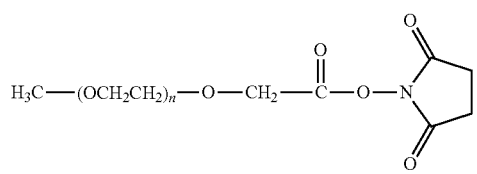

mPEG-Succinimidyl Derivative

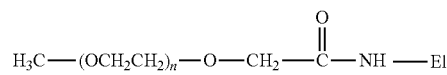

Amide Linkage
Structure 1-5

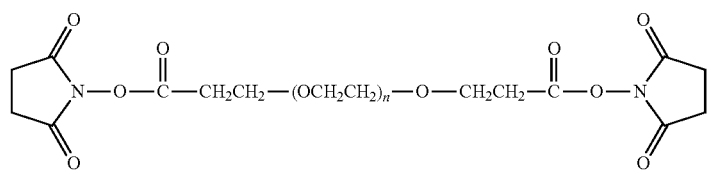

Homobifunctional PEG-Succinimidyl Derivative

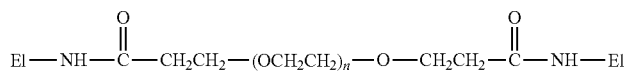

Amide Linkages
Structure 1-6

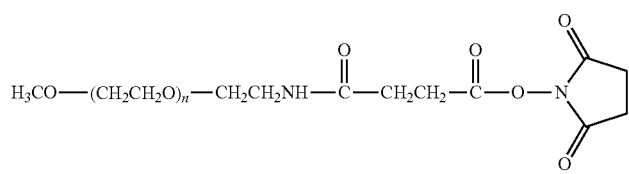

mPEG-Succinimdyl Derivative

TABLE 1-continued
AMINE-SELECTIVE POLYMER REAGENTS AND THEIR RESPECTIVE El CONJUGATES
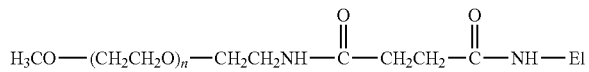
Amide Linkage
Structure 1-7
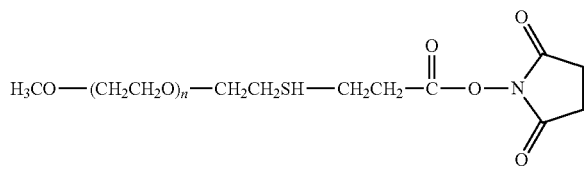
mPEG Succinimidyl Derivative
Amide Linkage
Structure 1-8
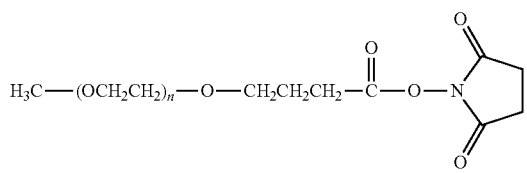
mPEG-Succinimidyl Derivative
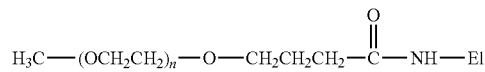
Amide Linkage
Structure 1-9
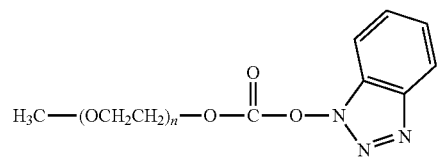
mPEG-Benzotriazole Carbonate Derivative
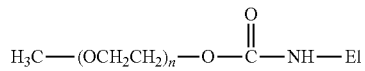
Carbamate Linkage
Structure 1-10
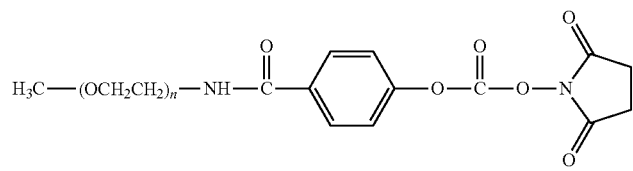
mPEG-Succinimidyl Derivative TABLE 1-continued
AMINE-SELECTIVE POLYMER REAGENTS AND THEIR RESPECTIVE El CONJUGATES
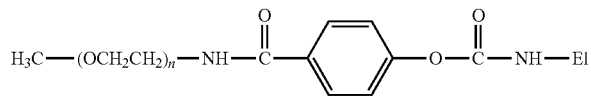
Carbamate Linkage
Structure 1-11
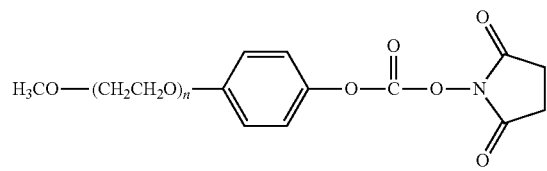
mPEG-Succinimidyl Derivative
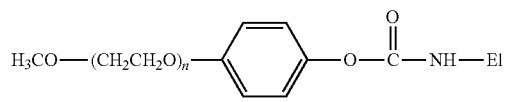
Amide Linkage
Structure 1-12
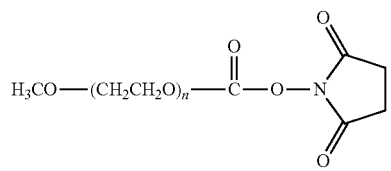
mPEG Succinimidyl Derivative
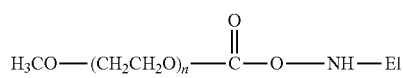
Amide Linkage
Structure 1-13
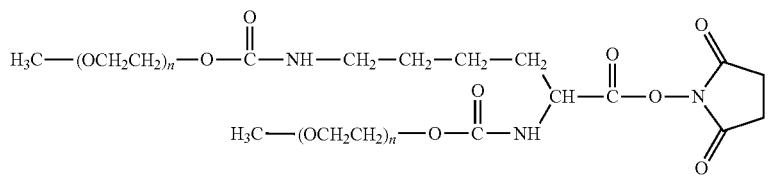
Branched mPEG2-N-Hydroxysuccinimide Derivative
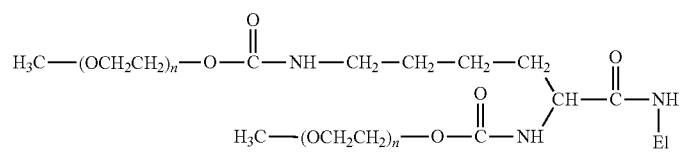
Amide Linkage
Structure 1-14
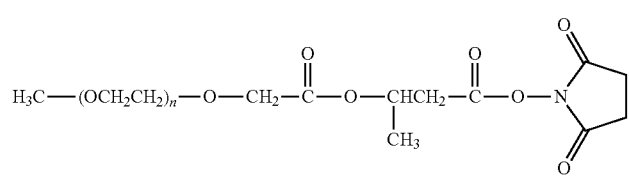
mPEG-Succinimidyl Derivative TABLE 1-continued AMINE-SELECTIVE POLYMER REAGENTS AND THEIR RESPECTIVE El CONJUGATES

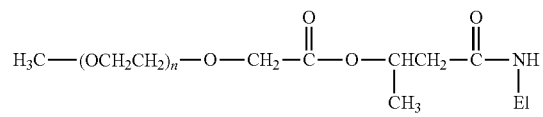

Amide Linkage
Structure 1-15

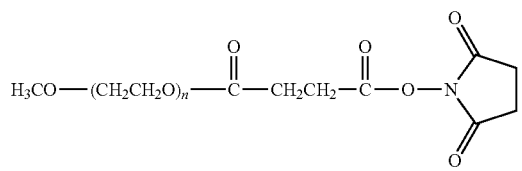

mPEG-Succinimidyl Derivative

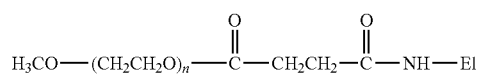

Amide Linkages
Structure 1-16

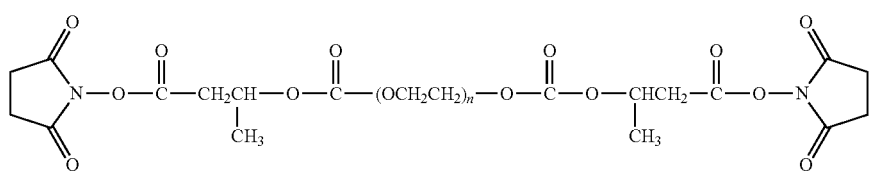

Homobifunctional PEG-Succinimidyl Derivative

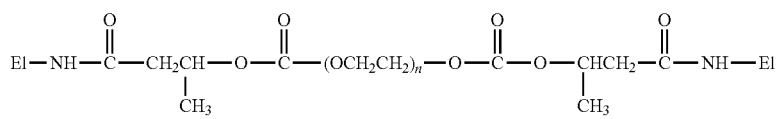

Amide Linkages
Structure 1-17

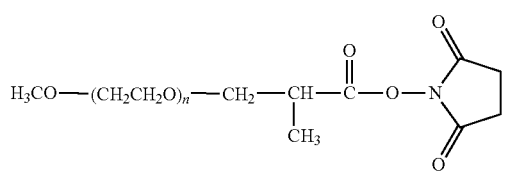

mPEG-Succinimidyl Derivative

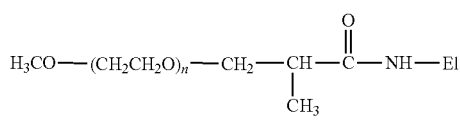

Amide Linkage
Structure 1-18

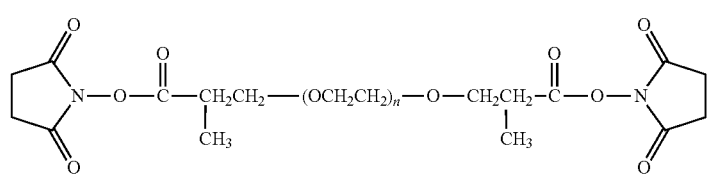

Homobifunctional PEG-Succinimidyl Propionate Derivative

TABLE 1-continued
AMINE-SELECTIVE POLYMER REAGENTS AND THEIR RESPECTIVE EI CONJUGATES
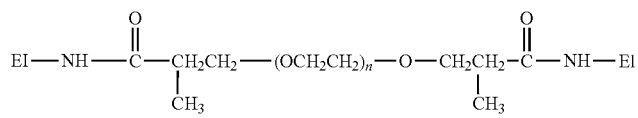
Amide Linkages
Structure 1-19
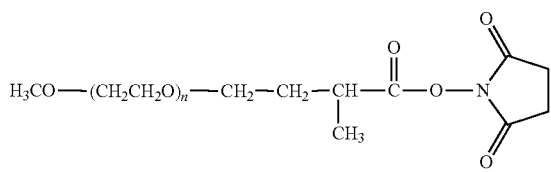
mPEG-Succinimidyl Derivative
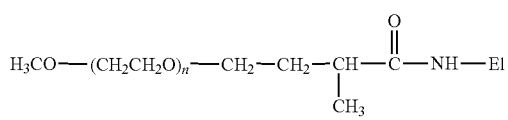
Amide Linkage
Structure 1-20
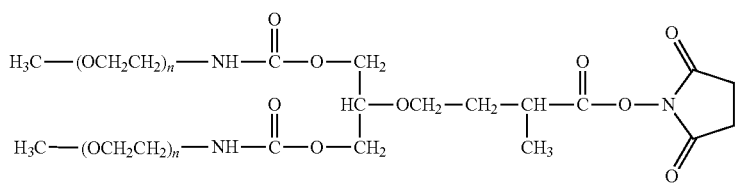
Branched mPEG2-N-Hydroxysuccinimide Derivative
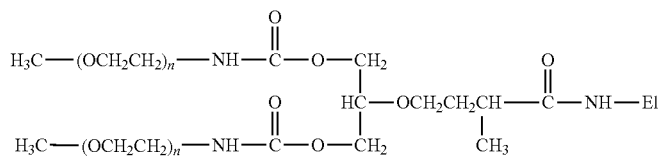
Amide Linkage
Structure 1-21
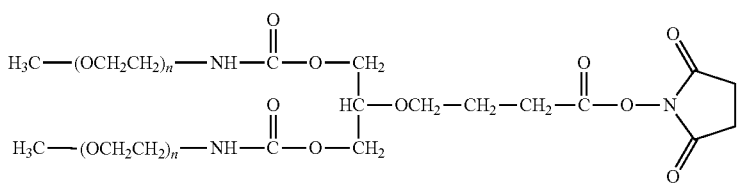
Branched mPEG2-N-Hydroxysuccinimide Derivative
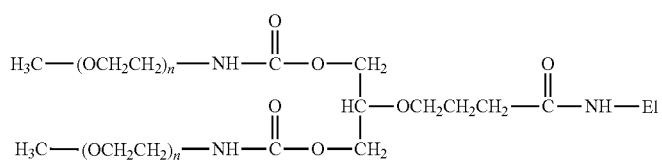
Amide Linkage
Structure 1-22

TABLE 1-continued

AMINE-SELECTIVE POLYMER REAGENTS AND THEIR RESPECTIVE El CONJUGATES

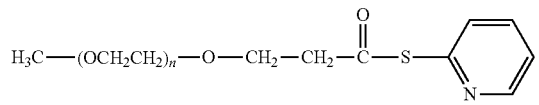

mPEG-Thioester Derivative

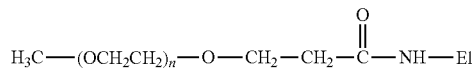

Amide Linkage (typically to El moiety having an N-terminal
cysteine or histidine)
Structure 1-23

Homobifunctional PEG Propionaldehyde Derivative

Secondary Amine Linkages
Structure 1-24

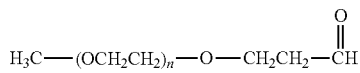

mPEG Propionaldehyde Derivative

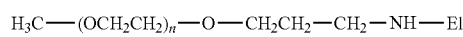

Secondary Amine Linkage
Structure 1-25

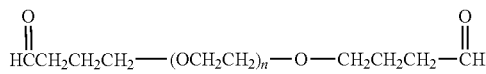

Homobifunctional PEG Butyraldehye Derivative

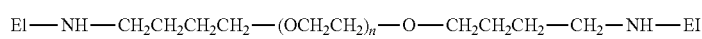

Secondary Amine Linkage
Structure 1-26

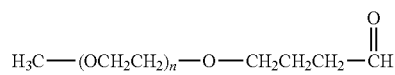

mPEG Butryaldehyde Derivative

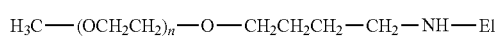

Secondary Amine Linkage
Structure 1-27

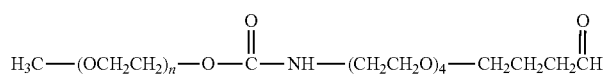

mPEG Butryaldehyde Derivative

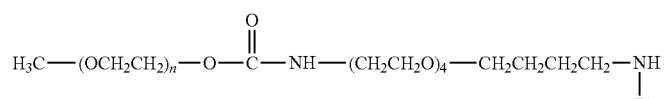

Secondary Amine Linkage
Structure 1-28

TABLE 1-continued

AMINE-SELECTIVE POLYMER REAGENTS AND THEIR RESPECTIVE E1 CONJUGATES

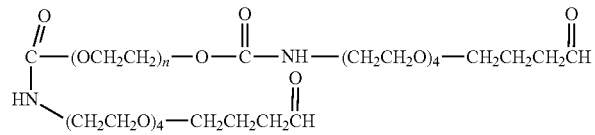

Homobifunctional PEG Butyraldehyde Derivative

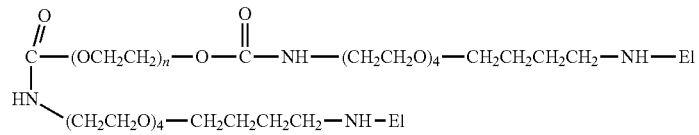

Secondary Amine Linkages
Structure 1-29

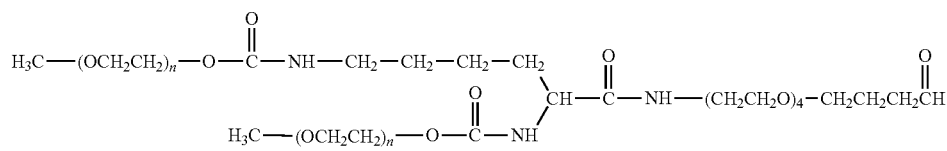

Branched mPEG2 Butyraldehyde Derivative

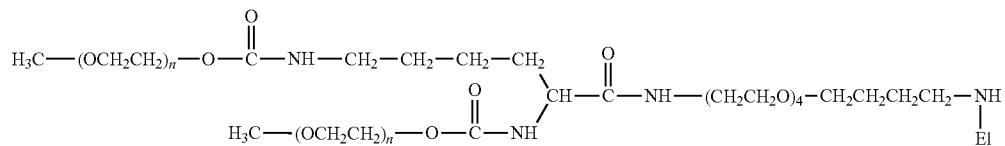

Secondary Amine Linkage
Structure 1-30

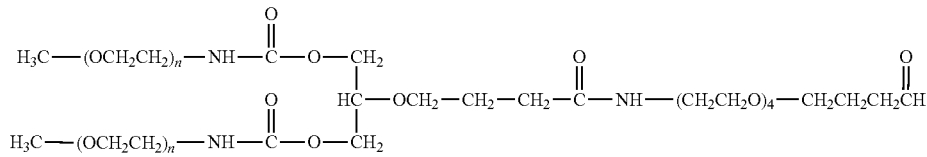

Branched mPEG2 Butyraldehyde Derivative

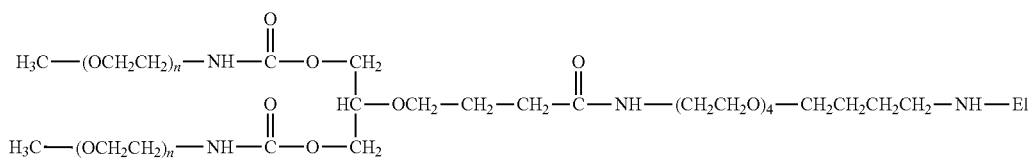

Secondary Amine Linkage
Structure 1-31

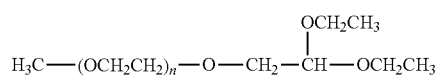

mPEG Acetal Derivative

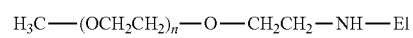

Secondary Amine Linkage
Structure 1-32

TABLE 1-continued

AMINE-SELECTIVE POLYMER REAGENTS AND THEIR RESPECTIVE El CONJUGATES

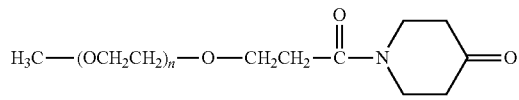

mPEG Piperidone Derivative

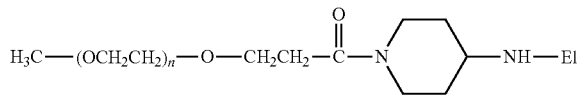

Secondary Amine Linkage
(to a secondary carbon)
Structure 1-33

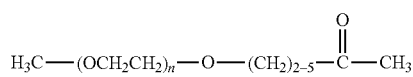

mPEG Methylketone Derivative

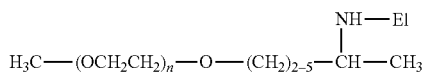

secondary amine linkage
(to a secondary carbon)
Structure 1-34

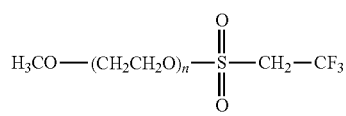

mPEG tresylate

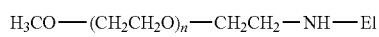

Secondary Amine Linkage
Structure 1-35

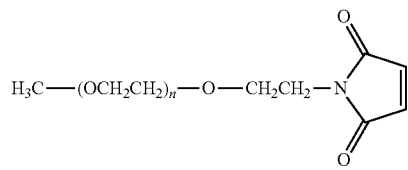

mPEG Maleimide Derivative
(under certain reaction conditions such as pH > 8)

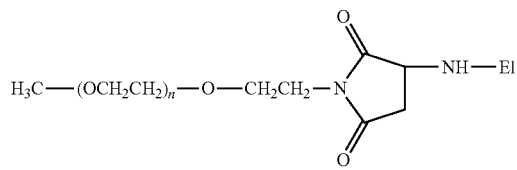

Secondary Amine Linkage
Structure 1-36

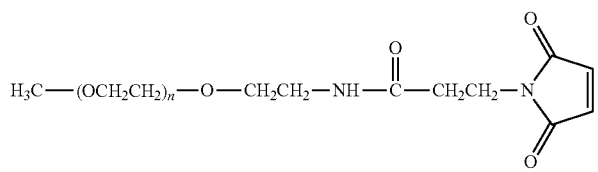

mPEG Maleimide Derivative
(under certain reaction conditions such as pH > 8)

TABLE 1-continued
AMINE-SELECTIVE POLYMER REAGENTS AND THEIR RESPECTIVE El CONJUGATES
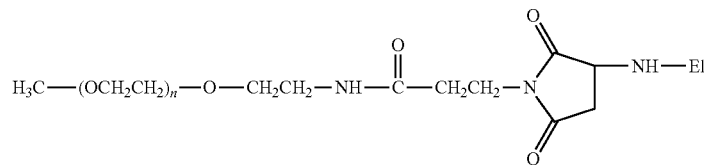
Secondary Amine Linkage
Structure 1-37
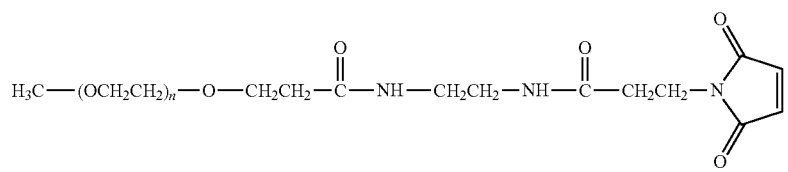
mPEG Maleimide Derivative
(under certain reaction conditions such as pH > 8)
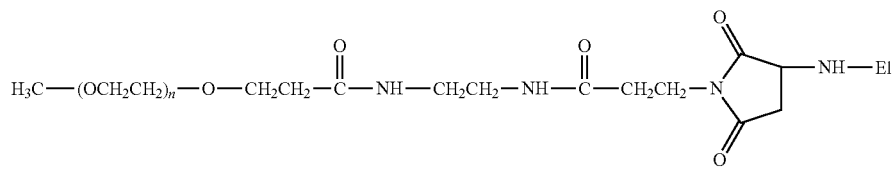
Secondary Amine Linkage
Structure 1-38
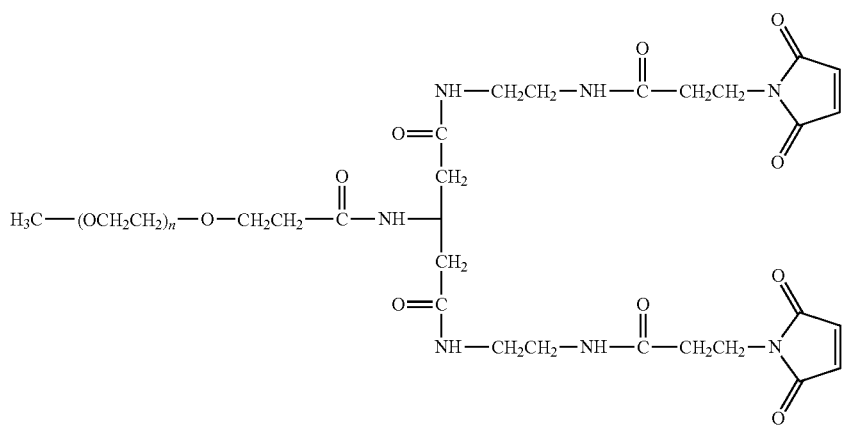
mPEG Forked Maleimide Derivative
(under certain reaction conditions such as pH > 8)

TABLE 1-continued
AMINE-SELECTIVE POLYMER REAGENTS AND THEIR RESPECTIVE El CONJUGATES
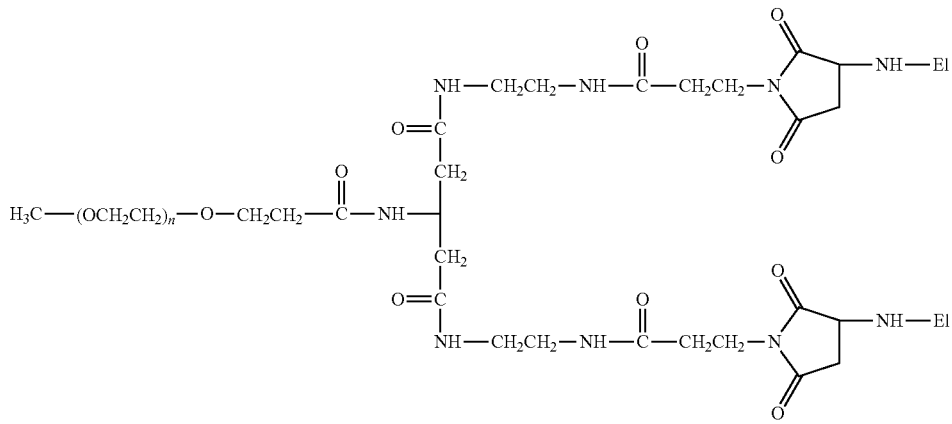
Secondary Amine Linkages
Structure 1-39
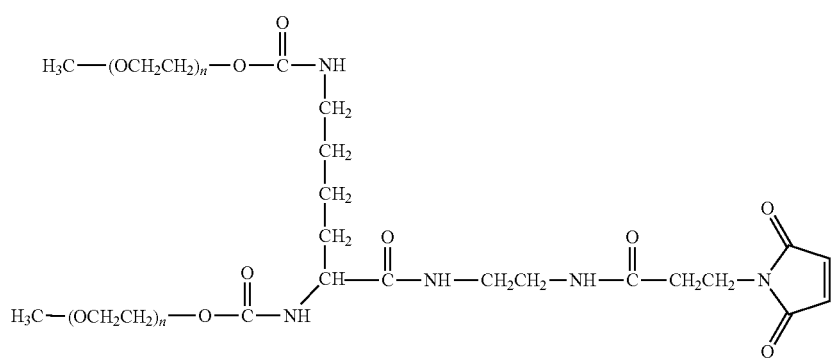
branched mPEG2 Maleimide Derivative
(under certain reaction conditions such as pH > 8)
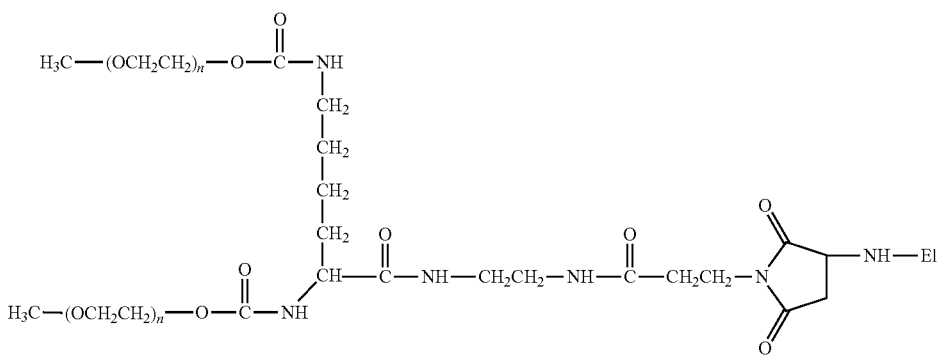
Secondary Amine Linkage
Structure 1-40

In one preferred embodiment of the invention, a conjugate is provided having the following structure, where the conjugate is a prodrug of an EI:

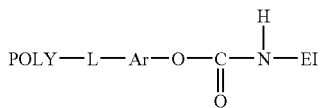

where POLY is a water soluble polymer as described herein, L is a linking group, Ar is an aromatic group, and NH-EI taken together represents an EI having an amino group. This particular structure possesses a hydrolyzable carbamate bond, such that the EI is released upon hydrolysis. Preferably, upon hydrolysis, parent EI is released, along with $CO_2$ and the corresponding aromatic alcohol. Preferred aromatic groups are ortho, meta, or para-substituted phenyl. Preferred L groups for this particular embodiment of the invention are —O— and —NH—C(O)—. A particular embodiment of such a conjugate is presented in Table 1 above. Also encompassed by the above are dumbell-type structures having an EI or other anti-HIV agent attached via an identical linkage to the POLY terminus. Particular polymers and conjugates falling within the above generalized structure are described in U.S. Pat. No. 6,413,507, the contents of which are expressly incorporated herein by reference. Preferred polymer reagents include those described in the Examples in U.S. Pat. No. 6,413,507 and shown in Table 1 above.

For embodiments of the invention employing an amino-selective reagent such as those described above, and in which a hydrolyzable conjugate is desired, an entry inhibitor compound having a hyrolyzable spacer releasably attached thereto is employed, e.g., as exemplified by Examples 11-15. Generally, this strategy involves the following synthetic steps 1) initial protection of any EI primary amines, i.e. lysine employing traditional protecting group chemistry, e.g. Boc, 2) addition of a suitable spacer (e.g., glycine, alanine, etc.) to the hydroxyl functionalities of tyrosine, serine, or threonine of the EI via a degradable linkage such as a carboxy group, 3) deprotection of the spacer group, and 4) subsequent conjugation with an amine selective PEG reagent, and 5) final deprotection of the primary amines. Generally, this spacer approach is suitable for modifying any of the herein described polymer reagents, and in particular, those in Table 1, to thereby impart releasable properties thereto, in accordance with a preferred embodiment of the present invention.

Gel formulations employing polymers of the type described immediately above will be discussed in greater detail in the sections that follow.

An additional pictoral representation of conjugation of an EI with a particular degradable carbamate-linked PEG is provided below, where the PEG reagent contains a para-substituted phenyl ring. For instance, when EI is T-20, the illustrative PEG reagent can potentially couple to one or both of the peptide's lysine amino groups.

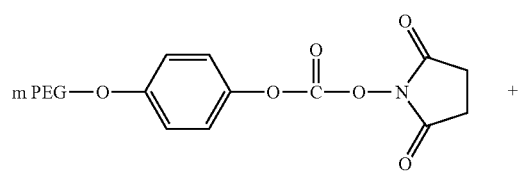

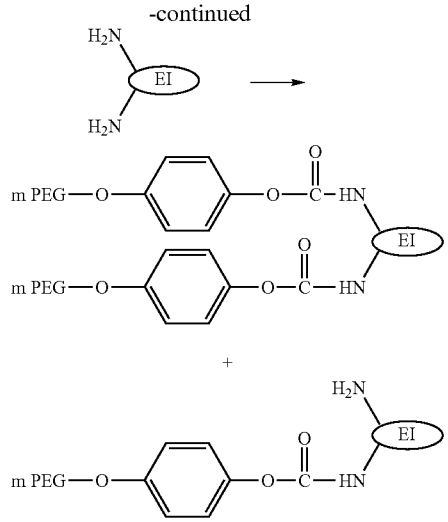

Although mPEG is shown as the POLY portion, any of the POLY structures described herein can be utilized. In instances where it is desirable to covalently attach a water soluble polymer to only one amino group contained within an EI, or when more than one reactive amino group is present on the EI such as those present on lysines, one may either employ a protection/deprotection strategy as is commonly known in the art, or alternatively, employ separation/purification techniques to isolate a desired conjugate or type of conjugate resulting from a random PEGylation approach (e.g., mono-PEG mers, di-PEG mers, tri-PEG mers, etc.).

In one preferred embodiment of a conjugate of the invention, when the EI is T-20 or T-1249, and the water soluble polymer is attached to the N-terminal via reaction with an aldehyde-terminated water soluble polymer, such a water soluble polymer lacks an internal amido group, and even more specifically, possesses a structure dissimilar from structures of the type: PEG-O—$(CH_2)_m$—C(O)—NH—$(CH_2)_p$—CHO, where m ranges from about 1-17, n ranges from about 10 to 1,000, and p ranges from about 1 to 3. In instances in which use of an aldehyde-terminated polymer is preferred, exemplary polymers are those described in co-owned International Patent Application No. PCT/US03/28221 entitled, "Water-Soluble Polymer Alkanals", the contents of which are expressly incorporated herein by reference.

Reaction conditions for coupling PEG to an EI will vary depending upon the EI, the desired degree of PEGylation, and the particular reagent being utilized. Typically, conjugation of a polymeric reagent to an amino group of an EI is carried out at pHs from around 5 to around 9.5, preferably from about 8 to about 9.5, and at room temperature, with reaction times ranging from about 30 minutes to several hours. Preferred molar ratios of PEG reagent to protein vary from about 1:1 to 5:1, or even 10:1, or even up to 100:1. Increasing the pH increases the rate of reaction, while lowering the pH reduces the rate of reaction. Selective reactions (e.g., at the N-terminus) may be conducted, particularly with a polymer functionalized with a ketone or an alpha-methyl branched aldehyde and/or under specific reaction conditions (e.g., reduced pH). See, for example, Examples 1-3 and 6-15, demonstrating both random and site selective polymer attachment to form illustrative EI polymer conjugates and compositions of the invention.

Carboxyl groups represent another functional group that can serve as a point of attachment on the EI. Structurally, the conjugate will comprise the following:

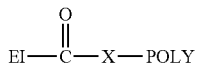

where EI and the adjacent carbonyl group corresponds to the carboxyl-containing EI, X is a linkage, preferably a heteroatom selected from O, N(H), and S, and POLY is a water-soluble polymer such as PEG, optionally terminating in an end-capping moiety.

The C(O)—X linkage results from the reaction between a polymer reagent bearing a terminal functional group and a carboxyl-containing EI. As discussed above, the specific linkage will depend on the type of functional group utilized. If the polymer is end-functionalized or "activated" with a hydroxyl group, the resulting linkage will be a carboxylic acid ester and X will be O. If the polymer is functionalized with a thiol group, the resulting linkage will be a thioester and X will be S. When certain multi-arm, branched or forked polymers are employed, the C(O)X moiety, and in particular the X moiety, may be relatively more complex and may include a longer linkage structure.

Water-soluble derivatives containing a hydrazide moiety are also useful for conjugation at carboxyl groups. Such groups may be introduced into an EI via attachment of a small spacer containing a carboxy functionality, e.g., an amino acid, or by oxidation of a hydroxyl. An example of such a derivative includes a polymer having the following structure:

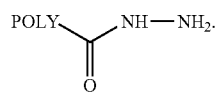

Thiol groups contained or introduced within the EI can serve as effective sites of attachment for the water-soluble polymer. In particular, cysteine residues provide thiol groups when the EI is a peptide or comprises a peptide portion. The thiol groups in such cysteine residues can then be reacted with an activated PEG that is specific for reaction with thiol groups, e.g., an N-maleimidyl polymer or other derivative, as described in U.S. Pat. Nos. 5,739,208 and 6,602,498, and in International Patent Publication No. WO 01/62827.

Specific examples, along with the corresponding conjugate, are provided in Table 2 below. In the table, the variable (n) represents the number of repeating monomeric units and "—S-EI" represents an EI following conjugation to the water-soluble polymer. While each polymeric portion presented in Table 2 terminates in a "CH$_3$" group, other groups (such as H, ethyl and benzyl) can be substituted therefor.

TABLE 2

THIOL-SPECIFIC POLYMER REAGENTS AND THEIR RESPECTIVE EI CONJUGATES

Polymeric Reagent

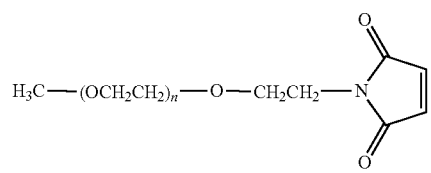

mPEG Maleimide Derivative

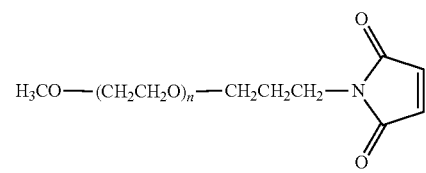

mPEG Maleimide Derivative

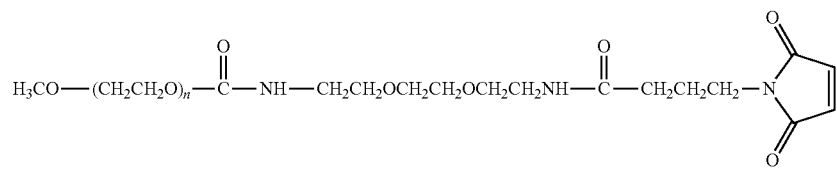

mPEG Maleimide Derivative

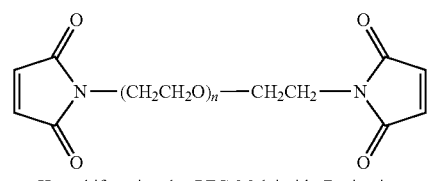

Homobifunctional mPEG Maleimide Derivative

TABLE 2-continued
THIOL-SPECIFIC POLYMER REAGENTS AND THEIR RESPECTIVE EI CONJUGATES
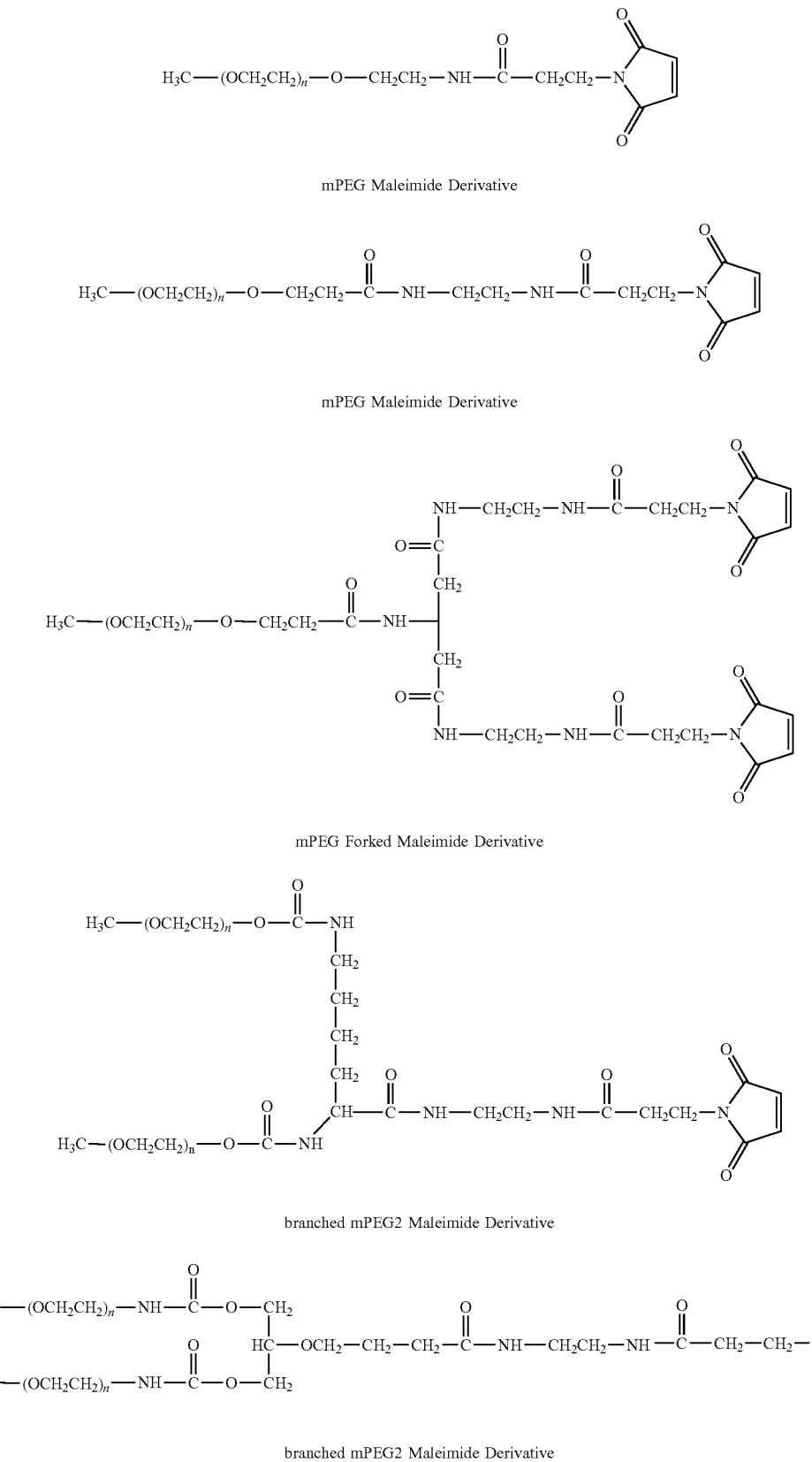
mPEG Maleimide Derivative
mPEG Maleimide Derivative
mPEG Forked Maleimide Derivative
branched mPEG2 Maleimide Derivative
branched mPEG2 Maleimide Derivative

TABLE 2-continued
THIOL-SPECIFIC POLYMER REAGENTS AND THEIR RESPECTIVE EI CONJUGATES
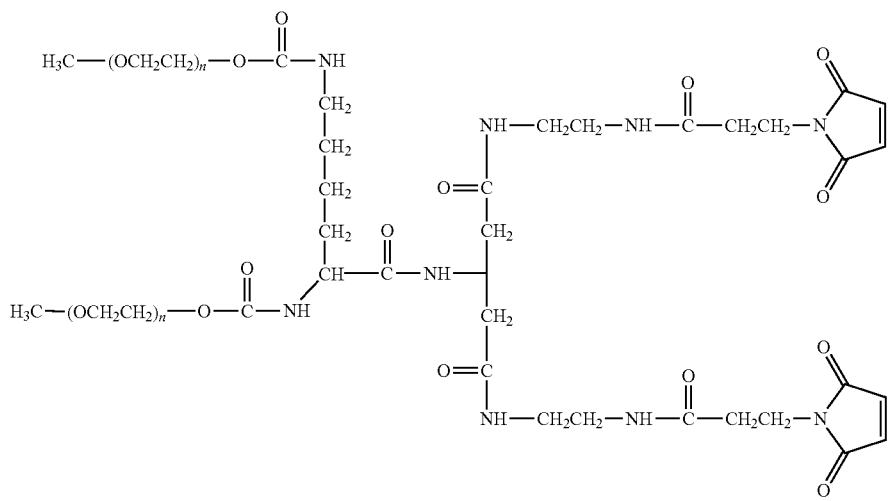
Branched mPEG2 Forked Maleimide Derivative
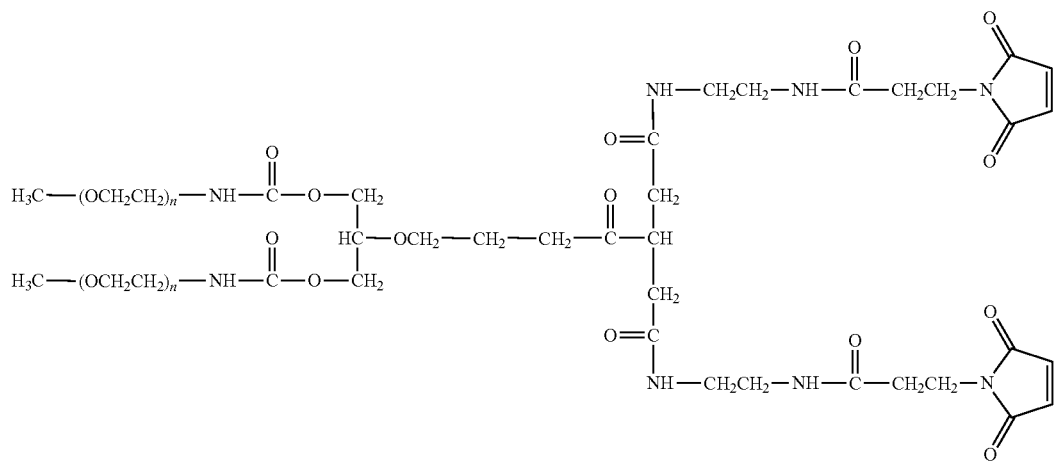
Branched mPEG2 Forked Maleimide Derivative
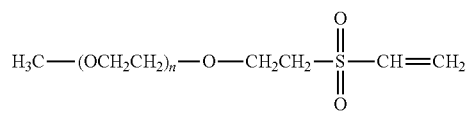
mPEG Vinyl Sulfone Derivative
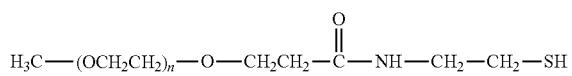
mPEG Thiol Derivative
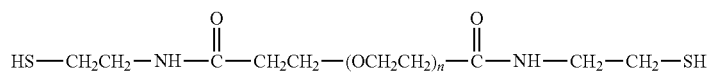
Homobifunctional PEG Thiol Derivative TABLE 2-continued

THIOL-SPECIFIC POLYMER REAGENTS AND THEIR RESPECTIVE EI CONJUGATES

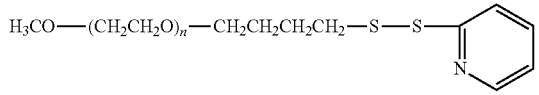

mPEG Disulfide Derivative
As described in copending U.S. Provisional Application
No. 60/639,823 filed on Dec. 21, 2004 and entitled
"Stabilized Polymeric Thiol Reagents."

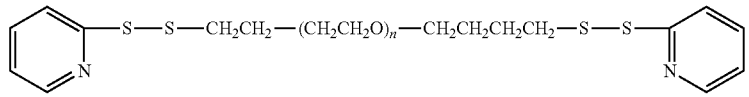

Homobifunctional Disulfide Derivative
As described in copending U.S. Provisional Application
No. 60/639,823 filed on Dec. 21, 2004 and entitled
"Stabilized Polymeric Thiol Reagents.")

EI Conjugate

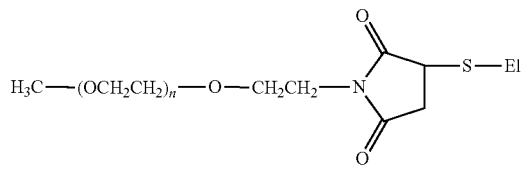

Thioether Linkage
Structure 2-1

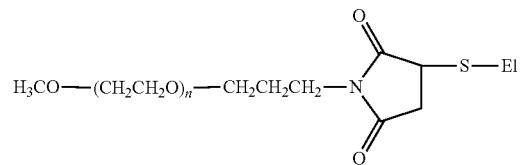

Thioether Linkage
Structure 2-2

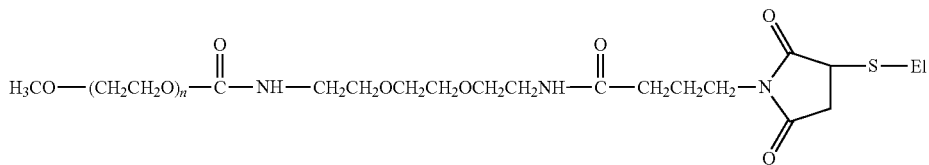

Thioether Linkage
Structure 2-3

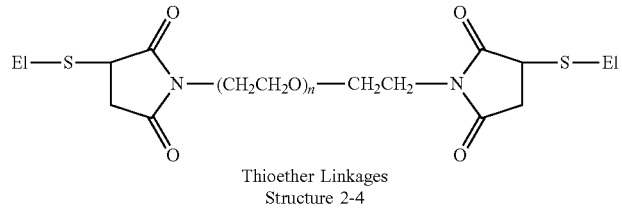

Thioether Linkages
Structure 2-4

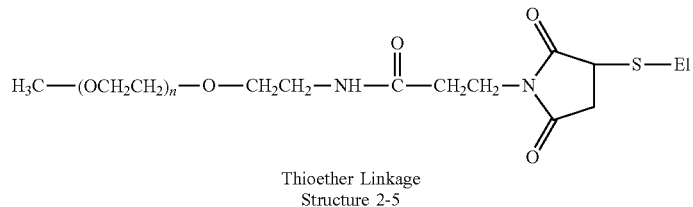

Thioether Linkage
Structure 2-5

TABLE 2-continued
THIOL-SPECIFIC POLYMER REAGENTS AND THEIR RESPECTIVE EI CONJUGATES
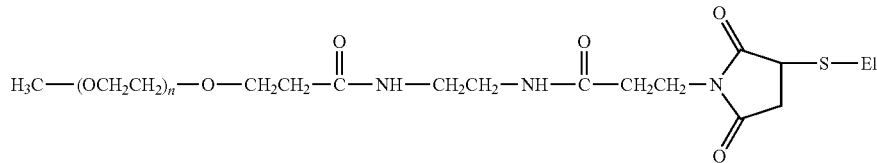
Thioether Linkage
Structure 2-6
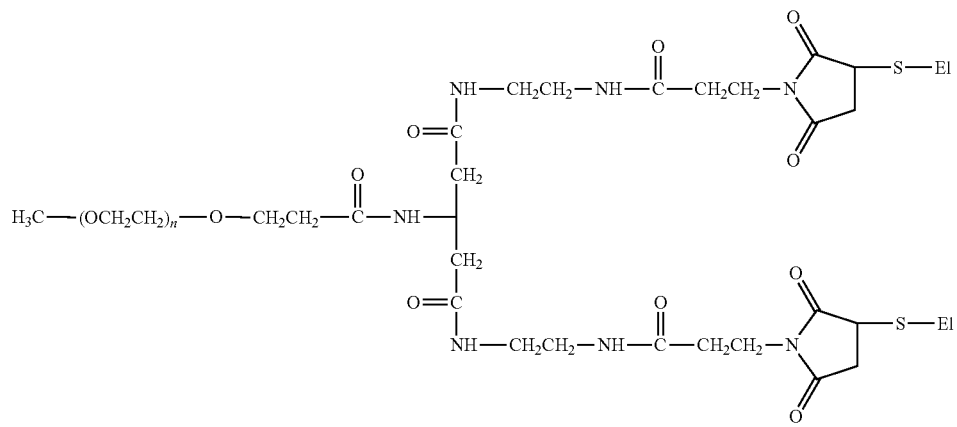
Thioether Linkage
Structure 2-7
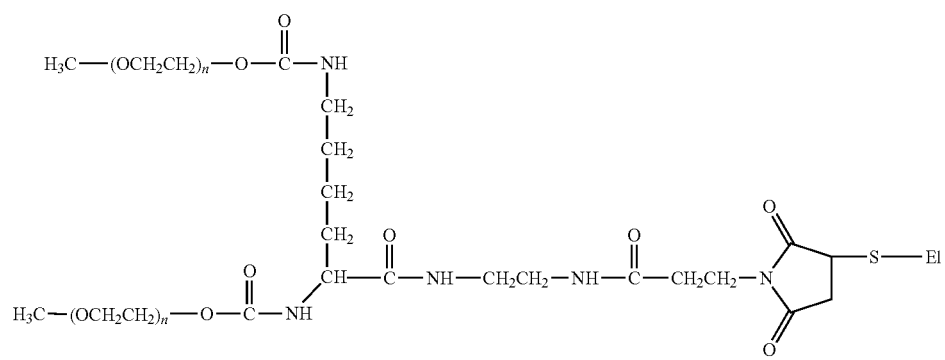
Thioether Linkage
Structure 2-8
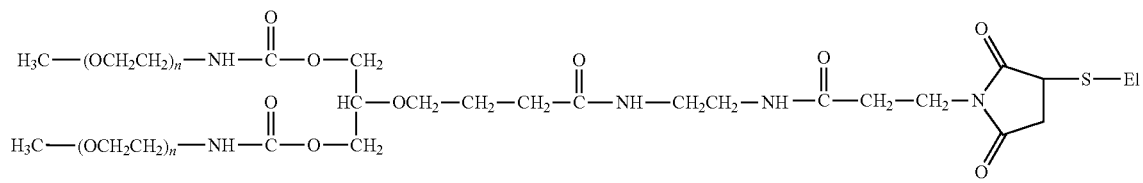
Thioether Linkage
Structure 2-9

TABLE 2-continued
THIOL-SPECIFIC POLYMER REAGENTS AND THEIR RESPECTIVE EI CONJUGATES
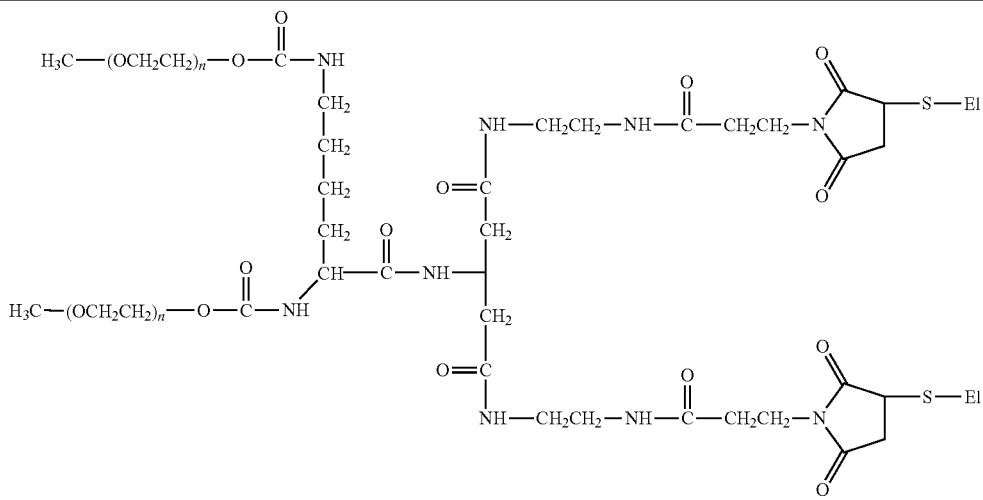
Thioether Linkages
Structure 2-10
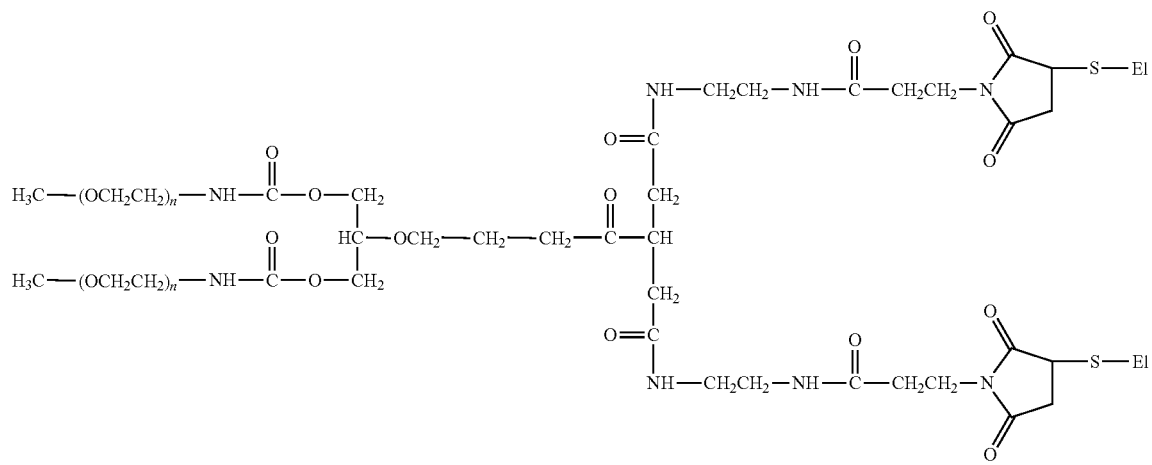
Thioether Linkages
Structure 2-11
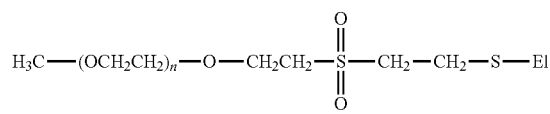
Thioether Linkage
Structure 2-12
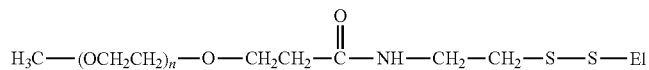
Disulfide Linkage
Structure 2-13
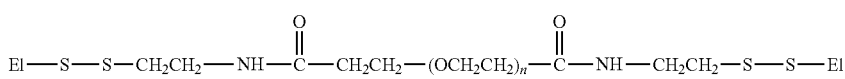
Disulfide Linkages
Structure 2-14

TABLE 2-continued

THIOL-SPECIFIC POLYMER REAGENTS AND THEIR RESPECTIVE EI CONJUGATES

H$_3$CO—(CH$_2$CH$_2$O)$_n$—CH$_2$CH$_2$CH$_2$CH$_2$—S—S—El

Disulfide Linkgae
Structure 2-15

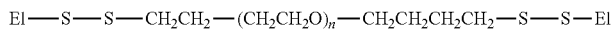

El—S—S—CH$_2$CH$_2$—(CH$_2$CH$_2$O)$_n$—CH$_2$CH$_2$CH$_2$CH$_2$—S—S—El

Disulfide Linkages
Structure 2-16

With respect to conjugates formed from water-soluble polymers bearing one or more maleimide functional groups (regardless of whether the maleimide reacts with an amine or thiol group on the EI), the corresponding maleamic acid form(s) of the water-soluble polymer can also react with the EI. Under certain conditions (e.g., a pH of about 7-9 and in the presence of water), the maleimide ring will "open" to form the corresponding maleamic acid. The maleamic acid, in turn, can react with an amine or thiol group, e.g., of an EI, as described in International Patent Application Publication No. WO 04/060966. Exemplary maleamic acid-based reactions are schematically shown below. POLY represents the water-soluble polymer, and EI represents the entry inhibitor.

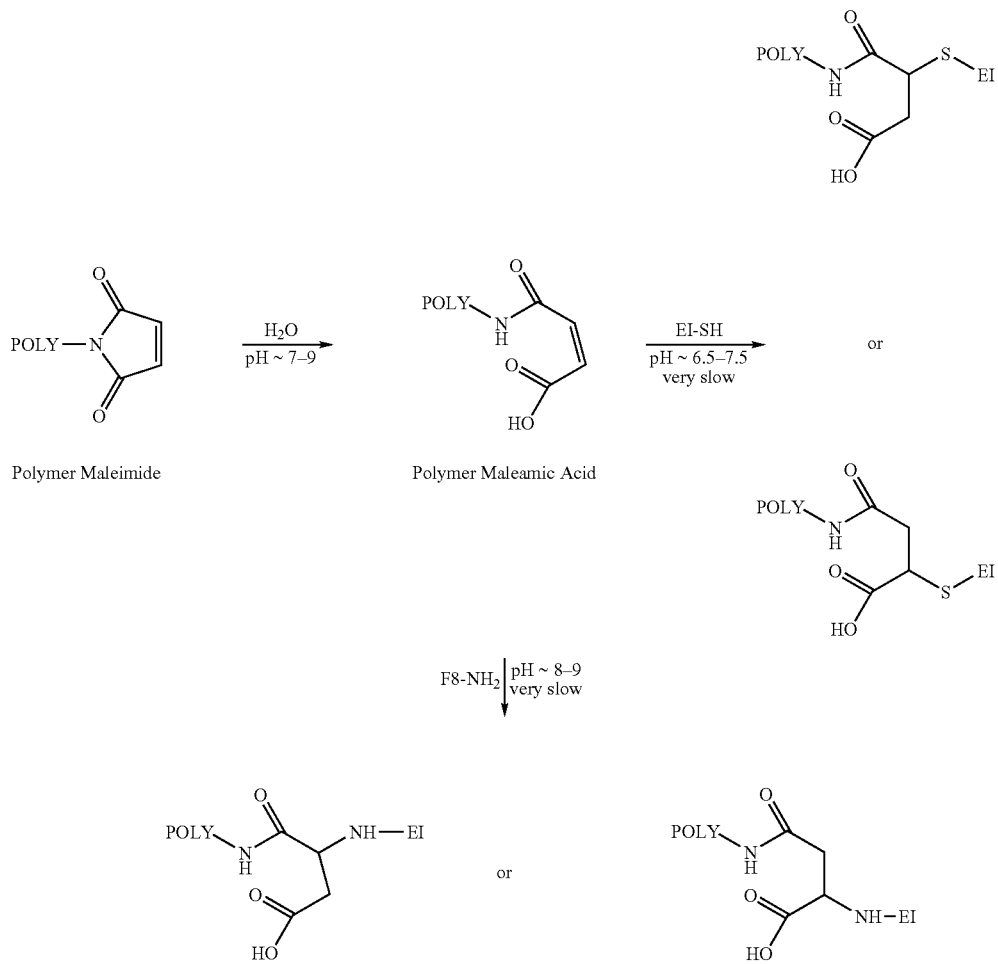

In yet another embodiment, a representative conjugate in accordance with the invention possesses the following structure:

POLY-L$_{0,1}$-C(O)Z—Y—S—S-EI wherein POLY is a water-soluble polymer, L is an optional linker, Z is a heteroatom selected from the group consisting of O, NH, and S, and Y is selected from the group consisting of C$_{2-10}$ alkyl, C$_{2-10}$ substituted alkyl, aryl, and substituted aryl. Polymeric reagents that can be reacted with an EI and result in this type of conjugate are described in copending application filed on Jan. 6, 2004, entitled "Thiol-Selective Water Soluble Polymer Derivatives," and assigned U.S. Ser. No. 10/753,047, corresponding to International Patent Application Publication No. WO 04/063250.

With respect to polymeric reagents, those described here and elsewhere can be purchased from commercial sources (e.g., Nektar Therapeutics, Huntsville Ala.). In addition, methods for preparing the polymeric reagents are described in the literature.

Typically, although not necessarily, the linkage between the EI and the polymeric reagent includes one or more atoms such as one or more of carbon, nitrogen, sulfur, and combinations thereof. For instance, preferred hydrolytically stable linkages comprise an amide, secondary amine, carbamate, thioether, or disulfide group. Optionally, additional atoms can connect the linkage to the chain of repeating monomers within the polymeric reagent. The same holds true for embodiments wherein the linkage is degradable, i.e, comprises a hydrolytically degradable moiety. Typically, the degradable linkage, when considered overall, contains additional atoms or combinations of atoms connecting the degradable moiety per se to the polymer and/or the EI. Nonlimiting examples of specific series of atoms connecting the EI to the chain of repeating monomers designated herein as POLY include those selected from the group consisting of —O—, —S—, —S—S—, —C(O)—, —O—C(O)—, —C(O)—O—, —C(O)—NH—, —NH—C(O)—NH—, —O—C(O)—NH—, —C(S)—, —CH$_2$—, —CH$_2$—CH$_2$—, —CH$_2$—CH$_2$—CH$_2$—, —CH$_2$—CH$_2$—CH$_2$—CH$_2$—, —O—CH$_2$—, —CH$_2$—O—, —O—CH$_2$—CH$_2$—, —CH$_2$—O—CH$_2$—, —CH$_2$—CH$_2$—O—, —O—CH$_2$—CH$_2$—CH$_2$—, —CH$_2$—O—CH$_2$—CH$_2$—, —CH$_2$—CH$_2$—O—CH$_2$—, —CH$_2$—CH$_2$—CH$_2$—O—, —O—CH$_2$—CH$_2$—CH$_2$—CH$_2$—, —CH$_2$—O—CH$_2$—CH$_2$—CH$_2$—, —CH$_2$—CH$_2$—O—CH$_2$—CH$_2$—, —CH$_2$—CH$_2$—CH$_2$—O—CH$_2$—, —CH$_2$—CH$_2$—CH$_2$—CH$_2$—O—, —C(O)—NH—CH$_2$—, —C(O)—NH—CH$_2$—CH$_2$—, —CH$_2$—C(O)—NH—CH$_2$—, —CH$_2$—CH$_2$—C(O)—NH—, —C(O)—NH—CH$_2$—CH$_2$—CH$_2$—, —CH$_2$—C(O)—NH—CH$_2$—CH$_2$—, —CH$_2$—CH$_2$—C(O)—NH—CH$_2$—, —CH$_2$—CH$_2$—CH$_2$—C(O)—NH—, —C(O)—NH—CH$_2$—CH$_2$—CH$_2$—CH$_2$—, —CH$_2$—C(O)—NH—CH$_2$—CH$_2$—CH$_2$—, —CH$_2$—CH$_2$—C(O)—NH—CH$_2$—CH$_2$—, —CH$_2$—CH$_2$—CH$_2$—C(O)—NH—CH$_2$—, —CH$_2$—CH$_2$—CH$_2$—C(O)—NH—CH$_2$—CH$_2$—, —CH$_2$—CH$_2$—CH$_2$—CH$_2$—C(O)—NH—, —C(O)—O—CH$_2$—, —CH$_2$—C(O)—O—CH$_2$—, —CH$_2$—CH$_2$—C(O)—O—CH$_2$—, —C(O)—O—CH$_2$—CH$_2$—, —NH—C(O)—CH$_2$—, —CH$_2$—NH—C(O)—CH$_2$—, —CH$_2$—CH$_2$—NH—C(O)—CH$_2$—, —NH—C(O)—CH$_2$—CH$_2$—, —CH$_2$—NH—C(O)—CH$_2$—CH$_2$—, —CH$_2$—CH$_2$—NH—C(O)—CH$_2$—CH$_2$—, —C(O)—NH—CH$_2$—, —C(O)—NH—CH$_2$—CH$_2$—, —O—C(O)—NH—CH$_2$—, —O—C(O)—NH—CH$_2$—CH$_2$—, —O—C(O)—NH—CH$_2$—CH$_2$—CH$_2$—, —NH—CH$_2$—, —NH—CH$_2$—CH$_2$—, —CH$_2$—NH—CH$_2$—, —CH$_2$—CH$_2$—NH—CH$_2$—, —CH$_2$—CH$_2$—NH—, —C(O)—CH$_2$—, —C(O)—CH$_2$—CH$_2$—, —CH$_2$—C(O)—CH$_2$—, —CH$_2$—CH$_2$—C(O)—CH$_2$—, —CH$_2$—CH$_2$—C(O)—CH$_2$—CH$_2$—, —CH$_2$—CH$_2$—C(O)—, —CH$_2$—CH$_2$—CH$_2$—C(O)—NH—CH$_2$—CH$_2$—, —NH—C(O)—CH$_2$—, —CH$_2$—NH—C(O)—CH$_2$—, —CH$_2$—CH$_2$—NH—C(O)—CH$_2$—CH$_2$—, —O—C(O)—NH—[CH$_2$]$_{0-6}$—(OCH$_2$CH$_2$)$_{0-2}$—, —C(O)—NH—(CH$_2$)$_{1-6}$—NH—C(O)—, —NH—C(O)—NH—(CH$_2$)$_{1-6}$—NH—C(O)—, —O—C(O)—CH$_2$—, —O—C(O)—CH$_2$—CH$_2$—, and —O—C(O)—CH$_2$—CH$_2$—CH$_2$—.

Additionally, bifunctional linkers such as amino acids or difunctional PEG oligomers may be used to connect the EI to the polymer reagent.

The conjugates are typically part of a composition. The composition may contain a single type of polymer conjugate, e.g., solely PEG-EI monomers (i.e., having only one PEG chain covalently attached to the EI, although the PEGs may be covalently attached to different positions within the EI, e.g., at different amino acids within the sequence), or may contain a plurality of conjugates, preferably although not necessarily, each having from about one to about three water-soluble polymers covalently attached to one EI.

As discussed briefly above, control of the desired number of polymers for any given EI can be achieved by selecting the proper polymeric reagent, the ratio of polymeric reagent to EI, temperature, pH conditions, and other aspects of the conjugation reaction. In addition, reduction or elimination of the undesired conjugates (e.g., those conjugates having four or more attached polymers) can be achieved by purification.

Additional Multi-Armed Polymer Conjugates

Multi-armed polymers for use in forming conjugates having multiple EIs or other anti-HIV agents covalently attached thereto have been described previously herein. Multi-armed polymers are particularly attractive in cases where high doses of the EI are required to deliver a therapeutically effective amount, e.g., of T-20 or T-1249. In this way, drug is "loaded up", preferably releasably, onto a single polymer molecule having several reactive sites suitable for covalent attachment.

One preferred type of multi-armed polymer for achieving maximal EI loading is a multi-arm block copolymer having an inner core region defined by a central core molecule having polypeptide segments covalently attached thereto and an outer hydrophilic region defined by hydrophilic polymer segments covalently attached to each of the polypeptide polymer segments. Thus, each arm of the multi-arm structure is a block copolymer comprising an inner (i.e. closer or proximal to the central core molecule) polypeptide polymer segment and an outer (i.e. further or distal from the central core molecule) hydrophilic polymer segment. Such multi-arm block copolymers are particularly well suited for encapsulation or entrapment of biologically active molecules within the inner core region. As used in the present context, "encapsulation" or "entrapment" is intended to refer to the physical confinement of an EI within the inner core region of the copolymer, whether by covalent attachment, charge interaction, metal-acid complex, van der Waals forces, or other attraction or bonding force. Such unimolecular multi-arm block copolymers typically have a total number average molecular weight of from about 5,000 Da to about 120,000 Da, preferably from about 10,000 Da to about 100,000 Da, and more preferably from about 20,000 Da to about 80,000 Da.

The outer hydrophilic polymer segments are preferably poly(ethylene glycol), although other hydrophilic polymer segments can also be used. The use of a polypeptide polymer segment as part of the inner core region of the unimolecular multi-arm structure provides tremendous flexibility in designing and adjusting the drug delivery properties of the multi-arm structure. Interaction between an EI and the core region of the unimolecular multi-arm structure can greatly affect drug loading and drug release characteristics. In the present invention, depending on the structure of the polypeptide polymer segments, the inner core region can be hydrophobic, charged, suitable for covalent attachment to drug molecules, or any combination thereof.

Preferably, the central core molecule is a residue of a polyamine having at least three termini bearing an amine group. The use of a polyamine core is preferred because the amine groups of the core readily react with the carboxylic acid group of an amino acid to form an amide linkage. Core molecules having other functional groups available for attachment to the copolymer arms can, however, also be used. In embodiments utilizing a polyamine core, the number of amine groups will dictate the number of copolymer arms in the multi-arm structure. Preferably, the polyamine comprises from 3 to about 25 amine groups. In various embodiments, the polyamine comprises at least about 5 amine groups, at least about 8 amine groups, or at least about 10 amine groups. Multi-armed polymers having these types of structures are described in detail in co-owned patent application entitled, "Multi-Arm Polypeptide Poly(ethylene Glycol) Block Copolymers as Drug Delivery Vehicles", filed on Dec. 24, 2003, which corresponds to International Patent Application Publication No. WO/04060977, the contents of which are expressly incorporated herein by reference. A representative embodiment of this aspect of the invention is provided in Example 14.c.

Illustrative polymer structures include multi-arm (3, 4, 5, 6, 7, 8, 9, 10, 11 or 12-arm) poly(benzyl aspartate)-PEG, poly(aspartic acid)-PEG having multiple EIs covalently attached to the polypeptide core of the structure, preferably although not necessarily via degradable linkages such as ester and hydrolyzable carbamate. Alternatively, rather than being covalently attached, an EI may be entrapped within the inner core region.

An illustrative schematic showing covalent attachment of a particular hydroxyl group of an EI to a multi-armed polymer is provided below. Selective attachment of a polymer at one hydroxy site within the EI is achieved via a spacer molecule having at its terminus, a reactive group such as an amine. See, for example, Examples 11-15.

More specifically, in this embodiment of the invention, a hydroxyl group such as a tyrosine hydroxyl in the EI is used as a selective point for attachment and introduction of a hydrolyzable linkage (e.g., a carbonate or ester) via a spacer having, for example, a reactive amino group at its free, uncoupled end. This approach takes advantage of the difference in reactivity between tyrosine and serine hydroxyls, to thereby achieve a site-selective reaction at a tyrosine hydroxyl group. Prior to reaction at the tyrosine hydroxyl, amino groups within the EI are protected or blocked from coupling using any appropriate amino-protecting group known in the art. The use of t-Boc in the schematic below is meant to be purely illustrative. In the embodiment below, the spacer possesses at its end distal to the EI, a reactive group such as an amine, that is suitable for conjugation to, for instance, a multi-arm PEG or a co-polymer PEG-based system having an inner hydrophobic and an outer hydrophilic region as described above. Protection of the other reactive amines in the EI allows the selective introduction of one particular amino site extending from the EI, and moreover, this approach provides a mechanism for introducing into the molecule a degradable covalent linkage. The modified EI, having an extended linker or spacer covalently attached thereto, is then covalently coupled to a water-soluble polymer as described herein. This approach differs from those previously described herein in the sense that the "linker" or "linker precursor" is first introduced into the EI, preferably in a selective fashion, to form an exemplary EI intermediate (EI-O—C(O)—Z-Spacer-NH$_2$) which is then suitable for attachment to a polymer, that may be linear, branched, or multi-armed. In this structure, EI-O—, represents the residue of a hyroxyl group present within the EI.

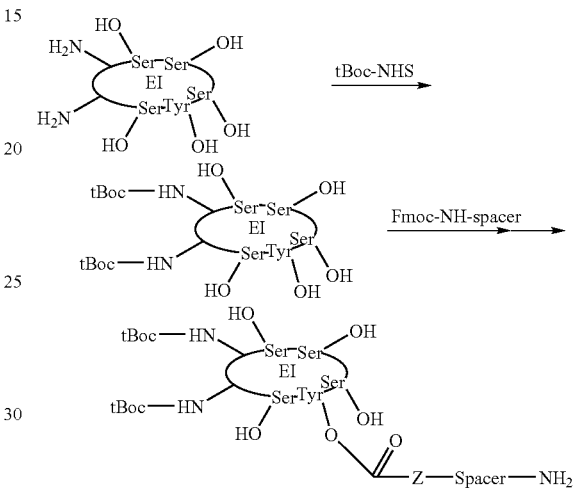

At this point, mono-amino derivatives of the EI can be linked into, e.g., a multi-armed polymer in a conventional fashion. Upon completion of conjugation, the t-Boc group is removed using known techniques. In the above figure, Z is preferably O, NH or CH$_2$, and the spacer can, for example, be an amino acid or a segment of an amino acid or alternatively an oligomeric PEG, e.g., a difunctional PEG or polymer linker having from 1 to about 20 monomer subunits, preferably from 1-10 monomer subunits, more preferably having a number of subunits selected from 1, 2, 3, 4, 5, 6, 7, and 9.

In a slightly different approach, when it is desired to utilize carboxylic acid groups such as those contained in the amino acids glutamic or aspartic acid, protection of all reactive amino and hydroxyl groups is preferred. Following mono-conjugation of the —COOH group with a hydroxyl-terminated spacer to form a hydrolyzable carboxy ester, covalent attachment to a multi-armed PEG or the like can similarly be accomplished. Synthetic methods such as these can be determined by one skilled in the art, when considered along with the teachings of the instant specification and knowledge commonly available in the art. This methodology can be extended to prepare similar multi-armed conjugates having other (e.g., degradable or non-degradable) linkages.

Hydrogels

In contrast to the conjugate or covalently attached EI compositions previously described, additionally provided herein are hydrogel-EI compositions where the EI is not necessarily covalently attached to the polymer component(s), which are present in the form of a gel. Such hydrogels can be cross-linked or non-cross-linked, and preferably contain a PEG-component. In one particular embodiment, the hydrogel components are non-cross-linked or are lightly crosslinked to facilitate release of the EI. The EI may be present in conjugated and/or unconjugated form.

An illustrative hydrogel possesses the aromatic-hydrolyzable carbamate segment described previously above. In particular, the hydrogel is composed of a polymer bonded to a crosslinking agent through a hydrolyzable carbamate linkage. The crosslinking agent in a preferred embodiment is a difunctional polymer as described above having the formula:

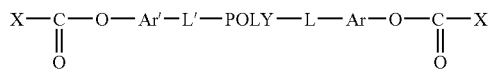

wherein POLY, POLY', L, L', X, X', Ar, and Ar' are as described previously.

In a preferred embodiment, the crosslinking agent has the formula:

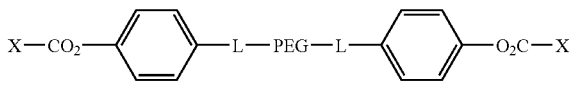

wherein X and L are as described above. Thus, the cross-linking of a polymer having multiple amino groups with the above crosslinking agent is illustrated below:

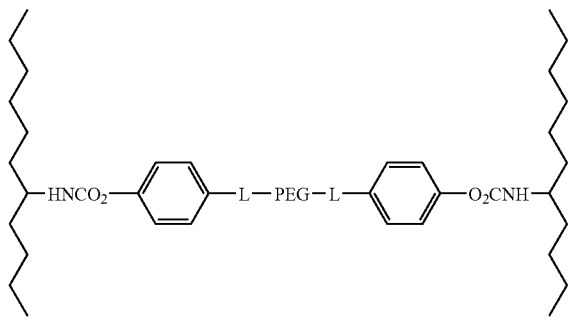

where the zig-zag notation represents a polymer having amine groups and where L is as described above.

As will be apparent, the carbamate linkages between the polymer portions and the crosslinker are hydrolyzable. Thus, this hydrogel gradually breaks down or degrades in the body as a result of the hydrolysis of the carbamate linkages.

Another type of advantageous hydrogel for preparing a sustained delivery EI composition possesses carbonate linkages. More particularly, provided is a a water soluble, nonpeptidic polymer composed of two or more oligomers linked together by hydrolytically degradable carbonate linkages, as described in co-owned U.S. Pat. No. 6,348,558, the contents of which is expressly incorporated herein by reference. The polymer can be hydrolytically degraded into small oligomers in an aqueous environment, e.g., in vivo, and can be used to prepare degradable hydrogels.

A representative polymer of this sort is represented by the formula:

X—O—[(—CH$_2$CH$_2$—O—)$_n$—CO$_2$—]$_m$—(CH$_2$CH$_2$O)$_n$—Y, where n is an integer of from about 2 to about 2,000, m is an integer of from about 2 to about 200, and where X and Y each independently is H, alkyl, alkenyl, aryl, or a reactive moiety, and can be same or different. In the instance where either X or Y (or both) is reactive with a functional group of the EI, then the EI may optionally be covalently attached thereto in yet another embodiment of the invention.

In yet another embodiment, a hydrogel for use in preparing an EI composition is a thiosulfonate gel as described in co-owned utility patent application entitled, "Methods for the Formation of Hydrogels Using Thiosulfonate Compositions and Uses Thereof", filed on Dec. 31, 2003, the content of which is expressly incorporated herein by reference More particularly, in accordance with this embodiment of the invention, hydrogel forming components are preferably multi-arm thiosulfonate polymer derivatives that form a crosslinked polymer composition when exposed to base, without requiring the presence of a second cross-linking reagent, redox catalyst, or radiation. Such thiosulfonate polymer derivatives can also form a hydrogel by reaction with a water-soluble polymer having at least two thiol groups.

Generally, such compositions comprise hydrogel-forming components corresponding to the formula below:

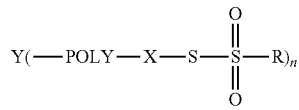

where POLY is a water-soluble polymer, n ranges from 3 to about 100, X is a linking group, Y is a moiety derived from a molecule having at least three nucleophilic groups, and R is an alkyl or aryl group. Exemplary linking groups are described elsewhere in the document. The polymer may optionally contain at least one degradable linkage, e.g., an ester, carbonates acetal, orthoester, phosphate, or thiolester. The presence of one or more degradable linkages allows for the degradation of the polymer chains (e.g., by hydrolysis or enzymatic degradation) with concomitant breakdown and dissolution of the hydrogel. In a preferred embodiment, particularly when the EI is T-20 or T-1249, the hydrogel or polymer containing composition effective to form a hydrogel, is one which does not exhibit reverse gelation properties, i.e., exists as a liquid below physiological temperature but which forms a hydrogel at physiological temperature. As an example, such hydrogel or hydrogel forming compositions will typically be made of polymers other than Poloxomer 407™.

Hydrogel compositions of the invention can be prepared prior to use. Formed hydrogel compositions may optionally be subject to dehydration or lyophilization in order to remove bound water and used as either the intact hydrogel or reduced to powder or particulate form. Hydrogel compositions of the invention may also be employed without dehydration or lyophilization as formed objects or maybe incorporated into delivery systems including without limitation: ocular insert, suppositories, pessaries, transdermal patches, or capsules filled with the hydrogel compositions.

Regardless of the form of the hydrogel forming composition or hydrogel composition, it is possible to package the compositions in single use, multiple use or bulk containers. The preparations may optionally be sterilized by art-recognized procedures. In one preferred embodiment, the materials are packaged in sterile single use containers. In other embodiments, the materials are packaged for ease of reconstitution by addition of water, aqueous solutions or suspensions in single or multiple use containers. In another embodiment, the materials are sold as a kit with a base to initiate gel formation.

Purification of Conjugates

The polymer-EI conjugates of the invention can be purified to obtain/isolate different conjugated species. Specifically, the product mixture can be purified to obtain an average of anywhere from one, two, or three or even more PEGs per EI. Preferred are EI conjugates having one polymer molecule attached thereto. The strategy for purification of the final conjugate reaction mixture will depend upon a number of factors, including, for example, the molecular weight of the polymeric reagent employed, the particular EI, the desired dosing regimen, and the residual activity and in vivo properties of the individual conjugate(s).

If desired, conjugates having different molecular weights can be isolated using gel filtration chromatography and/or ion exchange chromatography. That is to say, gel filtration chromatography is used to fractionate differently numbered polymer-to-EI ratios (e.g., 1-mer, 2-mer, 3-mer, and so forth, wherein "1-mer" indicates one polymer to an EI, "2-mer" indicates two polymers attached to an EI, and so on) on the basis of their differing molecular weights (where the difference corresponds essentially to the average molecular weight of the water-soluble polymer portion). For example, in an exemplary reaction where a 100,000 Dalton polypeptide is randomly conjugated to a polymeric reagent having a molecular weight of about 20,000 Daltons, the resulting reaction mixture may contain unmodified protein (having a molecular weight of about 100,000 Daltons), monoPEGylated protein (having a molecular weight of about 120,000 Daltons), diPEGylated protein (having a molecular weight of about 140,000 Daltons), and so forth.

While this approach can be used to separate PEG and other polymer-EI conjugates having different molecular weights, this approach is generally ineffective for separating positional isomers having different polymer attachment sites within the EI. For example, gel filtration chromatography can be used to separate from each other mixtures of PEG 1-mers, 2-mers, 3-mers, and so forth, although each of the recovered PEG-mer compositions may contain PEGs attached to different reactive amino groups (e.g., lysine residues) or other functional groups of the EI.

Gel filtration columns suitable for carrying out this type of separation include Superdex™ and Sephadex™ columns available from Amersham Biosciences (Piscataway, N.J.). Selection of a particular column will depend upon the desired fractionation range desired. Elution is generally carried out using a suitable buffer, such as phosphate, acetate, or the like. The collected fractions may be analyzed by a number of different methods, for example, (i) optical density (OD) at 280 nm for protein content, (ii) bovine serum albumin (BSA) protein analysis, (iii) iodine testing for PEG content (Sims et al. (1980) *Anal. Biochem,* 107: 60-63), and (iv) sodium dodecyl sulfate polyacrylamide gel electrophoresis (SDS PAGE), followed by staining with barium iodide.

Separation of positional isomers is carried out by reverse phase chromatography using a reverse phase-high performance liquid chromatography (RP-HPLC) C18 column (Amersham Biosciences or Vydac) or by ion exchange chromatography using an ion exchange column, e.g., a Sepharose™ ion exchange column available from Amersham Biosciences. Either approach can be used to separate polymer-active agent isomers having the same molecular weight (positional isomers).

The resulting purified compositions are preferably substantially free of proteins that do not have antiretroviral activity. In addition, the compositions preferably are substantially free of all other non-covalently attached water-soluble polymers.

Assessment of Activity

The antiviral activity of the conjugates and compositions of the invention may be determined using a suitable in-vivo or in-vitro model, depending upon the known activity of the particular EI employed. Methods for determining the antiviral activity of an EI conjugate or composition of the invention include cell fusion assays, cell free virus infection assays, reverse transcriptase assays, etc., all suitable indicators of anti-retroviral activity. Methods useful for determining the antiviral activity of any of the T-20 or T-20-related sequences described herein, or the activity of a corresponding polymer conjugate or composition, are described in U.S. Pat. No. 5,464,933. Additionally, an in-vivo assay suitable to determine antiviral activity is described in Example 16. As a standard for comparison, the IC50 of T-1249 per se is 0.003 µg/ml; its IC90 is 0.023 µg/ml. Additionally, T-20, when administered as a 90-mg single subcutaneous dose (N=12), exhibits a mean elimination half life of 3.8±0.6 h and a mean±SD apparent clearance of 24.8±4.1 mL/h/kg (Fuzeon™ Package Insert. The antiviral activity of conjugates or compositions of the anti-CCR5 murine monoclonal antibodies PA8, PA9, PA10, PA11, PA12, and PA 14 (PRO 140) is assessed, for example, using the gp120-sCD4 binding assay and RET assays (for detecting inhibition of envelope mediated membrane fusion and HIV-1 entry) described in Olson, W., et al., *J. of Virology*, May 1999, 73(5), 4145-4155, or by assessing the inhibition of HIV-1 replication in PBMC cultures or in macrophage cultures as described in Trkola, A., et al., *J. of Virology,* 2001, 75(2), 579-588. Polymer conjugates and compositions of sulfated CCR5 peptides are evaluated for antiviral activity using a solid phase ELISA for detecting complex peptide binding as described in U.S. Patent Application Publication No. 2003/0139571. Polymer conjugates and compositions of CD4-IgG2 chimeras are examined for antiviral activity using, for example, an ELISA method to evaluate binding affinity for monomeric gp120, and/or a virus-free syncytium assay to examine inhibition of HIV-1 envelope mediated syncytium formation, and/or neutralization studes using laboratory adapted strains and primary isolates of HIV-1, as provided in U.S. Pat. No. 6,451,313.

Pharmaceutical Compositions

Optionally, the compositions of the invention may further comprise one or more pharmaceutically acceptable excipients to provide a pharmaceutical composition. Exemplary excipients include, without limitation, carbohydrates, inorganic salts, antimicrobial agents, antioxidants, surfactants, buffers, acids, bases, and combinations thereof. Excipients suitable for injectable compositions include water, alcohols, polyols, glycerine, vegetable oils, phospholipids, and surfactants.

A carbohydrate such as a sugar, a derivatized sugar such as an alditol, aldonic acid, an esterified sugar, and/or a sugar polymer may be present as an excipient. Specific carbohydrate excipients include, for example: monosaccharides, such as fructose, maltose, galactose, glucose, D-mannose, sorbose, and the like; disaccharides, such as lactose, sucrose, trehalose, cellobiose, and the like; polysaccharides, such as raffinose, melezitose, maltodextrins, dextrans, starches, and the like; and alditols, such as mannitol, xylitol, maltitol, lactitol, xylitol, sorbitol (glucitol), pyranosyl sorbitol, myo-inositol, and the like.

The excipient can also include an inorganic salt or buffer such as citric acid, sodium chloride, potassium chloride, sodium sulfate, potassium nitrate, sodium phosphate monobasic, sodium phosphate dibasic, and combinations thereof.

The composition can also include an antimicrobial agent for preventing or deterring microbial growth. Nonlimiting examples of antimicrobial agents suitable for the present invention include benzalkonium chloride, benzethonium chloride, benzyl alcohol, cetylpyridinium chloride, chlorobutanol, phenol, phenylethyl alcohol, phenylmercuric nitrate, thimersol, and combinations thereof.

An antioxidant can be present in the composition as well. Antioxidants are used to prevent oxidation, thereby preventing the deterioration of the conjugate or other components of the preparation. Suitable antioxidants for use in the present invention include, for example, ascorbyl palmitate, butylated hydroxyanisole, butylated hydroxytoluene, hypophosphorous acid, monothioglycerol, propyl gallate, sodium bisulfite, sodium formaldehyde sulfoxylate, sodium metabisulfite, and combinations thereof.

A surfactant can be present as an excipient. Exemplary surfactants include: polysorbates, such as "Tween 20" and "Tween 80," and pluronics such as F68 and F88 (both of which are available from BASF, Mount Olive, N.J.); sorbitan esters; lipids, such as phospholipids such as lecithin and other phosphatidylcholines, phosphatidylethanolamines (although preferably not in liposomal form), fatty acids and fatty esters; steroids, such as cholesterol; and chelating agents, such as EDTA, zinc and other such suitable cations.

Acids or bases can be present as an excipient in the composition. Nonlimiting examples of acids that can be used include those acids selected from the group consisting of hydrochloric acid, acetic acid, phosphoric acid, citric acid, malic acid, lactic acid, formic acid, trichloroacetic acid, nitric acid, perchloric acid, phosphoric acid, sulfuric acid, fumaric acid, and combinations thereof. Examples of suitable bases include, without limitation, bases selected from the group consisting of sodium hydroxide, sodium acetate, ammonium hydroxide, potassium hydroxide, ammonium acetate, potassium acetate, sodium phosphate, potassium phosphate, sodium citrate, sodium formate, sodium sulfate, potassium sulfate, potassium fumerate, and combinations thereof.

The amount of the conjugate (i.e., the conjugate formed between the EI and the polymeric reagent) in the composition will vary depending on a number of actors, but will optimally be a therapeutically effective dose when the composition is stored in a unit dose container (e.g., a vial). In addition, the pharmaceutical preparation can be housed in a syringe. A therapeutically effective dose can be determined experimentally by repeated administration of increasing amounts of the conjugate or composition in order to determine which amount produces a clinically desired endpoint.

The amount of any individual excipient in the composition will vary depending on the activity of the excipient and particular needs of the composition. Typically, the optimal amount of any individual excipient is determined through routine experimentation, i.e., by preparing compositions containing varying amounts of the excipient (ranging from low to high), examining the stability and other parameters, and then determining the range at which optimal performance is attained with no significant adverse effects.

Generally, however, the excipient will be present in the composition in an amount of about 1% to about 99% by weight, preferably from about 5% to about 98% by weight, more preferably from about 15 to about 95% by weight of the excipient, with concentrations less than 30% by weight most preferred.

These foregoing pharmaceutical excipients along with other excipients are described in "Remington: The Science & Practice of Pharmacy", $19^{th}$ ed., Williams & Williams, (1995), the "Physician's Desk Reference", $52^{nd}$ ed., Medical Economics, Montvale, N.J. (1998), and Kibbe, A. H., Handbook of Pharmaceutical Excipients, $3^{rd}$ Edition, American Pharmaceutical Association, Washington, D.C., 2000.

The compositions encompass all types of formulations and in particular those that are suited for injection, e.g., powders or lyophilates that can be reconstituted as well as liquids. Examples of suitable diluents for reconstituting solid compositions prior to injection include bacteriostatic water for injection, dextrose 5% in water, phosphate-buffered saline, Ringer's solution, saline, sterile water, deionized water, and combinations thereof. With respect to liquid pharmaceutical compositions, solutions and suspensions are envisioned.

Preferably, the EI compositions described herein are in unit dosage form, meaning an amount of a conjugate or composition of the invention appropriate for a single dose, in a premeasured or pre-packaged form.

Administration

The compositions of the present invention are typically, although not necessarily, administered via injection and are therefore generally liquid solutions or suspensions immediately prior to administration. The pharmaceutical preparation can also take other forms such as syrups, creams, ointments, tablets, powders, and the like. Other modes of administration are also included, such as pulmonary, rectal, transdermal, transmucosal, oral, intrathecal, subcutaneous, intra-arterial, and so forth.

The invention also provides a method for administering a conjugate as provided herein to a patient suffering from a condition that is responsive to treatment with conjugate. The method comprises administering, generally via injection, a therapeutically effective amount of the conjugate (preferably provided as part of a pharmaceutical composition). As previously described, the conjugates can be administered injected parenterally by intravenous injection, or less preferably by intramuscular or by subcutaneous injection. Suitable formulation types for parenteral administration include ready-for-injection solutions, dry powders for combination with a solvent prior to use, suspensions ready for injection, dry insoluble compositions for combination with a vehicle prior to use, and emulsions and liquid concentrates for dilution prior to administration, among others.

The method of administering may be used to treat any condition that can be remedied or prevented by administration of an EI conjugate. Those of ordinary skill in the art appreciate which conditions a specific conjugate can effectively treat. For example, the conjugates can be used to treat individuals infected with HIV. The actual dose to be administered will vary depend upon the age, weight, and general condition of the subject as well as the severity of the condition being treated, the judgment of the health care professional, and conjugate being administered. Therapeutically effective amounts can be determined by those skilled in the art, and will be adjusted to the particular requirements of each particular case. Generally, a therapeutically effective amount will range from about 0.001 mg to 300 mg of EI, preferably in doses from 0.01 mg/twice daily to 200 mg/twice daily, preferably in doses from about 0.01 mg/day to 200 mg/day, and more preferably in doses from 0.10 mg/day to 100 mg/day.

The unit dosage of any given conjugate (again, preferably provided as part of a pharmaceutical preparation) can be administered in a variety of dosing schedules depending on the judgment of the clinician, needs of the patient, and so forth. The specific dosing schedule will be known by those of ordinary skill in the art or can be determined experimentally using routine methods. Exemplary dosing schedules include, without limitation, administration five times a day, four times a day, three times a day, twice daily, once daily, three times weekly, twice weekly, once weekly, twice monthly, once monthly, and any combination thereof. Preferred conjugate and compositions are those requiring dosing less frequently than once a day. That is to say, preferably, the composition of the invention is administered twice daily, once daily, once every other day, twice a week, once a week, once every two weeks, or once a month. Even more preferred are conjugates and compositions that are administered no more frequently than once a week, even more preferably no more frequently than twice monthly (every two weeks).

One advantage of administering certain conjugates of the present invention is that individual water-soluble polymer portions including the entire polymer can be cleaved off. Such a result is advantageous when clearance from the body is potentially a problem because of the polymer size. Optimally, cleavage of each water-soluble polymer portion is facilitated through the use of physiologically cleavable and/or enzymatically degradable linkages such as urethane, carbonate or ester-containing linkages. In this way, clearance of the conjugate (via cleavage of individual water-soluble polymer portions) can be modulated by selecting the polymer molecular size and the type functional group that provides the desired clearance properties. One of ordinary skill in the art can determine the optimal molecular size of the polymer as well as the cleavable functional group. For example, one can determine a preferred polymer molecular size, structure, and/or cleavable functional group by preparing a variety of polymer derivatives with different polymer weights and cleavable functional groups, and then conducting in-vitro or in vivo assays as described herein to assess efficacy. Alternatively, clearance profiles may be obtained (e.g., through periodic blood or urine sampling) using suitable in-vivo models.

The EI conjugates and compositions of the invention may be co-administered with one or more additional anti-viral or anti-retroviral agents in an approach typically referred to as combination therapy. Other antiviral agents thay may be present in the compositions of the invention, or alternatively may be co-administered, include DP107, rIFNα, rIFNβ, rIFNγ, AZT, 3TC, d4T, ddI, adefovir, abacavir, delaviridine mesylate, nevirapine, efavirenz, ribavirin, ritonavir, nelfinavir mesylate, amprenavir, saquinavir, indinavir, ABT538, amphotericin B, and castanospermine, or any of the herein-described EIs.

It is to be understood that while the invention has been described in conjunction with preferred specific embodiments, the foregoing description as well as the examples that follow are intended to illustrate and not limit the scope of the invention. Other aspects, advantages and modifications within the scope of the invention will be apparent to those skilled in the art to which the invention pertains.

All articles, books, patents and other publications referenced herein are hereby incorporated by reference in their entireties.

ABBREVIATIONS

| | |
|---|---|
| EI | entry inhibitor |
| AIDS | acquired immunodeficiency syndrome |
| HIV | human immunodeficiency virus |
| NRTI | nucleoside reverse transcriptase inhibitor |
| PI | protease inhibitor |
| NNRTI | non-nucleoside reverse transcriptase inhibitor |
| AZT | azidothymidine (also referred to as zidovudine or 3'-azido-3'-deoxythymidine) |
| PEG | polyethylene glycol |
| trt | trityl |
| Boc | t-butyloxycarbonyl |
| PBS | phosphate buffered saline |
| Troc | 2,2,2-trichloroethylcarbamate |
| Teoc | 2-trimethylsilylethyl carbamate |
| TEA | triethylamine |
| DMAP | 4-dimethylaminopyridine |
| DIC | 1,3-Diisopropylcarbodiimide |
| DCC | dicyclohexylcarbodiimide |
| DCM | dichloromethane |
| TFA | trifluoroacetic acid |
| PTSA | p-toluenesulfonic acid |
| 4-arm PEG-SCM | |

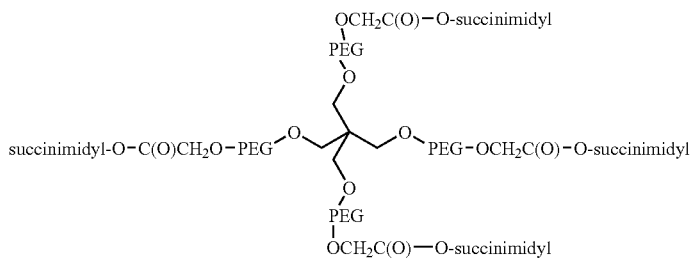

EXAMPLES

Materials

All chemical reagents referred to in the appended examples are commercially available or can be prepared based on information available in the art unless otherwise indicated.

All PEG reagents referred to in the appended examples are available from Nektar, Huntsville, Ala., unless otherwise indicated. All $^1$H NMR data was generated by a 300 or 400 MHz NMR spectrometer manufactured by Bruker.

Example 1

PEGylation of T1249 with mPEG-succinimidyl Benzamid-Carbonate 20 kDa (mPEG-SBC 20 kDa) in an Aqueous Reaction

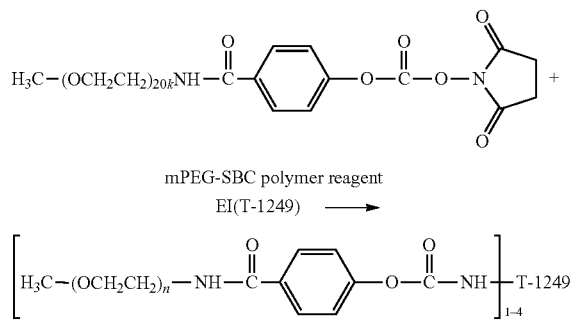

mPEG-SBC 20 kDa, available from Nektar Therapeutics (Huntsville, Ala.), stored at −20° C. under argon, was warmed to ambient temperature. The reaction was performed at room temperature. The calculated quantity of the warmed mPEG-SBC 20 kDa (414 mg, to obtain an 8-fold molar excess of mPEG-SBC 20 kDa based upon absolute peptide content) was weighed into a 5 mL glass vial containing a magnetic stirrer bar. A 2.0 mL aliquot of a 4.5 mg/mL solution of T1249 peptide (N-terminus acetylated; C-terminus modified with an amide group; prepared in phosphate buffered saline, PBS, pH 7.4) was added and the volume brought to 4.5 mL with additional PBS. The mixture was stirred at maximum speed using a magnetic stirrer until the PEG had fully dissolved. The stirring speed was reduced to 50% and the reaction allowed to proceed for 2½ hours resulting in a conjugate solution. The pH of the conjugate solution at the end of the reaction was 6.1 and was further reduced to 5.5 with 0.1 M HCl.

The conjugate solution was analyzed by SDS-PAGE (FIG. 1, lane 4) and RP-HPLC (C18). As can be seen in FIG. 1, the aqueous reaction did not go to completion as there is free peptide, mono-, di-, and tri-PEGylated material visible.

Example 2

PEGylation of T1249 with mPEG-Succinimidyl Benzamid-Carbonate, 20 kDa in a DMSO Reaction Mixture mPEG-succinimidyl benzamid-carbonate, 20 kDa, stored at −20° C. under argon, was warmed to ambient temperature. The reaction was performed at room temperature. Three different molar ratios (1:1, 1:2, and 1:4 of peptide: mPEG-SBC 20 kDa) were used. The calculated quantities of the warmed mPEG-SBC 20 kDa (29 mg, 58 mg, and 116 mg for 1:1, 1:2 and 1:4 ratios respectively) were weighed into glass vials in Example 1 above. In each vial the PEG-SBC 20 kDa was dissolved (by stirring) in 1 mL of DMSO before adding a 1 mL aliquot of a 5 mg/mL T1249 peptide solution also dissolved in DMSO. The reaction was allowed to continue for 3 hours resulting in a conjugate solution.

The conjugate solution was analyzed by SDS-PAGE (FIG. 1, lane 3, 4:1 molar ratio) and RP-HPLC. As can be seen in FIG. 1, lane 3, the conjugation reaction went to completion as there is no free peptide remaining, and mostly tri- and higher PEGmers visible (above the 66.3 kDa marker).

Example 3

PEGylation of T1249 with mPEG-Succinimidyl Benzamid-Carbonate, 20 kDa in a 1:1 Aqueous/DMSO Reaction mPEG-succinimidyl benzamid-carbonate, 20 kDa, stored at −20° C. under argon, was warmed to ambient temperature. The reaction was performed at room temperature as described in Example 2 above, with the exception that the peptide was dissolved in 1×PBS.

Figure 2:
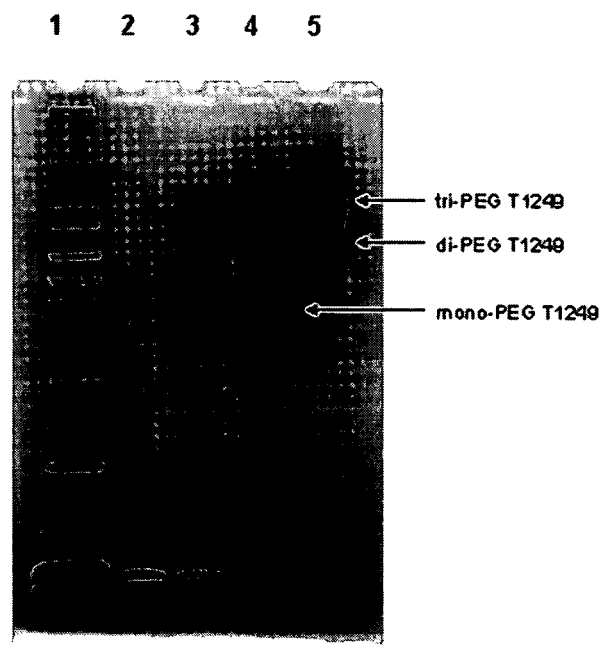

To summarize the experiments described in Examples 1-3 above, reactions were conducted using molar ratios of 1:1, 2:1 and 4:1, using both the aqueous/DMSO mixed reaction (Example 3) and the pure DMSO reaction conditions (Example 2); the results were similar for both methods. Typical results are shown in FIG. 2. The highest yield of mono-PEGylated a peptide was obtained with the 1:1 ratio (lane 3) where >50% of the product was monoPEGylated. Traces of tetra-PEGylated conjugate can be seen in FIG. 2 above the indicated tri-PEGylated material.

Figure 3:
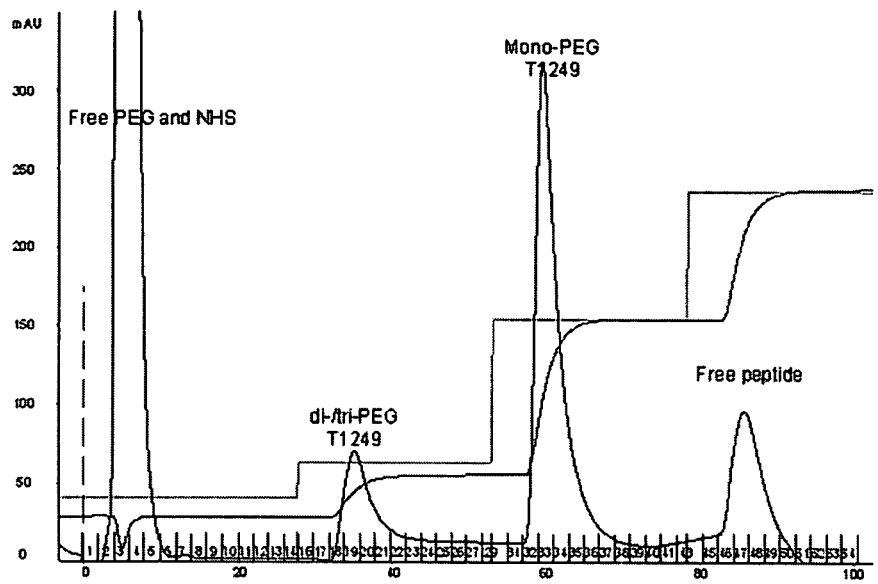

FIG. 3 illustrates an HPLC chromatogram for the conjugate mixture from Example 3, 1:1 molar ratio. A calculation of the areas under the curve indicated a yield of 51% monoPEG T1249, 17% di- and triPEG T1249 and 32% free peptide, prior to any additional purification. The sample injected was a 1:1 molar ratio in an aqueous/DMSO reaction and showed a pepide and product distribution similar to that in lane 3 of FIG. 2.

Example 4

Analysis of Conjugate Mixtures

The conjugate solutions prepared in Examples 1, 2 and 3 were analyzed by SDS PAGE.
SDS-PAGE Peptides and conjugates were resolved on 4-12% Novex Bis-Tris gels (Invitrogen) using MES buffer. Electrophoresis run-time was 35 min. Gels were stained with Simply Blue gel stain (Invitrogen), according to the manufacturer's instructions. Protein standard MARK 12 (Invitrogen) was used on all gels.

Example 5

Purification of Illustrative PEG-EI Conjugate Mixtures

Additional purification was conducted on the conjugate composition from Example 3 (mixed aqueous/DMSO reaction, 1:1 molar ratio).

A. Anion Exchange Chromatography.

The PEGylated forms of T1249 from Example 3 were purified using a 5 ml Q-HP column (Pharmacia). Two buffers were used in the purification: Buffer A was 20 mM MES pH 6.0 and buffer B was 20 mM MES pH 6.0 and 0.5 M NaCl. An Akta Purifier (Pharmacia) was used for the purification. A 5 ml Q-HP column (Pharmacia) was equilibrated in 14% B (in all cases the buffer A concentration was 100-% B). A sample was injected and the non-binding fraction allowed to elute by pumping 5 column volumes of 14% B through the column. PEGylated T1249 containing 2 or more PEG moieties ("himers") were eluted from the column by increasing the buffer B content to 17% (5 column volumes). The monoPEGylated form was eluted by raising the buffer B content to 45% (5 column volumes). Finally the buffer B content was raised to 70% (5 column volumes) to elute non-PEGylated T1249. Fractions were collected and analyzed by SDS PAGE.

Figure 4:
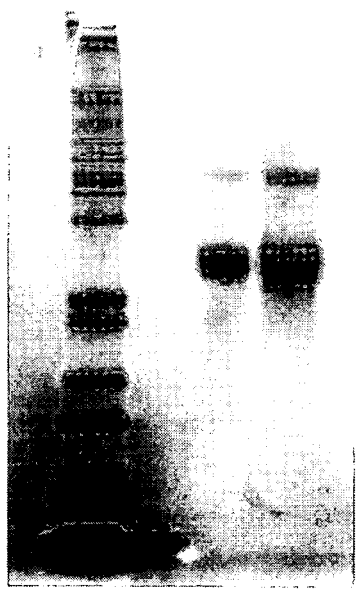

An SDS PAGE of the mono-PEGylated pool is shown in FIG. 4. A low level (<10%) of di- and tri-PEGylated material was present in the pooled material.

Additional purification is carried out to remove the remainder of di- and tri-PEGylated material.

B. Amicon Concentration

Chromatographic fractions containing monoPEG-T1249 were pooled and concentrated by Amicon filtration (YM 10 membrane, 10,000 MWCO) (Millipore).

C. HPLC Method

A Zorbax 80A Extend-C18 column (Agilent) 4.6×250 mm was used with an Agilent 1100 HPLC. Mobile phase A was 0.1% TFA in milli-Q water and mobile phase B was 0.1% TFA in acetonitrile. The column was maintained at a temperature of 58° C. The timetable was as follows:

| Time, minutes | % A | % B |
| --- | --- | --- |
| 0 | 55 | 45 |
| 4 | 55 | 45 |
| 24 | 45 | 55 |
| 25 | 0 | 100 |
| 26 | 0 | 100 |
| 27 | 55 | 45 |

The method included a 4 minute post-time.

Under the conditions described, the free T1249 peptide had a retention time of 4.5±0.1 minutes. Free PEG had a retention time of 18.0±0.1 minutes. The purified monoPEGylated preparation showed two main peaks at 19.8 and 20.6 minutes. These peaks presumably correspond to two positional isomers of monoPEGylated material. The di- and tri-PEGylated material eluted in two peaks with retention times of 21.6 and 22.6 minutes, respectively.

D. Degradation of MonoPEGylated T1249

A sample (450 μl) of the monoPEGylated T1249 was combined with 1/10 volume (50 μl) of 10×PBS. The pH was raised to 7.4 and the sample incubated at 37° C. overnight. Samples were analyzed by HPLC.

Figure 5:
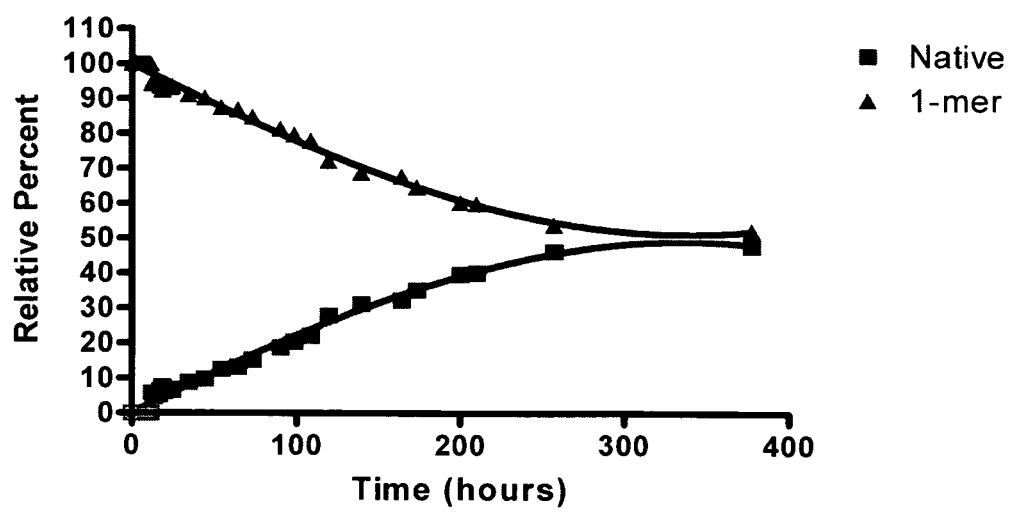

HPLC analysis confirmed hydrolysis of the conjugate sample in-vitro. A plot illustrating hydrolysis of a model peptide-SPC mono-PEG conjugate in vitro, i.e., in PBS at pH 7.4 and 37° C., is provided in FIG. 5. As can be seen from the figure, as the mono-PEG conjugate hydrolyses, free peptide appears as determined by HPLC analysis. At 384 hours (i.e., 16 days), approximately 50% of the conjugate has hydrolyzed to release free peptide, demonstrating a representative sustained release profile of the conjugates provided herein.

In the above illustrative examples, it appeared that only 3 of the 4 lysines were readily available for PEGylation—the 4:1 ratio reactions in either DMSO alone or the mixed reactions (aqueous/DMSO) yielded mainly triPEGylated material when driven to completion, although traces of tetra-PEGylated material were observed. Two lysines (Lys 28 and 31) on T-1249 are only 2 amino acids apart, and PEGylation at either one could potentially affect PEGylation at the other site, e.g., due to steric hindrance.

In the ion exchange purification method employed, at least 3 monoPEGylated peaks were deliberately combined into one. These individual peaks represent positional isomers, which can be further purified and characterized by peptide mapping if desired.

Example 6

PEGylation of T1249 with mPEG-Succinimidyl Benzamid-Carbonate 30 kDa (mPEG-SBC 30 kDa)

T-1249 is PEGylated as described in Examples 1-3 above using various solvent systems (aqueous, DMSO, aqueous DMSO), with the exception that the PEG reagent employed has a molecular weight of 30 kDa. The resulting conjugate mixture is analyzed and further purified as described in Examples 4 and 5 above.

Example 7

PEGylation of T1249 with mPEG-Succinimidyl benzamid-carbonate 40 kDa (mPEG-SBC 40 kDa)

T-1249 is PEGylated as described in Examples 1-3 above using various solvent systems (aqueous, DMSO, aqueous DMSO), with the exception that the PEG reagent employed has a molecular weight of 40 kDa. The resulting conjugate mixture is analyzed and further purified as described in Examples 4 and 5 above.

Example 8

PEGylation of T1249 with mPEG-Succinimidyl Phenyl-Carbonate 20 kDa (mPEG-SPC 20 kDa) in an Aqueous Reaction

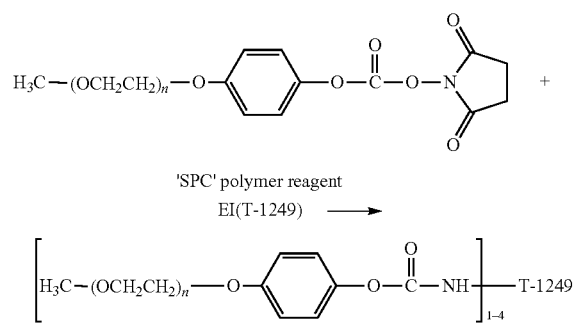

mPEG-SPC 20 kDa, available from Nektar Therapeutics (Huntsville, Ala.), stored at −20° C. under argon, is warmed to ambient temperature. The reaction is performed at room temperature. An absolute 8-fold molar excess of mPEG-SPC reagent is used, based upon absolute peptide content). The PEG reagent is weighed into a 5 mL glass vial containing a magnetic stirrer bar. A 2.0 mL aliquot of a 4.5 mg/mL solution of T1249 peptide (N-terminus acetylated; C-terminus modified with an amide group; prepared in phosphate buffered saline, PBS, pH 7.4) is added and the volume brought to 4.5 mL with additional PBS. The mixture is stirred at maximum speed using a magnetic stirrer until the PEG is fully dissolved. The stirring speed is reduced to 50% and the reaction is allowed to proceed for about 2½ to 3 hours to result formation of conjugate product. The pH of the conjugate solution at the end of the reaction is measured and further acidified by addition of 0.1M HCl if necessary to bring the pH of the final solution to about 5.5.

The conjugate solution is then analyzed by SDS-PAGE and RP-HPLC (C18) to determine the extent of reaction (i.e., whether the reaction has gone to completion).

Additional reactions, conducted as described above, are carried out with (i) mPEG-SPC 30 kDa, and (ii) mPEG-SPC 40 kDa, available from Nektar Therapeutics, Huntsville, Ala.

Example 9

PEGylation of T1249 with mPEG-Succinimidyl Phenyl-Carbonate 20 kDa (mPEG-SPC 20 kDa) in a DMSO Reaction Mixture mPEG-succinimidyl phenyl-carbonate, 20 kDa, stored at −20° C. under argon, is warmed to ambient temperature. The reaction is performed at room temperature. Three different molar ratios (1:1, 1:2, and 1:4 of peptide: mPEG-SPC 20 kDa) are used. The corresponding calculated quantities of the warmed mPEG-SPC 20 kDa (for 1:1, 1:2 and 1:4 ratios respectively) are weighed into glass vials as in Example 8 above. In each vial the PEG-SPC 20 kDa is dissolved (by stirring) in 1 mL of DMSO before adding a 1 mL aliquot of a 5 mg/mL T1249 peptide solution also dissolved in DMSO. The reaction is allowed to continue for about 3-5 hours to result in a conjugate solution.

The resulting conjugate solution for each reaction is then analyzed by SDS-PAGE and RP-HPLC to determine the extent of reaction.

Example 10

PEGylation of T1249 with mPEG-Succinimidyl Phenyl-Carbonate, 20 kDa in a 1:1 Aqueous/DMSO Reaction mPEG-succinimidyl phenyl-carbonate, 20 kDa, stored at −20° C. under argon, is warmed to ambient temperature. The reaction is performed at room temperature as described in Example 9 above, with the exception that the peptide is dissolved in 1×PBS.

Additional analysis, purification, and hydrolysis of the product compositions from Examples 8-10 is conducted as described in Examples 4 and 5 above.

Examples 11-15 are related to the generalized scheme provided below. In this approach a degradable linkage is introduced into the final conjugate structure via attachment of a linker, in this instance, an exemplary amino acid, glycine, attached to the peptide drug via a degradable ester linkage. The following examples describe the synthetic steps for producing entry inhibitor conjugates in accordance with this aspect of the invention.

Illustrative Reaction Scheme:

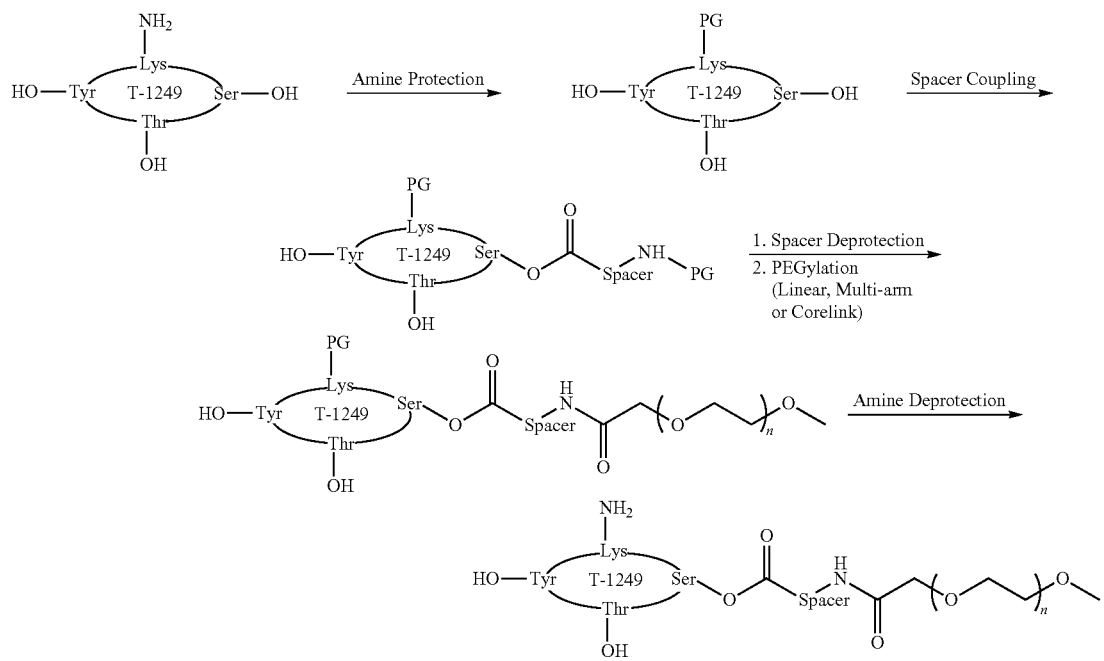

The above reaction scheme, specific for T-1249, is applicable to other entry inhibitors as described herein, such that the designation "T-1249" in the above scheme is replaceable by the generalized term, "EI", entry inhibitor.

Example 11

Initial Protection of T-1249 Primary Amino Groups

Nε-Troc-T-1249: To a stirred solution of peptide, T-1249, in water (30 mL/g peptide drug) and tetrahydrofuran (THF, 12 mL/g peptide) is added triethylamine (TEA, 20 eq) and 2,2,2-trichloroethyl succinimidyl carbonate (Troc-OSu, 20 eq). The mixture is stirred at room temperature for 16 h. After the solution is acidified with concentrated hydrochloric acid (HCl) to pH 4-6, the organic solvent is removed under reduced pressure, and the aqueous layer is lyophilized to dryness. The residue is then precipitated in diethyl ether (300 mL/g peptide). The ether is decanted off after centrifugation of the peptide for 5 min at 12,000 rpm and the precipitate is washed with cooled diethyl ether (2×100 mL/g peptide). Alternatively, the product is collected by suction filtration and washed with cooled diethyl ether (2×100 mL/g peptide). Additional purification is carried out as required based upon initial analysis, e.g., by preparative HPLC. The drug product Nε-Troc-T-1249 is dried in vacuo overnight. Characterization by mass spectrometry (MS) and purity is determined by HPLC.

Nε-Teoc-T-1249: Protection is of the amine groups is conducted as described above for Nε-Troc-T-1249, with the exception that a different protecting group, 1-[(2-trimethylsilyl)ethoxycarbonyloxy]pyrrolidin-2,5-dione (Teoc-OSu), is employed.

Example 12

Addition of a Protected Amino Acid Spacer to Amine-Protected T-1249

Among the three different hydroxyl groups (serine, threonine, and tyrosine) present in the T-1249 backbone, the serine primary hydroxyl group is expected to exhibit the highest reactivity, although reaction conditions can be adjusted to favor substitution on the other forementioned sites.

$N^\alpha$-Boc-Gly-$N^\epsilon$-Troc-T-1249: $N^\epsilon$-Troc-T-1249 is dissolved in dichloromethane (DCM, 35 mL/g peptide) and a small amount of dimethyl sulfoxide (DMSO, <3 mL/g peptide) is added to increase the peptide solubility. $N^\alpha$-tert-butoxycarbonylglycine ($N^\alpha$-Boc-glycine-OH, 1.2 eq) and 4-dimethylaminopyridine (DMAP, 1.2 eq) are added and the reaction is stirred at room temperature for approximately 10 minutes. 1,3-Diisopropylcarbodiimide (DIC, 2 eq) is added and the reaction is allowed to continue at room temperature for approximately 16 h. The DCM solution is concentrated under reduced pressure and the residue is precipitated using diethyl ether cooled in an ice bath (300 mL/g peptide). The organic phase is decanted off after centrifugation of the peptide for 5 min at 12,000 rpm and the precipitate is washed with cooled diethyl ether (2×80 mL/g peptide). Alternative to centrifugation, the product is collected by suction filtration and washed with cooled diethyl ether (2×100 mL/g drug), followed by optional additional purification by preparative HPLC, as warranted based upon the analysis of the product. The peptide product $N^\alpha$-Boc-Gly-$N^\epsilon$-Troc-T-1249 is dried in vacuo overnight. Characterization is carried out by mass spectrometry (MS), while product purity is determined by HPLC.

Example 13

Deprotection of the Spacer in $N^A$-Boc-GLY-$N^\epsilon$-TROC-T-1249

A. Gly-$N^\epsilon$-Troc-T-1249: $N^\alpha$-Boc-Gly-$N^\epsilon$-Troc-T-1249 is dissolved in DCM (30 mL/g peptide) and a small amount of DMSO (<3 mL/g peptide) is added to increase the solubility of the peptide. Anhydrous trifluoroacetic acid (TFA, 4 mL/g peptide) is added and the reaction is stirred at room temperature for 2 h. The TFA/DCM solvents are removed under reduced pressure and the residue is washed with diethyl ether (2×80 mL/g peptide) and evaporated to dryness each time before it is precipitated in diethyl ether (300 mL/g peptide). The organic phase is decanted off after centrifugation of the peptide for 5 min at 12,000 rpm and the precipitate is washed with cooled diethyl ether (2×100 mL/g peptide). Alternative to centrifugation, the product is collected by suction filtration and washed with cooled diethyl ether (2×100 mL/g peptide). Additional purification may be carried out, e.g., by preparative HPLC, if necessary. The product Gly-$N^\epsilon$-Troc-T-1249 TFA salt is dried in vacuo overnight. Characterization is carried out by mass spectrometry (MS) and purity is determined by HPLC.

B. Gly-$N^\epsilon$-Troc-T-1249: $N^\alpha$-Boc-Gly-$N^\epsilon$-Troc-T-1249 is dissolved in a mixture of THF (40 mL/g) and DMSO (5 mL/g peptide). A solution of p-toluenesulfonic acid (PTSA, 1.0 eq) in ethanol (6 mL/g drug) is added. The solution is placed on a rotary evaporator and the solvent mixture is removed. The bath temperature is raised to 60-65° C. and the temperature maintained for an additional 20 min. Upon being cooled to room temperature, the residue is precipitated in diethyl ether (300 mL/g drug). The organic phase is decanted off after centrifugation of the peptide for 5 min at 12,000 rpm and the precipitate is washed with cooled diethyl ether (2×100 mL/g drug). Alternative to centrifugation, the product is collected by suction filtration and washed with cooled diethyl ether (2×100 mL/g drug). Additional purification is optionally carried out, e.g., by preparative HPLC. The product, Gly-$N^\epsilon$-Troc-T-1249 PTSA salt, is dried in vacuo overnight. Characterization is conducted by mass spectrometry (MS) and purity is determined by HPLC.

Example 14

Covalent Attachment of Gly-$N^\epsilon$-Troc-T-1249 to Exemplary PEG Reagents to Provide Degradable PEG-T-1249 Conjugates a.1) Linear PEG Conjugate ($CH_3O$—$(CH_2CH_2O)_{20kD}$—$CH_2C(O)$—NH-Gly-$N^\epsilon$-Troc-T-1249, where "NH-Gly" indicates covalent attachment to the glycine amino group): Gly-$N^\epsilon$-Troc-T-1249 salt from Example 13 above is dissolved in DCM (30 mL/g drug) and a small amount of DMSO (<3 mL/g drug) is added to increase the drug solubility. Triethylamine (TEA, 10 eq) is added and the reaction solution is stirred at room temperature for 5 min. $PEG_{20kD}$-SCM (1 eq), $CH_3O$—$(CH_2CH_2O)_{20kD}$—$CH_2C(O)$-succinimide) in DCM (10 mL/g drug) is added and the reaction is allowed to progress at room temperature for about 16 h. The solvent is removed under reduced pressure and the residue is precipitated by adding diethyl ether (300 mL/g drug). The desired product, abbreviated as $PEG_{20kD}$-Gly-$N^\epsilon$-Troc-T-1249 (where the actual structure is shown above), is collected after suction filtration and dried under vacuum overnight.

a.2) Linear PEG Conjugate ($CH_3O$—$(CH_2CH_2O)_{30kD}$—$CH_2C(O)$—NH-Gly-$N^\epsilon$-Troc-T-1249): Gly-$N^\epsilon$-Troc-T-1249 salt from Example 13 above is dissolved in DCM (30 mL/g drug) and a small amount of DMSO (<3 mL/g drug) is added to increase the drug solubility. Triethylamine (TEA, 10 eq) is added and the reaction solution is stirred at room temperature for 5 min. $PEG_{30kD}$-SCM (1 eq), $CH_3O$—$(CH_2CH_2O)_{30kD}$—$CH_2C(O)$—O-succinimide) in DCM (10 mL/g drug) is added and the reaction is allowed to progress at room temperature for about 16 h. The solvent is removed under reduced pressure and the residue is precipitated by adding diethyl ether (300 mL/g drug). The desired product, abbreviated as $PEG_{30kD}$-Gly-$N^\epsilon$-Troc-T-1249 (where the actual structure is shown above), is collected after suction filtration and dried under vacuum overnight.

a.3. Linear PEG Conjugate, $CH_3O$—$(CH_2CH_2O)_{30kD}$—$CH_2CH_2$—C(O)—NH-Gly-$N^\epsilon$-Troc-T-1249): Gly-$N^\epsilon$-Troc-T-1249 salt from Example 13 above is dissolved in DCM (30 mL/g drug) and a small amount of DMSO (<3 mL/g drug) is added to increase the drug solubility. Triethylamine (TEA, 10 eq) is added and the reaction solution is stirred at room temperature for 5 min. $PEG_{30kD}$-SPA (1 eq), PEG-succinimidyl propionate, $CH_3O$—$(CH_2CH_2O)_{30kD}$—$CH_2CH_2C$(O)—O-succinimide) in DCM (10 mL/g drug) is added and the reaction is allowed to progress at room temperature for about 16 h. The solvent is removed under reduced pressure and the residue is precipitated by adding diethyl ether (300 mL/g drug). The product, $CH_3O$—$(CH_2CH_2O)_{30kD}$—$CH_2CH_2$—C(O)—NH-Gly-$N^\epsilon$-Troc-T-1249), is collected after suction filtration and dried under vacuum overnight.

a.4. Linear PEG Conjugate, $CH_3O$—$(CH_2CH_2O)_{20kD}$—$CH_2CH_2$—C(O)—NH-Gly-$N^\epsilon$-Troc-T-1249): Gly-$N^\epsilon$-Troc-T-1249 salt from Example 13 above is dissolved in DCM (30 mL/g drug) and a small amount of DMSO (<3 mL/g drug) is added to increase the drug solubility. Triethylamine (TEA, 10 eq) is added and the reaction solution is stirred at room temperature for 5 min. $PEG_{20kD}$-SPA (1 eq), PEG-succinimidyl propionate, $CH_3O$—$(CH_2CH_2O)_{20kD}$—$CH_2CH_2C$(O)—O-succinimide) in DCM (10 mL/g drug) is added and the reaction is allowed to progress at room temperature for about 16 h. The solvent is removed under reduced pressure and the residue is precipitated by adding diethyl ether (300 mL/g drug). The product, $CH_3O$—$(CH_2CH_2O)_{20kD}$—$CH_2CH_2$—C(O)—NH-Gly-$N^\epsilon$-Troc-T-1249), is collected after suction filtration and dried under vacuum overnight.

a.5. Linear PEG Conjugate, $CH_3O$—$(CH_2CH_2O)_{30kD}$—$CH_2CH_2$—$CH_2$—C(O)—NH-Gly-$N^\epsilon$-Troc-T-1249): Gly-$N^\epsilon$-Troc-T-1249 salt from Example 13 above is dissolved in DCM (30 mL/g drug) and a small amount of DMSO (<3 mL/g drug) is added to increase the drug solubility. Triethylamine (TEA, 10 eq) is added and the reaction solution is stirred at room temperature for 5 min. $PEG_{30kD}$-SBA (1 eq), PEG-succinimidyl butanoate, $CH_3O$—$(CH_2CH_2O)_{30kD}$—$CH_2CH_2CH_2C$(O)—O-succinimide) in DCM (10 mL/g drug) is added and the reaction is allowed to progress at room temperature for about 16 h. The solvent is removed under reduced pressure and the residue is precipitated by adding diethyl ether (300 mL/g drug). The product, $CH_3O$—$(CH_2CH_2O)_{30kD}$—$CH_2CH_2CH_2$—C(O)—NH-Gly-$N^\epsilon$-Troc-T-1249), is collected after suction filtration and dried under vacuum overnight.

a.6. Linear PEG Conjugate, $CH_3O$—$(CH_2CH_2O)_{30kD}$—$CH_2CH_2$—CH($CH_3$)—C(O)—NH-Gly-$N^\epsilon$-Troc-T-1249): Gly-$N^\epsilon$-Troc-T-1249 salt from Example 13 above is dissolved in DCM (30 mL/g drug) and a small amount of DMSO (<3 mL/g drug) is added to increase the drug solubility. Triethylamine (TEA, 10 eq) is added and the reaction solution is stirred at room temperature for 5 min. $mPEG_{30KD}$-SMB (1 eq), mPEG-succinimidyl α-methylbutanoate, $CH_3O$—$(CH_2CH_2O)_{30KD}$—$CH_2CH_2CH(CH_3)C$(O)—O-succinimide) in DCM (10 mL/g drug) is added and the reaction is allowed to progress at room temperature for about 16 h. The solvent is removed under reduced pressure and the residue is precipitated by adding diethyl ether (300 mL/g drug). The product, $CH_3O$—$(CH_2CH_2O)_{30kD}$—$CH_2CH_2CH(CH_3)$—C(O)—NH-Gly-$N^\epsilon$-Troc-T-1249), is collected after suction filtration and dried under vacuum overnight.

b) Multi-Arm PEG (4-arm-$PEG_{20k}$-Gly-$N^\epsilon$-Troc-T-1249):

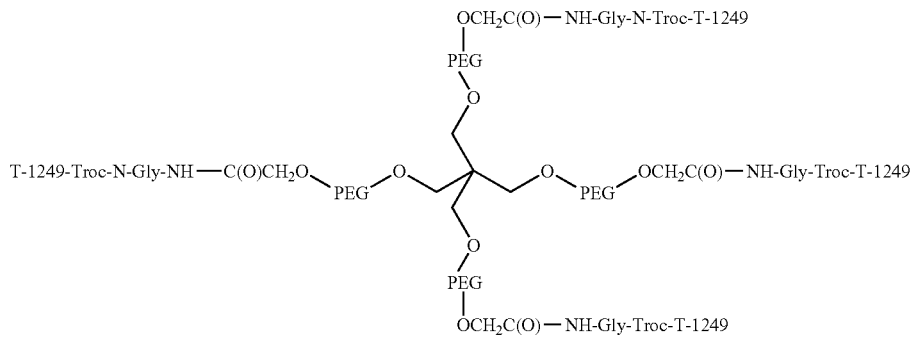

4-Arm-$PEG_{20k}$-SCM (see structure in Abbreviations section above) is dissolved in anhydrous methylene chloride. In a separate round bottom flask, Gly-$N^\epsilon$-Troc-T-1249 salt (1.0 equiv) is dissolved in DCM and treated with TEA, stirred at room temperature for 5 minutes. Then the T-1249 solution is added to the solution of 4-arm-$PEG_{20k}$-SCM in methylene chloride and the reaction is stirred at room temperature for approximately 15 h. The product, 4-arm-$PEG_{20k}$-Gly-$N^\epsilon$-Troc-T-1249, is precipitated in diethyl ether and collected by suction filtration. The purity and extent of peptide drug loading is determined by HPLC analysis.

c) "Corelink" (Corelink-Gly-$N^\epsilon$-Troc-T-1249):

The term "Corelink" corresponds to the structure below, a 4-arm PEG-PGA-PEG polymer system as described in International Patent Publication No. WO 04/060967, also referred to herein as 4-arm-PEG2K-PG-PEG10k (MW~47 k).

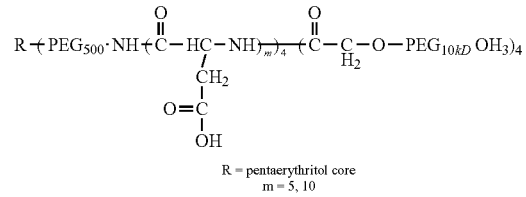

1. Synthesis of 4-arm PEG-NH$_2$. 4-arm-PEG (20 g, MW=2,000 Da) (Nektar Therapeutics, Huntsville Ala.) in toluene (100 ml) was azeoptroped until an oily consistency was obtained. The oily crude was dissolved in toluene (100 ml) along with triethylamine (12.9 ml) and stirred for five minutes. Methane sulfonyl chloride (6.5 ml) was then added to the solution, and the resulting solution was stirred for 16 hours at room temperature. After addition of ethanol, solvent was removed through rotary-evaporation and PEG-mesylate was dried overnight. Ammonium chloride (6 grams per gram of PEG) was dissolved in ammonium hydroxide (40 ml per gram of PEG), to which was added the PEG mesylate and the resulting solution stirred at room temperature for 48 hours. Sodium chloride (10% solution) was added to the solution, followed by extraction with dichloromethane. Solvent was removed and 4-arm-PEG-NH$_2$ was dried under vacuum. The product yield was approximately 85-90 percent.

2. Synthesis of Glu-NCA (BLG-NCA). Benzyl-L-glutamate, BLG (1.0 equiv) was dissolved in tetrahydrofuran (10 ml/gram) along with triphosgene (1.2 equiv). The solution was stirred for three hours at 60° C. Hexanes were then added to the solution to precipitate solid, which was then filtered. The recovered precipitate was dissolved in chloroform and precipitated once again with hexanes. The precipitate was then filtered and dried under vacuum. Yield: 90 percent yield.

3. Synthesis of PEG-PBLG. 4-arm-PEG$_{2K}$-NH$_2$ (700 mg) was azeotroped in toluene (50 ml) twice and then dried under vacuum overnight. 4-arm-PEG$_{2K}$-NH$_2$ (700 mg) was dissolved in dimethyl formamide (7 ml). BLG-NCA (3.68 g) from above was then added to the solution. The solution was stirred for three hours under nitrogen. A sample was then removed from solution and precipitated. The product was characterized through mixed-D and NMR methods to ensure formation of core, followed by PEGylation of the polymer with an activated PEG reagent, PEG-SCM, CH$_3$O—(CH$_2$CH$_2$O)$_{10kD}$—CH$_2$C(O)—O-succinimide. m-PEG10K-SCM (14 grams) was dissolved in dichloromethane, additionally containing dicyclohexylcarbodiimide (335 mg) and 4-(dimethylamino) pyridine (20 mg), to which was added the BLG-NCA solution from above. The resulting solution was stirred overnight at room temperature.

4. Debenzylation of PEG-PBLG to form "Corelink", 4-arm-PEG$_{2k}$-PG-PEG$_{10k}$ (MW~47 k). PEG-PBLG (16 grams) was dissolved in acetic acid (16 ml), deionized water (16 ml), and dimethylformamide (80 ml). To this solution was added ammonium formate (16 grams) and palladium/carbon (1.6 grams). The solution was stirred at room temperature for 48 hours, followed by filtration over a celite bed to remove the majority of carbon particles. The solution was then dialyzed in water to remove the solvent from solution. After ultrafiltration with a 30,000 MW filter, unbound PEG was removed from solution. The solution was then centrifuged at 20,000 RPM for 3 hours to remove the remainder of the carbon particles. The product yield was between 45 and 55 percent.

5. Corelink-Gly-N$^\epsilon$-Troc-T-1249). 4-arm-PEG$_{2k}$-PG-PEG$_{10k}$ (MW~47 k) is dissolved in DMF, into which N-hydroxysuccimide, and DCC is added at room temperature. The reaction is stirred overnight. Gly-N$^\epsilon$-Troc-T-1249 salt is dissolved in DMF and treated with TEA, then added to the multi-arm PEG reagent ("Corelink") solution. The reaction is stirred at room temperature for approximately 36 h and then is precipitated in diethyl ether. The resulting solid product is collected by suction filtration. The purity and extent of drug loading are determined by HPLC analysis.

Example 15

Final Deprotection of Degradable Gly-N$^\epsilon$-Troc-T-1249 PEG Conjugates For each of the conjugates in Example 14 (a.1 to a.6 through c above): The corresponding PEG$_n$-Gly-N$^\epsilon$-Troc-T-1249 is dissolved in a mixture of acetic acid-water-tetrahydrofuran (3:1:1) at room temperature and stirred for 24 h. The organic solvent is removed under reduced pressure and the water is removed by lyophilization. The resulting residue is first precipitated in diethyl ether and is further purified in methanol (10 mL/g drug) and IPA (30 mL/g drug). Purity and hydrolysis rates are determined by HPLC analysis.

For each of the conjugates in Example 14 (a.1 to a.6 through c above): PEG$_n$-Gly-N$^\epsilon$-Teoc-T-1249 is dissolved in a mixture of THF (30 mL/g drug) and potassium dihydrogen phosphate (1.0 M, 30 mL). Fresh zinc dust (60 eq) is added and the mixture is stirred at room temperature for 24 h before it is diluted with water (100 mL/g drug). The Zn solids are filtered and washed with THF. The organic solvent is removed under reduced pressure and the aqueous phase is extracted with DCM (3×25 mL/g). The combined organic phases are washed with ice-cold 5% NaOH (20 mL) and brine (20 mL), dried over MgSO$_4$, and the solvent is removed under reduced pressure. The resulting residue is first precipitated in ether; further purification is performed in methanol (10 mL/g drug) and IPA (30 mL/g drug). Purity and hydrolysis rates are determined by HPLC analysis.

Example 16

In-Vitro Assay to Assess Antiviral Activity

Assays which score for reduction of infectious virus titer employing the indicator cell lines, MAGI (Multinuclear Activation of a Galactosidase Indicator), or the CCR5-expressing derivative, cMAGI, are used to provide an indication of antiviral activity of the conjugates/compositions of the invention.

The MAGI cell line is derived from parental HeLa cells by introducing genes for CD4 and an HIV-1 LTR-driven β-gal reporter with an amphotropic retrovirus vector (as described in Kimpton J, Emerman M, *J Virol* 66:2232-9, 1992). The cMAGI cell line is derived from the MAGI cell line by introduction of the CCR5 gene using the amphotropic retroviral vector, PA317 (as described in Chackerian B, et al., *J Virol* 71:3932-9, 1997). The cMAGI cells support replication of primary NSI (R5) isolates and laboratory adapted X4 viruses, while the MAGI cells support replication of only X4 viruses. Both cell lines exploit the ability of HIV-1 tat to transactivate the expression of a β-galactosidase reporter gene driven by the HIV-LTR. The β-gal reporter is modified to localize in the nucleus and can be detected with the X-gal substrate as intense nuclear staining within a few days of infection. The number of stained nuclei are interpreted as equal to the number of infectious virions in the challenge inoculum if there is only one round of infection prior to staining.

An inhibitor of infection and cell-cell fusion, e.g., T-1249 or T-20 (Wild C, et al., *AIDS Res Hum Retroviruses*, 9:1051-3, 1993), or another EI as described herein, is added 24 hrs post-infection to permit a readout representing a single round of infection. Infected cells are enumerated using a CCD-imager. In the MAGI and cMAGI assays, a 50% reduction in infectious titer ($V_n/N_o$=0.5) is significant and provides the primary cutoff value for assessing antiviral activity. A 90% reduction in infectious titer ($V_n/N_o$) is used as an additional cutoff value in assessing antiviral activity.

Each test compound dilution is tested in duplicate against a virus inoculum adjusted to yield approximately 1500-2000 infected cells/well of a 48-well microtiter plate. The test compound is added to the cMAGI or MAGI cells, followed by the virus inocula, and 24 hrs later, a known inhibitor of infection and cell-cell fusion (Wild C, et al. *AIDS Res Hum Retroviruses* 9:1051-3,1993) is added to prevent secondary rounds of infection and cell-cell virus spread. The cells are typically cultured for 2 more days, fixed and stained with the X-gal substrate to detect infected cells. The number of infected cells for each control and test compound dilution are then determined with the CCD-imager, and the corresponding $IC_{50}$ and $IC_{90}$ values are then determined and compared to, for example, the entry inhibitor per se, absent polymer. Values are typically reported in μg/ml. $IC_{50}$ is defined as the dilution of a test compound resulting in a 50% reduction in infectious virus titer, and $IC_{90}$ is defined as the dilution resulting in a 90% reduction in infectious titer.

Example 17

Pharmacokinetics 9 male Wistar rats (Charles River Laboratories, Wilmington, Del.) (n=3/time point) receive a single subcutaneous dose of a polymer conjugate/composition of either T1249 or T-20 as described herein, e.g., in Examples 1, 2, 3, 6, 7, 8, 9, 10, and 11-15.

The test mPEG conjugate is mixed with normal saline or 5% dextrose injection. pH adjustments are made with dilute NaOH or HCl solutions to prepare drug solutions with pHs ranging from approximately 6.2-7.4 and osmolality of about 290 mOsm/kg. The amount of conjugate employed is sufficient to provide a concentration of approximately 50-250 mg conjugate per ml in the final formulation. The rats are dosed at 8 mg of active ingredient/kg body weight.

After dose administration, about 0.2 to 0.5 ml of blood is collected from the retro-orbital sinus at each time point. The time points are 0.5, 1, 3, 6, 8, 16, 24, 32, 48, 72, 96, and 120 hours following dose administration. Each sample is immediately processed to collect plasma or serum and stored at −70 C until analysis. Each sample is assayed by liquid chromatography using reverse phase methods that allow for the main analytes and metabolites to be detected by absorbance detection (280 nm) or by mass spectrometry (single or triple quad). Concentrations are extrapolated from a plot using conjugate and EI per se spiked serum extracts as calibration standards. Pharmacokinetic parameters are then derived from concentration versus time profiles using pooled serum concentration of conjugate, released EI, detectable metabolites, and combinations thereof. PK analysis parameters are reported from non-compartmental analysis using a commercial pharmacokinetic analysis software package, such as WIN-NONLIN available from Pharsight Corporation, Mountain View, Calif.

What is claimed is:

1. An HIV-entry inhibitor-water-soluble polymer conjugate having a structure:

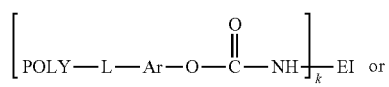

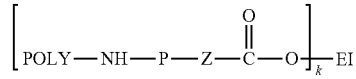

wherein:
EI is an HIV-entry inhibitor that corresponds to T-20 or T-1249,
POLY is a water-soluble, poly(alkylene oxide),
k is selected from 1, 2, and 3,
L is —O— or —NH—C(O)—,
Ar is an aromatic group,
—NH-EI in structure II represents an amino group of the EI,
P is a spacer,
Z is —O— or —NH—,
—O-EI in structure III represents a hydroxyl group of the EI,
and further wherein the poly(alkylene oxide) is covalently attached to the entry inhibitor by a hydrolyzable linkage effective to release the entry inhibitor upon hydrolysis.

2. The conjugate of claim 1, wherein each poly(alkylene oxide) is a poly(ethylene glycol).

3. The conjugate of claim 2, wherein each poly(ethylene glycol) is terminally capped with an end-capping moiety selected from the group consisting of hydroxy, alkoxy, substituted alkoxy, alkenoxy, substituted alkenoxy, alkynoxy, substituted alkynoxy, aryloxy and substituted aryloxy.

4. The conjugate of claim 3, wherein each poly(ethylene glycol) is terminally capped with methoxy.

5. The conjugate of claim 2, wherein each poly(ethylene glycol) has a molecular weight in a range from about 2,000 Daltons to about 85,000 Daltons.

6. The conjugate of claim 1, wherein each POLY possesses an architecture selected from the group consisting of linear, branched, and forked.

7. The conjugate of claim 1, wherein the EI is T-20.

8. The conjugate of claim 1, wherein the EI is T-1249.

9. The conjugate of claim 7, having structure II, wherein the T-20 is modified by hydrolyzable covalent attachment of the poly(alkylene oxide) at one or both of Lys-18, and Lys28.

10. The conjugate of claim 9, wherein the T-20 is further additionally modified by hydrolyzable covalent attachment of the poly(alkylene oxide) at the N-terminus.

11. The conjugate of claim 8, having structure II, wherein the T-1249 is modified by hydrolyzable covalent attachment of the poly(alklene oxide) at from one to three of amino acid positions selected from Lys7, Lys21, Lys28 and Lys31.

12. The conjugate of claim 1, where in structure III, P, when taken together with —NH—P—Z—C(O)—, is a residue of a naturally or non-naturally occurring amino acid.

13. The conjugate of claim 1, where Ar in structure II is an ortho, meta, or para-substituted phenyl group.

14. The conjugate of claim 1 having structure III, wherein P, when taken together with —NH—P—Z—C(O)—, is glyine or alanine.

15. The conjugate of claim 13, having structure:

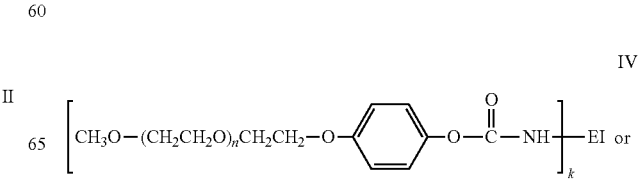

-continued

V

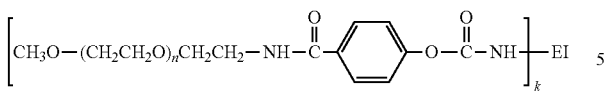

where n ranges from 2 to about 3400.

16. The conjugate of claim 1, wherein k equals 1.

17. A composition comprising a plurality of conjugates of claim 1, each conjugate comprised within the plurality having structure II and having a value of k from 1-3.

18. A pharmaceutical composition comprising a conjugate of claim 1 and a pharmaceutically acceptable excipient.

19. A method for making an HIV-entry inhibitor water-soluble polymer conjugate having structure H of claim 1, comprising contacting, under suitable conjugation conditions, an HIV entry inhibitor that is either T-20 or T-1249, with a polymeric reagent having the structure:

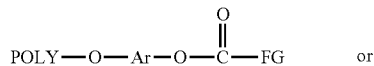 or

-continued

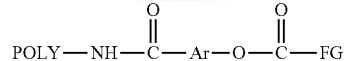

where POLY and Ar are as defined in claim 1, and where FG is a functional group capable of reaction with an amino group of the HIV entry inhibitor to form a hydrolyzable carbamate linkage.

20. A composition comprising a plurality of mono-conjugates of claim 1, each conjugate comprised within the plurality having structure II, and having the same chemical structure, where the value of k for each conjugate is 1, and the composition comprises at least two different positional isomers.

21. A composition comprising a plurality of conjugates of claim 1, each conjugate comprised within the plurality having structure III and having a value of k from 1-3.

22. A composition comprising a plurality of mono-conjugates of claim 1, each conjugate comprised within the plurality having structure III and having the same chemical structure, where the value of k for each conjugate is 1, and the composition comprises at least two different positional isomers.

* * * * *